(12) United States Patent  
Scheuermann et al.

(10) Patent No.: US 7,976,915 B2  
(45) Date of Patent: Jul. 12, 2011

(54) ENDOPROSTHESIS WITH SELECT CERAMIC MORPHOLOGY

(75) Inventors: Torsten Scheuermann, Munich (DE); Michael Kuehling, Munich (DE); Umang Anand, Minneapolis, MN (US); Jaydeep Y. Kokate, Maple Grove, MN (US); Samuel Robaina, Maple Grove, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 36 days.

(21) Appl. No.: 11/752,772

(22) Filed: May 23, 2007

(65) Prior Publication Data

US 2008/0294246 A1    Nov. 27, 2008

(51) Int. Cl.
*A47G 19/22* (2006.01)
*B32B 1/08* (2006.01)
*A61F 2/06* (2006.01)

(52) U.S. Cl. ............ 428/34.4; 428/34.7; 623/1.43; 623/1.4

(58) Field of Classification Search ............ 428/34.4, 428/34.7; 623/1.43, 1.4
See application file for complete search history.

(56) References Cited

U.S. PATENT DOCUMENTS

| 3,751,283 A | 8/1973 | Dawson |
| 3,758,396 A | 9/1973 | Vieth et al. |
| 3,910,819 A | 10/1975 | Rembaum et al. |
| 3,948,254 A | 4/1976 | Zaffaroni |
| 3,952,334 A | 4/1976 | Bokros et al. |
| 3,970,445 A | 7/1976 | Gale et al. |
| 3,993,072 A | 11/1976 | Zaffaroni |
| 4,044,404 A | 8/1977 | Martin et al. |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,321,311 A | 3/1982 | Strangman |
| 4,330,891 A | 5/1982 | Branemark et al. |
| 4,334,327 A | 6/1982 | Lyman et al. |
| 4,401,546 A | 8/1983 | Nakamura et al. |
| 4,407,695 A | 10/1983 | Deckman et al. |
| 4,475,972 A | 10/1984 | Wong |
| 4,565,744 A | 1/1986 | Walter et al. |
| 4,585,652 A | 4/1986 | Miller et al. |
| 4,655,771 A | 4/1987 | Wallsten |
| 4,657,544 A | 4/1987 | Pinchuk |
| 4,665,896 A | 5/1987 | LaForge et al. |

(Continued)

FOREIGN PATENT DOCUMENTS

AT      232704      3/2003

(Continued)

OTHER PUBLICATIONS

Dibra et al. "Influence of Stent Surface Topography on the Outcomes of Patients Undergoing Coronary Stenting: A Randomized Double-Blind Controlled Trial"; Catheterization and Cardiovascular Interventions 65:374-380 (2005).*

(Continued)

*Primary Examiner* — Rena L Dye
*Assistant Examiner* — James Yager
(74) *Attorney, Agent, or Firm* — Fish & Richardson P.C.

(57) ABSTRACT

An endoprosthesis, such as a stent, includes a ceramic, such as IROX, having a select morphology and composition.

39 Claims, 16 Drawing Sheets

U.S. PATENT DOCUMENTS

| | | |
|---|---|---|
| 4,705,502 A | 11/1987 | Patel |
| 4,733,665 A | 3/1988 | Palmaz |
| 4,738,740 A | 4/1988 | Pinchuk et al. |
| 4,743,252 A | 5/1988 | Martin et al. |
| 4,784,659 A | 11/1988 | Fleckenstein et al. |
| 4,800,882 A | 1/1989 | Gianturco |
| 4,842,505 A | 6/1989 | Annis et al. |
| 4,886,062 A | 12/1989 | Wiktor |
| 4,902,290 A | 2/1990 | Fleckenstein et al. |
| 4,954,126 A | 9/1990 | Wallsten |
| 4,976,692 A | 12/1990 | Atad |
| 4,994,071 A | 2/1991 | MacGregor |
| 5,061,275 A | 10/1991 | Wallsten et al. |
| 5,061,914 A | 10/1991 | Busch et al. |
| 5,073,365 A | 12/1991 | Katz et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,171,607 A | 12/1992 | Cumbo |
| 5,195,969 A | 3/1993 | Wang et al. |
| 5,205,921 A | 4/1993 | Shirkanzadeh |
| 5,219,611 A | 6/1993 | Giannelis et al. |
| 5,232,444 A | 8/1993 | Just et al. |
| 5,236,413 A | 8/1993 | Feiring |
| 5,250,242 A | 10/1993 | Nishio et al. |
| 5,270,086 A | 12/1993 | Hamlin |
| 5,279,292 A | 1/1994 | Baumann et al. |
| 5,290,585 A | 3/1994 | Elton |
| 5,302,414 A | 4/1994 | Alkhimov et al. |
| 5,304,121 A | 4/1994 | Sahatjian |
| 5,314,453 A | 5/1994 | Jeutter |
| 5,322,520 A | 6/1994 | Milder |
| 5,326,354 A | 7/1994 | Kwarteng |
| 5,348,553 A | 9/1994 | Whitney |
| 5,366,504 A | 11/1994 | Andersen et al. |
| 5,368,881 A | 11/1994 | Kelman et al. |
| 5,378,146 A | 1/1995 | Sterrett |
| 5,380,298 A | 1/1995 | Zabetakis et al. |
| 5,383,935 A | 1/1995 | Shirkhanzadeh |
| 5,397,307 A | 3/1995 | Goodin |
| 5,405,367 A | 4/1995 | Schulman et al. |
| 5,439,446 A | 8/1995 | Barry |
| 5,443,496 A | 8/1995 | Schwartz et al. |
| 5,447,724 A | 9/1995 | Helmus et al. |
| 5,449,373 A | 9/1995 | Pinchasik et al. |
| 5,449,382 A | 9/1995 | Dayton |
| 5,464,450 A | 11/1995 | Buscemi et al. |
| 5,464,650 A | 11/1995 | Berg et al. |
| 5,474,797 A | 12/1995 | Sioshansi et al. |
| 5,500,013 A | 3/1996 | Buscemi et al. |
| 5,527,337 A | 6/1996 | Stack et al. |
| 5,545,208 A | 8/1996 | Wolff et al. |
| 5,551,954 A | 9/1996 | Buscemi et al. |
| 5,569,463 A | 10/1996 | Helmus et al. |
| 5,578,075 A | 11/1996 | Dayton |
| 5,587,507 A | 12/1996 | Kohn et al. |
| 5,591,224 A | 1/1997 | Schwartz et al. |
| 5,603,556 A | 2/1997 | Klink |
| 5,605,696 A | 2/1997 | Eury et al. |
| 5,607,463 A | 3/1997 | Schwartz et al. |
| 5,607,467 A | 3/1997 | Froix |
| 5,609,629 A | 3/1997 | Fearnot et al. |
| 5,614,549 A | 3/1997 | Greenwald et al. |
| 5,624,411 A | 4/1997 | Tuch |
| 5,649,951 A | 7/1997 | Davidson |
| 5,649,977 A | 7/1997 | Campbell |
| 5,672,242 A | 9/1997 | Jen |
| 5,674,192 A | 10/1997 | Sahatjian et al. |
| 5,674,242 A | 10/1997 | Phan et al. |
| 5,679,440 A | 10/1997 | Kubota |
| 5,681,196 A | 10/1997 | Jin et al. |
| 5,690,670 A | 11/1997 | Davidson |
| 5,693,085 A | 12/1997 | Buirge et al. |
| 5,693,928 A | 12/1997 | Egitto et al. |
| 5,711,866 A | 1/1998 | Lashmore et al. |
| 5,733,924 A | 3/1998 | Kanda et al. |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,758,562 A | 6/1998 | Thompson |
| 5,761,775 A | 6/1998 | Legome et al. |
| 5,769,883 A | 6/1998 | Buscemi et al. |
| 5,772,864 A | 6/1998 | Moller et al. |
| 5,776,184 A | 7/1998 | Tuch |
| 5,780,807 A | 7/1998 | Saunders |
| 5,788,687 A | 8/1998 | Batich et al. |
| 5,788,979 A | 8/1998 | Alt et al. |
| 5,795,626 A | 8/1998 | Gabel et al. |
| 5,797,898 A | 8/1998 | Santini, Jr. et al. |
| 5,807,407 A | 9/1998 | England et al. |
| 5,817,046 A | 10/1998 | Glickman |
| 5,824,045 A | 10/1998 | Alt |
| 5,824,048 A | 10/1998 | Tuch |
| 5,824,049 A | 10/1998 | Ragheb et al. |
| 5,824,077 A | 10/1998 | Mayer |
| 5,830,480 A | 11/1998 | Ducheyne et al. |
| 5,837,313 A | 11/1998 | Ding et al. |
| 5,843,089 A | 12/1998 | Sahatjian et al. |
| 5,843,172 A | 12/1998 | Yan |
| 5,852,088 A | 12/1998 | Dismukes et al. |
| 5,858,556 A | 1/1999 | Eckert et al. |
| 5,873,904 A | 2/1999 | Ragheb et al. |
| 5,874,134 A | 2/1999 | Rao et al. |
| 5,879,697 A | 3/1999 | Ding et al. |
| 5,882,335 A | 3/1999 | Leone et al. |
| 5,888,591 A | 3/1999 | Gleason et al. |
| 5,891,108 A | 4/1999 | Leone et al. |
| 5,891,192 A | 4/1999 | Murayama et al. |
| 5,902,266 A | 5/1999 | Leone et al. |
| 5,922,021 A | 7/1999 | Jang |
| 5,928,247 A | 7/1999 | Barry et al. |
| 5,951,881 A | 9/1999 | Rogers et al. |
| 5,954,706 A | 9/1999 | Sahatjian |
| 5,962,136 A | 10/1999 | Dewez et al. |
| 5,968,091 A | 10/1999 | Pinchuk et al. |
| 5,968,092 A | 10/1999 | Buscemi et al. |
| 5,968,640 A | 10/1999 | Lubowitz et al. |
| 5,972,027 A | 10/1999 | Johnson |
| 5,977,204 A | 11/1999 | Boyan et al. |
| 5,980,564 A | 11/1999 | Stinson |
| 5,980,566 A | 11/1999 | Alt et al. |
| 6,013,591 A | 1/2000 | Ying et al. |
| 6,017,577 A | 1/2000 | Hostettler et al. |
| 6,022,812 A | 2/2000 | Smith et al. |
| 6,025,036 A | 2/2000 | McGill et al. |
| 6,034,295 A | 3/2000 | Rehberg et al. |
| 6,045,877 A | 4/2000 | Gleason et al. |
| 6,063,101 A | 5/2000 | Jacobsen et al. |
| 6,071,305 A | 6/2000 | Brown et al. |
| 6,074,135 A | 6/2000 | Tapphorn et al. |
| 6,096,070 A | 8/2000 | Ragheb et al. |
| 6,099,561 A | 8/2000 | Alt |
| 6,099,562 A | 8/2000 | Ding et al. |
| 6,106,473 A | 8/2000 | Violante et al. |
| 6,120,536 A | 9/2000 | Ding et al. |
| 6,120,660 A | 9/2000 | Chu et al. |
| 6,122,564 A | 9/2000 | Koch et al. |
| 6,139,573 A | 10/2000 | Sogard et al. |
| 6,139,913 A | 10/2000 | Van Steenkiste et al. |
| 6,153,252 A | 11/2000 | Hossainy et al. |
| 6,156,435 A | 12/2000 | Gleason et al. |
| 6,159,142 A | 12/2000 | Alt |
| 6,171,609 B1 | 1/2001 | Kunz |
| 6,174,329 B1 | 1/2001 | Callol et al. |
| 6,174,330 B1 | 1/2001 | Stinson |
| 6,180,184 B1 | 1/2001 | Gray et al. |
| 6,187,037 B1 | 2/2001 | Satz |
| 6,190,404 B1 | 2/2001 | Palmaz et al. |
| 6,193,761 B1 | 2/2001 | Treacy |
| 6,200,685 B1 | 3/2001 | Davidson |
| 6,203,536 B1 | 3/2001 | Berg et al. |
| 6,206,915 B1 | 3/2001 | Fagan et al. |
| 6,206,916 B1 | 3/2001 | Furst |

| Patent | Date | Inventor |
|---|---|---|
| 6,210,715 B1 | 4/2001 | Starling et al. |
| 6,212,607 B1 | 4/2001 | Miller et al. |
| 6,214,042 B1 | 4/2001 | Jacobsen et al. |
| 6,217,607 B1 | 4/2001 | Alt |
| 6,231,600 B1 | 5/2001 | Zhong |
| 6,240,616 B1 | 6/2001 | Yan |
| 6,241,762 B1 | 6/2001 | Shanley |
| 6,245,104 B1 | 6/2001 | Alt |
| 6,249,952 B1 | 6/2001 | Ding |
| 6,251,136 B1 | 6/2001 | Guruwaiya et al. |
| 6,253,443 B1 | 7/2001 | Johnson |
| 6,254,632 B1 | 7/2001 | Wu et al. |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,280,411 B1 | 8/2001 | Lennox |
| 6,283,386 B1 | 9/2001 | Van Steenkiste et al. |
| 6,284,305 B1 | 9/2001 | Ding et al. |
| 6,287,331 B1 | 9/2001 | Heath |
| 6,287,332 B1 | 9/2001 | Bolz et al. |
| 6,287,628 B1 | 9/2001 | Hossainy et al. |
| 6,290,721 B1 | 9/2001 | Heath |
| 6,299,604 B1 | 10/2001 | Ragheb et al. |
| 6,306,144 B1 | 10/2001 | Sydney et al. |
| 6,315,708 B1 | 11/2001 | Salmon et al. |
| 6,315,794 B1 | 11/2001 | Richter |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,330 B1 | 12/2001 | Choy et al. |
| 6,335,029 B1 | 1/2002 | Kamath et al. |
| 6,337,076 B1 | 1/2002 | Studin |
| 6,342,507 B1 | 1/2002 | Naicker et al. |
| 6,348,960 B1 | 2/2002 | Etori et al. |
| 6,358,532 B2 | 3/2002 | Starling et al. |
| 6,358,556 B1 | 3/2002 | Ding et al. |
| 6,364,856 B1 | 4/2002 | Ding et al. |
| 6,367,412 B1 | 4/2002 | Ramaswamy et al. |
| 6,368,658 B1 | 4/2002 | Schwarz et al. |
| 6,379,383 B1 | 4/2002 | Palmaz et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,052 B2 | 5/2002 | Buirge et al. |
| 6,395,325 B1 | 5/2002 | Hedge et al. |
| 6,395,326 B1 | 5/2002 | Castro et al. |
| 6,398,806 B1 | 6/2002 | You |
| 6,413,271 B1 | 7/2002 | Hafeli et al. |
| 6,416,820 B1 | 7/2002 | Yamada et al. |
| 6,419,692 B1 | 7/2002 | Yang et al. |
| 6,436,133 B1 | 8/2002 | Furst et al. |
| 6,440,503 B1 | 8/2002 | Merdan et al. |
| 6,458,153 B1 | 10/2002 | Bailey et al. |
| 6,465,052 B1 | 10/2002 | Wu |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,418 B2 | 11/2002 | Li et al. |
| 6,488,715 B1 | 12/2002 | Pope et al. |
| 6,491,666 B1 | 12/2002 | Santini, Jr. et al. |
| 6,491,720 B1 | 12/2002 | Vallana et al. |
| 6,503,921 B2 | 1/2003 | Naicker et al. |
| 6,504,292 B1 | 1/2003 | Choi et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,514,289 B1 | 2/2003 | Pope et al. |
| 6,517,888 B1 | 2/2003 | Weber |
| 6,524,274 B1 | 2/2003 | Rosenthal et al. |
| 6,527,801 B1 | 3/2003 | Dutta |
| 6,527,938 B2 | 3/2003 | Bales et al. |
| 6,530,951 B1 | 3/2003 | Bates et al. |
| 6,537,310 B1 | 3/2003 | Palmaz et al. |
| 6,544,582 B1 | 4/2003 | Yoe |
| 6,545,097 B2 | 4/2003 | Pinchuk et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,585,765 B1 | 7/2003 | Hossainy et al. |
| 6,599,558 B1 | 7/2003 | Al-Lamee et al. |
| 6,607,598 B2 | 8/2003 | Schwarz et al. |
| 6,613,083 B2 | 9/2003 | Alt |
| 6,613,432 B2 | 9/2003 | Zamora et al. |
| 6,616,765 B1 | 9/2003 | Wu et al. |
| 6,620,194 B2 | 9/2003 | Ding et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,999 B1 | 1/2004 | Wang et al. |
| 6,676,987 B2 | 1/2004 | Zhong et al. |
| 6,676,989 B2 | 1/2004 | Kirkpatrick et al. |
| 6,689,803 B2 | 2/2004 | Hunter |
| 6,695,865 B2 | 2/2004 | Boyle et al. |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,723,120 B2 | 4/2004 | Yan |
| 6,725,901 B1 | 4/2004 | Kramer et al. |
| 6,726,712 B1 | 4/2004 | Raeder-Devens et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,736,849 B2 | 5/2004 | Li et al. |
| 6,740,077 B1 | 5/2004 | Brandau et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,761,736 B1 | 7/2004 | Woo et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,780,424 B2 | 8/2004 | Claude |
| 6,780,491 B1 | 8/2004 | Cathey et al. |
| 6,783,543 B2 | 8/2004 | Jang |
| 6,790,228 B2 | 9/2004 | Hossainy et al. |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| 6,815,609 B1 | 11/2004 | Wang et al. |
| 6,820,676 B2 | 11/2004 | Palmaz et al. |
| 6,827,737 B2 | 12/2004 | Hill et al. |
| 6,830,598 B1 | 12/2004 | Sung |
| 6,833,004 B2 | 12/2004 | Ishii et al. |
| 6,846,323 B2 | 1/2005 | Yip et al. |
| 6,846,841 B2 | 1/2005 | Hunter et al. |
| 6,849,085 B2 | 2/2005 | Marton |
| 6,849,089 B2 | 2/2005 | Stoll |
| 6,852,122 B2 | 2/2005 | Rush |
| 6,861,088 B2 | 3/2005 | Weber et al. |
| 6,866,805 B2 | 3/2005 | Hong et al. |
| 6,869,443 B2 | 3/2005 | Buscemi et al. |

| | | | | | |
|---|---|---|---|---|---|
| 6,869,701 B1 | 3/2005 | Aita et al. | 7,494,950 B2 | 2/2009 | Armitage et al. |
| 6,875,227 B2 | 4/2005 | Yoon | 7,497,876 B2 | 3/2009 | Tuke et al. |
| 6,878,249 B2 | 4/2005 | Kouyama et al. | 7,547,445 B2 | 6/2009 | Chudzik et al. |
| 6,884,429 B2 | 4/2005 | Koziak et al. | 7,563,324 B1 | 7/2009 | Chen et al. |
| 6,896,697 B1 | 5/2005 | Yip et al. | 7,575,593 B2 | 8/2009 | Rea et al. |
| 6,899,914 B2 | 5/2005 | Schaldach et al. | 7,635,515 B1 | 12/2009 | Sherman |
| 6,904,658 B2 | 6/2005 | Hines | 7,638,156 B1 | 12/2009 | Hossainy et al. |
| 6,908,622 B2 | 6/2005 | Barry et al. | 7,691,461 B1 | 4/2010 | Prabhu |
| 6,908,624 B2 | 6/2005 | Hossainy et al. | 7,713,297 B2 | 5/2010 | Alt |
| 6,913,617 B1 | 7/2005 | Reiss | 7,727,275 B2 | 6/2010 | Betts et al. |
| 6,915,796 B2 | 7/2005 | Sung | 7,749,264 B2 | 7/2010 | Gregorich et al. |
| 6,918,927 B2 | 7/2005 | Bates et al. | 7,758,636 B2 | 7/2010 | Shanley et al. |
| 6,923,829 B2 | 8/2005 | Boyle et al. | 7,771,773 B2 | 8/2010 | Namavar |
| 6,924,004 B2 | 8/2005 | Rao et al. | 7,837,726 B2 | 11/2010 | Von Oepen et al. |
| 6,932,930 B2 | 8/2005 | DeSimone et al. | 2001/0001834 A1 | 5/2001 | Palmaz et al. |
| 6,936,066 B2 | 8/2005 | Palmaz et al. | 2001/0002000 A1 | 5/2001 | Kumar et al. |
| 6,939,320 B2 | 9/2005 | Lennox | 2001/0002435 A1 | 5/2001 | Berg et al. |
| 6,951,053 B2 | 10/2005 | Padilla et al. | 2001/0013166 A1 | 8/2001 | Yan |
| 6,953,560 B1 | 10/2005 | Castro et al. | 2001/0014717 A1 | 8/2001 | Hossainy et al. |
| 6,955,661 B1 | 10/2005 | Herweck et al. | 2001/0014821 A1 | 8/2001 | Juman et al. |
| 6,955,685 B2 | 10/2005 | Escamilla et al. | 2001/0027299 A1 | 10/2001 | Yang et al. |
| 6,962,822 B2 | 11/2005 | Hart et al. | 2001/0029660 A1 | 10/2001 | Johnson |
| 6,971,813 B2 | 12/2005 | Shekalim et al. | 2001/0032011 A1 | 10/2001 | Stanford |
| 6,973,718 B2 | 12/2005 | Sheppard, Jr. et al. | 2001/0032013 A1 | 10/2001 | Marton |
| 6,979,346 B1 | 12/2005 | Hossainy et al. | 2001/0044651 A1 | 11/2001 | Steinke et al. |
| 6,979,348 B2 | 12/2005 | Sundar | 2002/0000175 A1 | 1/2002 | Hintermaier et al. |
| 6,984,404 B1 | 1/2006 | Talton et al. | 2002/0004060 A1 | 1/2002 | Heublein et al. |
| 7,001,421 B2 | 2/2006 | Cheng et al. | 2002/0007102 A1 | 1/2002 | Salmon et al. |
| 7,011,680 B2 | 3/2006 | Alt | 2002/0007209 A1 | 1/2002 | Schearder et al. |
| 7,014,654 B2 | 3/2006 | Welsh et al. | 2002/0009604 A1 | 1/2002 | Zamora et al. |
| 7,018,408 B2 | 3/2006 | Bailey et al. | 2002/0010505 A1 | 1/2002 | Richter |
| 7,041,130 B2 | 5/2006 | Santini, Jr. et al. | 2002/0016623 A1 | 2/2002 | Kula et al. |
| 7,048,939 B2 | 5/2006 | Elkins et al. | 2002/0016624 A1 | 2/2002 | Patterson et al. |
| 7,052,488 B2 | 5/2006 | Uhland | 2002/0028827 A1 | 3/2002 | Naicker et al. |
| 7,056,338 B2 | 6/2006 | Shanley et al. | 2002/0032477 A1 | 3/2002 | Helmus et al. |
| 7,056,339 B2 | 6/2006 | Elkins et al. | 2002/0038146 A1 | 3/2002 | Harry |
| 7,056,591 B1 | 6/2006 | Pacetti et al. | 2002/0042039 A1 | 4/2002 | Kim et al. |
| 7,060,051 B2 | 6/2006 | Palasis | 2002/0051730 A1 | 5/2002 | Bodnar et al. |
| 7,063,748 B2 | 6/2006 | Talton | 2002/0051846 A1 | 5/2002 | Kirkpatrick et al. |
| 7,066,234 B2 | 6/2006 | Sawitowski | 2002/0052288 A1 | 5/2002 | Krell et al. |
| 7,077,859 B2 | 7/2006 | Sirhan et al. | 2002/0065553 A1 | 5/2002 | Weber |
| 7,078,108 B2 | 7/2006 | Zhang et al. | 2002/0072734 A1 | 6/2002 | Liedtke |
| 7,083,642 B2 | 8/2006 | Sirhan et al. | 2002/0077520 A1 | 6/2002 | Segal et al. |
| 7,087,661 B1 | 8/2006 | Alberte et al. | 2002/0077693 A1 | 6/2002 | Barclay et al. |
| 7,099,091 B2 | 8/2006 | Taniguchi et al. | 2002/0087123 A1 | 7/2002 | Hossainy et al. |
| 7,101,391 B2 | 9/2006 | Scheuermann et al. | 2002/0091375 A1 | 7/2002 | Sahatjian et al. |
| 7,101,394 B2 | 9/2006 | Hamm et al. | 2002/0095871 A1 | 7/2002 | McArdle et al. |
| 7,105,018 B1 | 9/2006 | Yip et al. | 2002/0098278 A1 | 7/2002 | Bates et al. |
| 7,105,199 B2 | 9/2006 | Blinn et al. | 2002/0099359 A1 | 7/2002 | Santini, Jr. et al. |
| 7,144,840 B2 | 12/2006 | Yeung et al. | 2002/0099438 A1 | 7/2002 | Furst |
| 7,160,592 B2 | 1/2007 | Rypacek et al. | 2002/0103527 A1 | 8/2002 | Kocur et al. |
| 7,163,715 B1 | 1/2007 | Kramer | 2002/0103528 A1 | 8/2002 | Schaldach et al. |
| 7,169,177 B2 | 1/2007 | Obara | 2002/0104599 A1 | 8/2002 | Tillotson et al. |
| 7,169,178 B1 | 1/2007 | Santos et al. | 2002/0121497 A1 | 9/2002 | Tomonto |
| 7,195,640 B2 | 3/2007 | Falotico et al. | 2002/0123801 A1 | 9/2002 | Pacetti et al. |
| 7,195,641 B2 | 3/2007 | Palmaz et al. | 2002/0133222 A1 | 9/2002 | Das |
| 7,198,675 B2 | 4/2007 | Fox et al. | 2002/0133225 A1 | 9/2002 | Gordon |
| 7,208,011 B2 | 4/2007 | Shanley et al. | 2002/0138100 A1 | 9/2002 | Stoll et al. |
| 7,208,172 B2 | 4/2007 | Birdsall et al. | 2002/0138136 A1 | 9/2002 | Chandresekaran et al. |
| 7,229,471 B2 | 6/2007 | Gale et al. | 2002/0140137 A1 | 10/2002 | Sapieszko et al. |
| 7,235,096 B1 | 6/2007 | Van Tassel et al. | 2002/0142579 A1 | 10/2002 | Vincent et al. |
| 7,235,098 B2 | 6/2007 | Palmaz | 2002/0144757 A1 | 10/2002 | Craig et al. |
| 7,238,199 B2 | 7/2007 | Feldman et al. | 2002/0155212 A1 | 10/2002 | Hossainy |
| 7,244,272 B2 | 7/2007 | Dubson et al. | 2002/0165265 A1 | 11/2002 | Hunter et al. |
| 7,247,166 B2 | 7/2007 | Pienknagura | 2002/0165600 A1 | 11/2002 | Banas et al. |
| 7,247,338 B2 | 7/2007 | Pui et al. | 2002/0165607 A1 | 11/2002 | Alt |
| 7,261,735 B2 | 8/2007 | Llanos et al. | 2002/0167118 A1 | 11/2002 | Billiet et al. |
| 7,261,752 B2 | 8/2007 | Sung | 2002/0168466 A1 | 11/2002 | Tapphorn et al. |
| 7,273,493 B2 | 9/2007 | Ledergerber | 2002/0169493 A1 | 11/2002 | Widenhouse et al. |
| 7,294,409 B2 | 11/2007 | Lye et al. | 2002/0178570 A1 | 12/2002 | Sogard et al. |
| 7,311,727 B2 | 12/2007 | Mazumder et al. | 2002/0182241 A1 | 12/2002 | Borenstein et al. |
| 7,344,563 B2 | 3/2008 | Vallana et al. | 2002/0183581 A1 | 12/2002 | Yoe et al. |
| 7,368,065 B2 | 5/2008 | Yang et al. | 2002/0183682 A1 | 12/2002 | Darvish et al. |
| 7,393,589 B2 | 7/2008 | Aharonov et al. | 2002/0187260 A1 | 12/2002 | Sheppard, Jr. et al. |
| 7,396,538 B2 | 7/2008 | Granada et al. | 2002/0193336 A1 | 12/2002 | Elkins et al. |
| 7,402,173 B2 | 7/2008 | Scheuermann et al. | 2002/0193869 A1 | 12/2002 | Dang |
| 7,416,558 B2 | 8/2008 | Yip et al. | 2002/0197178 A1 | 12/2002 | Yan |
| 7,435,256 B2 | 10/2008 | Stenzel | 2002/0198601 A1 | 12/2002 | Bales et al. |
| 7,482,034 B2 | 1/2009 | Boulais | 2003/0003160 A1 | 1/2003 | Pugh et al. |

| Publication No. | Date | Inventor |
|---|---|---|
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0006250 A1 | 1/2003 | Tapphorn et al. |
| 2003/0009214 A1 | 1/2003 | Shanley |
| 2003/0009233 A1 | 1/2003 | Blinn et al. |
| 2003/0018380 A1 | 1/2003 | Craig et al. |
| 2003/0018381 A1 | 1/2003 | Whitcher et al. |
| 2003/0021820 A1 | 1/2003 | Ahola et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0047028 A1 | 3/2003 | Kunitake et al. |
| 2003/0047505 A1 | 3/2003 | Grimes et al. |
| 2003/0050687 A1 | 3/2003 | Schwade et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0060877 A1 | 3/2003 | Falotico et al. |
| 2003/0064095 A1 | 4/2003 | Martin et al. |
| 2003/0069631 A1 | 4/2003 | Stoll |
| 2003/0074053 A1 | 4/2003 | Palmaz et al. |
| 2003/0074075 A1 | 4/2003 | Thomas et al. |
| 2003/0077200 A1 | 4/2003 | Craig et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1 | 5/2003 | Shulze et al. |
| 2003/0088312 A1 | 5/2003 | Kopia et al. |
| 2003/0100865 A1 | 5/2003 | Santini, Jr. et al. |
| 2003/0104028 A1 | 6/2003 | Hossainy et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118649 A1 | 6/2003 | Gao et al. |
| 2003/0125803 A1 | 7/2003 | Vallana et al. |
| 2003/0130206 A1 | 7/2003 | Koziak et al. |
| 2003/0130718 A1 | 7/2003 | Palmas et al. |
| 2003/0138645 A1 | 7/2003 | Gleason et al. |
| 2003/0139799 A1 | 7/2003 | Ley et al. |
| 2003/0144728 A1 | 7/2003 | Scheuermann et al. |
| 2003/0150380 A1 | 8/2003 | Yoe |
| 2003/0153901 A1 | 8/2003 | Herweck et al. |
| 2003/0153971 A1 | 8/2003 | Chandrasekaran |
| 2003/0158598 A1 | 8/2003 | Ashton et al. |
| 2003/0167878 A1 | 9/2003 | Al-Salim et al. |
| 2003/0170605 A1 | 9/2003 | Long et al. |
| 2003/0181975 A1 | 9/2003 | Ishii et al. |
| 2003/0185895 A1 | 10/2003 | Lanphere et al. |
| 2003/0185964 A1 | 10/2003 | Weber et al. |
| 2003/0190406 A1 | 10/2003 | Hossainy et al. |
| 2003/0195613 A1 | 10/2003 | Curcio et al. |
| 2003/0203991 A1 | 10/2003 | Schottman et al. |
| 2003/0204168 A1 | 10/2003 | Bosma et al. |
| 2003/0208256 A1 | 11/2003 | DiMatteo et al. |
| 2003/0211135 A1 | 11/2003 | Greenhalgh et al. |
| 2003/0216803 A1 | 11/2003 | Ledergerber |
| 2003/0219562 A1 | 11/2003 | Rypacek et al. |
| 2003/0225450 A1 | 12/2003 | Shulze et al. |
| 2003/0236323 A1 | 12/2003 | Ratner et al. |
| 2003/0236514 A1 | 12/2003 | Schwarz |
| 2004/0000540 A1 | 1/2004 | Soboyejo et al. |
| 2004/0002755 A1 | 1/2004 | Fischell et al. |
| 2004/0006382 A1 | 1/2004 | Sohier |
| 2004/0013873 A1 | 1/2004 | Wendorff et al. |
| 2004/0016651 A1 | 1/2004 | Windler |
| 2004/0018296 A1 | 1/2004 | Castro et al. |
| 2004/0019376 A1 | 1/2004 | Alt |
| 2004/0022824 A1 | 2/2004 | Li et al. |
| 2004/0026811 A1 | 2/2004 | Murphy et al. |
| 2004/0028875 A1 | 2/2004 | Van Rijn et al. |
| 2004/0029303 A1 | 2/2004 | Hart et al. |
| 2004/0029706 A1 | 2/2004 | Barrera et al. |
| 2004/0030218 A1 | 2/2004 | Kocur et al. |
| 2004/0030377 A1 | 2/2004 | Dubson et al. |
| 2004/0039438 A1 | 2/2004 | Alt |
| 2004/0039441 A1 | 2/2004 | Rowland et al. |
| 2004/0044397 A1 | 3/2004 | Stinson |
| 2004/0047980 A1 | 3/2004 | Pacetti et al. |
| 2004/0058858 A1 | 3/2004 | Hu |
| 2004/0059290 A1 | 3/2004 | Palasis |
| 2004/0059407 A1 | 3/2004 | Escamilla et al. |
| 2004/0059409 A1 | 3/2004 | Stenzel |
| 2004/0067301 A1 | 4/2004 | Ding |
| 2004/0071861 A1 | 4/2004 | Mandrusov et al. |
| 2004/0073284 A1 | 4/2004 | Bates et al. |
| 2004/0073298 A1 | 4/2004 | Hossainy |
| 2004/0078071 A1 | 4/2004 | Escamilla et al. |
| 2004/0086674 A1 | 5/2004 | Holman |
| 2004/0088038 A1 | 5/2004 | Dehnad et al. |
| 2004/0088041 A1 | 5/2004 | Stanford |
| 2004/0092653 A1 | 5/2004 | Ruberti et al. |
| 2004/0093071 A1 | 5/2004 | Jang |
| 2004/0093076 A1 | 5/2004 | White et al. |
| 2004/0098089 A1 | 5/2004 | Weber |
| 2004/0098119 A1 | 5/2004 | Wang |
| 2004/0102758 A1 | 5/2004 | Davila et al. |
| 2004/0106984 A1 | 6/2004 | Stinson |
| 2004/0106985 A1 | 6/2004 | Jang |
| 2004/0106987 A1 | 6/2004 | Palasis et al. |
| 2004/0106994 A1 | 6/2004 | De Maeztus Martinez et al. |
| 2004/0111150 A1 | 6/2004 | Berg et al. |
| 2004/0116999 A1 | 6/2004 | Ledergerber |
| 2004/0117005 A1 | 6/2004 | Gadde et al. |
| 2004/0117008 A1 | 6/2004 | Wnendt et al. |
| 2004/0122504 A1 | 6/2004 | Hogendijk |
| 2004/0126566 A1 | 7/2004 | Axen et al. |
| 2004/0133270 A1 | 7/2004 | Grandt |
| 2004/0134886 A1 | 7/2004 | Wagner et al. |
| 2004/0142014 A1 | 7/2004 | Litvack et al. |
| 2004/0143317 A1 | 7/2004 | Stinson et al. |
| 2004/0143321 A1 | 7/2004 | Litvack et al. |
| 2004/0148010 A1 | 7/2004 | Rush |
| 2004/0148015 A1 | 7/2004 | Lye et al. |
| 2004/0158308 A1 | 8/2004 | Hogendijk et al. |
| 2004/0167572 A1 | 8/2004 | Roth et al. |
| 2004/0167612 A1 | 8/2004 | Grignani et al. |
| 2004/0171978 A1 | 9/2004 | Shalaby |
| 2004/0172124 A1 | 9/2004 | Vallana et al. |
| 2004/0178523 A1 | 9/2004 | Kim et al. |
| 2004/0181252 A1 | 9/2004 | Boyle et al. |
| 2004/0181275 A1 | 9/2004 | Noble et al. |
| 2004/0181276 A1 | 9/2004 | Brown et al. |
| 2004/0185168 A1 | 9/2004 | Weber et al. |
| 2004/0191293 A1 | 9/2004 | Claude |
| 2004/0191404 A1 | 9/2004 | Hossainy et al. |
| 2004/0202692 A1 | 10/2004 | Shanley et al. |
| 2004/0204750 A1 | 10/2004 | Dinh |
| 2004/0211362 A1 | 10/2004 | Castro et al. |
| 2004/0215169 A1 | 10/2004 | Li |
| 2004/0215313 A1 | 10/2004 | Cheng |
| 2004/0219214 A1 | 11/2004 | Gravett et al. |
| 2004/0220510 A1 | 11/2004 | Koullick et al. |
| 2004/0220662 A1 | 11/2004 | Dang et al. |
| 2004/0224001 A1 | 11/2004 | Pacetti et al. |
| 2004/0225346 A1 | 11/2004 | Mazumder et al. |
| 2004/0225347 A1 | 11/2004 | Lang |
| 2004/0228905 A1 | 11/2004 | Greenspan et al. |
| 2004/0230176 A1 | 11/2004 | Shanahan et al. |
| 2004/0230290 A1 | 11/2004 | Weber et al. |
| 2004/0230293 A1 | 11/2004 | Yip et al. |
| 2004/0234737 A1 | 11/2004 | Pacetti |
| 2004/0234748 A1 | 11/2004 | Stenzel |
| 2004/0236399 A1 | 11/2004 | Sundar |
| 2004/0236415 A1 | 11/2004 | Thomas |
| 2004/0236416 A1 | 11/2004 | Falotico |
| 2004/0237282 A1 | 12/2004 | Hines |
| 2004/0242106 A1 | 12/2004 | Rabasco et al. |
| 2004/0243217 A1 | 12/2004 | Andersen et al. |
| 2004/0243241 A1 | 12/2004 | Istephanous |
| 2004/0247671 A1 | 12/2004 | Prescott et al. |
| 2004/0249444 A1 | 12/2004 | Reiss |
| 2004/0249449 A1 | 12/2004 | Shanley et al. |

| | | | | | | |
|---|---|---|---|---|---|---|
| 2004/0254635 A1 | 12/2004 | Shanley et al. | | 2005/0221072 A1* | 10/2005 | Dubrow et al. ............ 428/292.1 |
| 2004/0261702 A1 | 12/2004 | Grabowy et al. | | 2005/0228477 A1 | 10/2005 | Grainger et al. |
| 2005/0002865 A1 | 1/2005 | Klaveness et al. | | 2005/0228491 A1 | 10/2005 | Snyder et al. |
| 2005/0004663 A1 | 1/2005 | Llanos et al. | | 2005/0232968 A1 | 10/2005 | Palmaz et al. |
| 2005/0010275 A1 | 1/2005 | Sahatjian et al. | | 2005/0233965 A1 | 10/2005 | Schwartz et al. |
| 2005/0015142 A1 | 1/2005 | Austin et al. | | 2005/0271703 A1 | 10/2005 | Snyder et al. |
| 2005/0019265 A1 | 1/2005 | Hammer et al. | | 2005/0244459 A1 | 11/2005 | DeWitt et al. |
| 2005/0019371 A1 | 1/2005 | Anderson et al. | | 2005/0251245 A1 | 11/2005 | Sieradzki et al. |
| 2005/0020614 A1 | 1/2005 | Prescott et al. | | 2005/0251249 A1 | 11/2005 | Sahatjian et al. |
| 2005/0021127 A1 | 1/2005 | Kawula | | 2005/0255707 A1 | 11/2005 | Hart et al. |
| 2005/0021128 A1 | 1/2005 | Nakahama et al. | | 2005/0261760 A1 | 11/2005 | Weber |
| 2005/0027350 A1 | 2/2005 | Momma et al. | | 2005/0266039 A1 | 12/2005 | Weber |
| 2005/0033411 A1 | 2/2005 | Wu et al. | | 2005/0266040 A1 | 12/2005 | Gerberding |
| 2005/0033412 A1 | 2/2005 | Wu et al. | | 2005/0267561 A1 | 12/2005 | Jones et al. |
| 2005/0033417 A1 | 2/2005 | Borges et al. | | 2005/0271706 A1 | 12/2005 | Anderson et al. |
| 2005/0037047 A1 | 2/2005 | Song | | 2005/0276837 A1 | 12/2005 | Anderson et al. |
| 2005/0038498 A1 | 2/2005 | Dubrow et al. | | 2005/0278016 A1 | 12/2005 | Welsh et al. |
| 2005/0042288 A1 | 2/2005 | Koblish et al. | | 2005/0278021 A1 | 12/2005 | Bates et al. |
| 2005/0055080 A1 | 3/2005 | Istephanous et al. | | 2005/0281863 A1 | 12/2005 | Anderson et al. |
| 2005/0055085 A1 | 3/2005 | Rivron et al. | | 2005/0285073 A1 | 12/2005 | Singh et al. |
| 2005/0060020 A1 | 3/2005 | Jenson | | 2005/0287188 A1 | 12/2005 | Anderson et al. |
| 2005/0060021 A1 | 3/2005 | O'Brien et al. | | 2006/0013850 A1 | 1/2006 | Domb |
| 2005/0069630 A1 | 3/2005 | Fox et al. | | 2006/0015175 A1 | 1/2006 | Palmaz et al. |
| 2005/0070989 A1 | 3/2005 | Lye et al. | | 2006/0015361 A1 | 1/2006 | Sattler et al. |
| 2005/0070990 A1 | 3/2005 | Stinson | | 2006/0020742 A1 | 1/2006 | Au et al. |
| 2005/0070996 A1 | 3/2005 | Dinh et al. | | 2006/0025848 A1 | 2/2006 | Weber et al. |
| 2005/0072544 A1 | 4/2005 | Palmaz et al. | | 2006/0034884 A1 | 2/2006 | Stenzel |
| 2005/0074479 A1 | 4/2005 | Weber et al. | | 2006/0035026 A1 | 2/2006 | Atanassoska et al. |
| 2005/0074545 A1 | 4/2005 | Thomas | | 2006/0038027 A1 | 2/2006 | O'Connor et al. |
| 2005/0077305 A1 | 4/2005 | Guevara | | 2006/0051397 A1 | 3/2006 | Maier et al. |
| 2005/0079199 A1 | 4/2005 | Heruth et al. | | 2006/0052744 A1 | 3/2006 | Weber |
| 2005/0079201 A1 | 4/2005 | Rathenow et al. | | 2006/0052863 A1 | 3/2006 | Harder et al. |
| 2005/0079356 A1 | 4/2005 | Rathenow et al. | | 2006/0052864 A1 | 3/2006 | Harder et al. |
| 2005/0087520 A1 | 4/2005 | Wang et al. | | 2006/0062820 A1 | 3/2006 | Gertner et al. |
| 2005/0092615 A1 | 5/2005 | Birdsall et al. | | 2006/0069427 A1 | 3/2006 | Savage et al. |
| 2005/0096731 A1 | 5/2005 | Looi et al. | | 2006/0075044 A1 | 4/2006 | Fox et al. |
| 2005/0100577 A1 | 5/2005 | Parker et al. | | 2006/0075092 A1 | 4/2006 | Kidokoro |
| 2005/0100609 A1 | 5/2005 | Claude | | 2006/0079863 A1 | 4/2006 | Burgmeier et al. |
| 2005/0102025 A1 | 5/2005 | Laroche et al. | | 2006/0085062 A1 | 4/2006 | Lee et al. |
| 2005/0106212 A1 | 5/2005 | Gertner et al. | | 2006/0085065 A1 | 4/2006 | Krause et al. |
| 2005/0107870 A1 | 5/2005 | Wang et al. | | 2006/0088561 A1 | 4/2006 | Eini et al. |
| 2005/0110214 A1 | 5/2005 | Shank et al. | | 2006/0088566 A1 | 4/2006 | Parsonage et al. |
| 2005/0113936 A1 | 5/2005 | Brustad et al. | | 2006/0088567 A1 | 4/2006 | Warner et al. |
| 2005/0119723 A1 | 6/2005 | Peacock | | 2006/0088666 A1 | 4/2006 | Kobrin et al. |
| 2005/0129727 A1 | 6/2005 | Weber et al. | | 2006/0093643 A1 | 5/2006 | Stenzel |
| 2005/0131509 A1 | 6/2005 | Atanassoska et al. | | 2006/0093646 A1 | 5/2006 | Cima et al. |
| 2005/0131521 A1 | 6/2005 | Marton | | 2006/0095123 A1 | 5/2006 | Flanagan |
| 2005/0131522 A1 | 6/2005 | Stinson et al. | | 2006/0100696 A1 | 5/2006 | Atanassoska et al. |
| 2005/0136090 A1 | 6/2005 | Falotico et al. | | 2006/0115512 A1 | 6/2006 | Peacock et al. |
| 2005/0137677 A1 | 6/2005 | Rush | | 2006/0121080 A1 | 6/2006 | Lye et al. |
| 2005/0137679 A1 | 6/2005 | Changelian et al. | | 2006/0122694 A1 | 6/2006 | Stinson et al. |
| 2005/0137684 A1 | 6/2005 | Changelian et al. | | 2006/0125144 A1 | 6/2006 | Weber et al. |
| 2005/0149102 A1 | 7/2005 | Radisch et al. | | 2006/0127442 A1 | 6/2006 | Helmus |
| 2005/0149170 A1 | 7/2005 | Tassel et al. | | 2006/0127443 A1 | 6/2006 | Helmus |
| 2005/0159804 A1 | 7/2005 | Lad et al. | | 2006/0129215 A1 | 6/2006 | Helmus et al. |
| 2005/0159805 A1 | 7/2005 | Weber et al. | | 2006/0129225 A1 | 6/2006 | Kopia et al. |
| 2005/0160600 A1 | 7/2005 | Bien et al. | | 2006/0136048 A1 | 6/2006 | Pacetti et al. |
| 2005/0163954 A1 | 7/2005 | Shaw | | 2006/0140867 A1 | 6/2006 | Helfer et al. |
| 2005/0165467 A1 | 7/2005 | Hunter et al. | | 2006/0141156 A1 | 6/2006 | Viel et al. |
| 2005/0165468 A1 | 7/2005 | Marton | | 2006/0142853 A1 | 6/2006 | Wang et al. |
| 2005/0165476 A1 | 7/2005 | Furst et al. | | 2006/0153729 A1 | 7/2006 | Stinson et al. |
| 2005/0171595 A1 | 8/2005 | Feldman et al. | | 2006/0155361 A1 | 7/2006 | Schomig et al. |
| 2005/0180919 A1 | 8/2005 | Tedeschi | | 2006/0167543 A1 | 7/2006 | Bailey et al. |
| 2005/0182478 A1 | 8/2005 | Holman et al. | | 2006/0171985 A1 | 8/2006 | Richard et al. |
| 2005/0186250 A1 | 8/2005 | Gertner et al. | | 2006/0178727 A1 | 8/2006 | Richter |
| 2005/0187608 A1 | 8/2005 | O'Hara | | 2006/0184235 A1 | 8/2006 | Rivron et al. |
| 2005/0192657 A1 | 9/2005 | Colen et al. | | 2006/0193886 A1 | 8/2006 | Owens et al. |
| 2005/0192664 A1 | 9/2005 | Eisert | | 2006/0193887 A1 | 8/2006 | Owens et al. |
| 2005/0196424 A1 | 9/2005 | Chappa | | 2006/0193888 A1 | 8/2006 | Lye et al. |
| 2005/0196518 A1 | 9/2005 | Stenzel | | 2006/0193889 A1 | 8/2006 | Spradlin et al. |
| 2005/0197687 A1 | 9/2005 | Molaei et al. | | 2006/0193890 A1 | 8/2006 | Owens et al. |
| 2005/0203606 A1 | 9/2005 | Vancamp | | 2006/0199876 A1 | 9/2006 | Troczynski et al. |
| 2005/0208098 A1 | 9/2005 | Castro et al. | | 2006/0200229 A1 | 9/2006 | Burgermeister et al. |
| 2005/0208100 A1 | 9/2005 | Weber et al. | | 2006/0200231 A1 | 9/2006 | O'Brien et al. |
| 2005/0209681 A1 | 9/2005 | Curcio et al. | | 2006/0210595 A1 | 9/2006 | Singhvi et al. |
| 2005/0211680 A1 | 9/2005 | Li et al. | | 2006/0212109 A1 | 9/2006 | Sirhan et al. |
| 2005/0214951 A1 | 9/2005 | Nahm et al. | | 2006/0222679 A1 | 10/2006 | Shanley et al. |
| 2005/0216074 A1 | 9/2005 | Sahatjian et al. | | 2006/0222844 A1 | 10/2006 | Stinson |
| 2005/0220853 A1 | 10/2005 | Dao et al. | | 2006/0224234 A1 | 10/2006 | Jayaraman |

| Publication No. | Date | Inventor |
|---|---|---|
| 2006/0229711 A1 | 10/2006 | Yan et al. |
| 2006/0229713 A1 | 10/2006 | Shanley et al. |
| 2006/0229715 A1 | 10/2006 | Istephanous et al. |
| 2006/0230476 A1 | 10/2006 | Atanasoska et al. |
| 2006/0233941 A1 | 10/2006 | Olson |
| 2006/0251701 A1 | 11/2006 | Lynn et al. |
| 2006/0263512 A1 | 11/2006 | Glocker |
| 2006/0263515 A1 | 11/2006 | Rieck et al. |
| 2006/0264138 A1 | 11/2006 | Sowinski et al. |
| 2006/0271169 A1 | 11/2006 | Lye et al. |
| 2006/0275554 A1 | 12/2006 | Zhao et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0276884 A1 | 12/2006 | Lye et al. |
| 2006/0276885 A1 | 12/2006 | Lye et al. |
| 2006/0276910 A1 | 12/2006 | Weber |
| 2006/0280770 A1 | 12/2006 | Hossainy et al. |
| 2006/0292388 A1 | 12/2006 | Palumbo et al. |
| 2007/0003589 A1 | 1/2007 | Astafieva et al. |
| 2007/0003817 A1 | 1/2007 | Umeda et al. |
| 2007/0032858 A1 | 2/2007 | Santos et al. |
| 2007/0032864 A1 | 2/2007 | Furst et al. |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0048452 A1 | 3/2007 | Feng et al. |
| 2007/0052497 A1 | 3/2007 | Tada |
| 2007/0055349 A1 | 3/2007 | Santos et al. |
| 2007/0055354 A1 | 3/2007 | Santos et al. |
| 2007/0059435 A1 | 3/2007 | Santos et al. |
| 2007/0065418 A1 | 3/2007 | Vallana et al. |
| 2007/0071789 A1 | 3/2007 | Pantelidis et al. |
| 2007/0072978 A1 | 3/2007 | Zoromski et al. |
| 2007/0073385 A1 | 3/2007 | Schaeffer et al. |
| 2007/0073390 A1 | 3/2007 | Lee |
| 2007/0106347 A1 | 5/2007 | Lin |
| 2007/0110888 A1 | 5/2007 | Radhakrishnan et al. |
| 2007/0112421 A1 | 5/2007 | O'Brien |
| 2007/0123973 A1 | 5/2007 | Roth et al. |
| 2007/0128245 A1 | 6/2007 | Rosenberg et al. |
| 2007/0129789 A1 | 6/2007 | Cottone et al. |
| 2007/0134288 A1 | 6/2007 | Parsonage et al. |
| 2007/0135908 A1 | 6/2007 | Zhao |
| 2007/0148251 A1 | 6/2007 | Hossainy et al. |
| 2007/0151093 A1 | 7/2007 | Curcio et al. |
| 2007/0154513 A1 | 7/2007 | Atanasoska et al. |
| 2007/0156231 A1 | 7/2007 | Weber |
| 2007/0173923 A1 | 7/2007 | Savage et al. |
| 2007/0181433 A1 | 8/2007 | Birdsall et al. |
| 2007/0190104 A1 | 8/2007 | Kamath et al. |
| 2007/0191923 A1 | 8/2007 | Weber et al. |
| 2007/0191928 A1 | 8/2007 | Rolando et al. |
| 2007/0191931 A1 | 8/2007 | Weber et al. |
| 2007/0191943 A1 | 8/2007 | Shrivastava et al. |
| 2007/0198081 A1 | 8/2007 | Castro et al. |
| 2007/0202466 A1 | 8/2007 | Schwarz et al. |
| 2007/0207186 A1 | 9/2007 | Scanlon et al. |
| 2007/0208412 A1 | 9/2007 | Elmaleh |
| 2007/0212547 A1 | 9/2007 | Fredrickson et al. |
| 2007/0213827 A1 | 9/2007 | Arramon |
| 2007/0219626 A1 | 9/2007 | Rolando et al. |
| 2007/0224116 A1 | 9/2007 | Chandrasekaran et al. |
| 2007/0224224 A1 | 9/2007 | Cordeira Da Silva et al. |
| 2007/0224235 A1 | 9/2007 | Tenney et al. |
| 2007/0224244 A1 | 9/2007 | Weber et al. |
| 2007/0244569 A1 | 10/2007 | Weber et al. |
| 2007/0254091 A1 | 11/2007 | Fredrickson et al. |
| 2007/0255392 A1 | 11/2007 | Johnson |
| 2007/0264303 A1 | 11/2007 | Atanasoska et al. |
| 2007/0269480 A1 | 11/2007 | Richard et al. |
| 2007/0299509 A1 | 12/2007 | Ding |
| 2008/0003251 A1 | 1/2008 | Zhou |
| 2008/0004691 A1 | 1/2008 | Weber et al. |
| 2008/0008654 A1 | 1/2008 | Clarke et al. |
| 2008/0038146 A1 | 2/2008 | Wachter et al. |
| 2008/0050413 A1 | 2/2008 | Horvers et al. |
| 2008/0050415 A1 | 2/2008 | Atanasoska et al. |
| 2008/0051881 A1 | 2/2008 | Feng et al. |
| 2008/0057103 A1 | 3/2008 | Roorda |
| 2008/0058921 A1 | 3/2008 | Lindquist |
| 2008/0069854 A1 | 3/2008 | Xiao et al. |
| 2008/0071348 A1 | 3/2008 | Boismier et al. |
| 2008/0071349 A1 | 3/2008 | Atanasoska et al. |
| 2008/0071350 A1 | 3/2008 | Stinson |
| 2008/0071351 A1 | 3/2008 | Flanagan et al. |
| 2008/0071352 A1 | 3/2008 | Weber et al. |
| 2008/0071353 A1 | 3/2008 | Weber et al. |
| 2008/0071355 A1 | 3/2008 | Weber et al. |
| 2008/0071358 A1 | 3/2008 | Weber et al. |
| 2008/0086199 A1 | 4/2008 | Dave et al. |
| 2008/0086201 A1 | 4/2008 | Weber et al. |
| 2008/0097577 A1 | 4/2008 | Atanasoska et al. |
| 2008/0107890 A1 | 5/2008 | Bureau et al. |
| 2008/0124373 A1 | 5/2008 | Xiao et al. |
| 2008/0140186 A1 | 6/2008 | Grignani et al. |
| 2008/0145400 A1 | 6/2008 | Weber et al. |
| 2008/0147177 A1* | 6/2008 | Scheuermann et al. ..... 623/1.42 |
| 2008/0152929 A1 | 6/2008 | Zhao |
| 2008/0160259 A1 | 7/2008 | Nielson et al. |
| 2008/0171929 A1 | 7/2008 | Katims |
| 2008/0188836 A1 | 8/2008 | Weber et al. |
| 2008/0241218 A1 | 10/2008 | McMorrow et al. |
| 2008/0243231 A1 | 10/2008 | Flanagan et al. |
| 2008/0243240 A1 | 10/2008 | Doty et al. |
| 2008/0249600 A1* | 10/2008 | Atanasoska et al. ........... 623/1.4 |
| 2008/0249615 A1 | 10/2008 | Weber |
| 2008/0255508 A1 | 10/2008 | Wang |
| 2008/0255657 A1 | 10/2008 | Gregorich et al. |
| 2008/0262607 A1 | 10/2008 | Fricke |
| 2008/0275543 A1 | 11/2008 | Lenz et al. |
| 2008/0288048 A1 | 11/2008 | Rolando et al. |
| 2008/0290467 A1 | 11/2008 | Shue et al. |
| 2008/0294236 A1 | 11/2008 | Anand et al. |
| 2008/0294246 A1 | 11/2008 | Scheuermann et al. |
| 2008/0306584 A1 | 12/2008 | Kramer-Brown |
| 2009/0012603 A1 | 1/2009 | Xu et al. |
| 2009/0018639 A1 | 1/2009 | Kuehling |
| 2009/0018642 A1 | 1/2009 | Benco |
| 2009/0018644 A1 | 1/2009 | Weber et al. |
| 2009/0018647 A1 | 1/2009 | Benco et al. |
| 2009/0028785 A1 | 1/2009 | Clarke |
| 2009/0030504 A1 | 1/2009 | Weber et al. |
| 2009/0076588 A1 | 3/2009 | Weber |
| 2009/0076595 A1 | 3/2009 | Lindquist et al. |
| 2009/0081450 A1 | 3/2009 | Ascher et al. |
| 2009/0112310 A1 | 4/2009 | Zhang |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118820 A1 | 5/2009 | Gregorich et al. |
| 2009/0118821 A1 | 5/2009 | Scheuermann et al. |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0138077 A1 | 5/2009 | Weber et al. |
| 2009/0149942 A1 | 6/2009 | Edelman et al. |
| 2009/0157165 A1 | 6/2009 | Miller et al. |
| 2009/0157166 A1 | 6/2009 | Singhal et al. |
| 2009/0157172 A1 | 6/2009 | Kokate et al. |
| 2009/0177273 A1 | 7/2009 | Piveteau et al. |
| 2009/0186068 A1 | 7/2009 | Miller et al. |
| 2009/0192593 A1 | 7/2009 | Meyer et al. |
| 2009/0202610 A1 | 8/2009 | Wilson |
| 2009/0208428 A1 | 8/2009 | Hill et al. |
| 2009/0220612 A1 | 9/2009 | Perera |
| 2009/0259300 A1 | 10/2009 | Dorogy, Jr. et al. |
| 2009/0264975 A1 | 10/2009 | Flanagan et al. |
| 2009/0281613 A1 | 11/2009 | Atanasoska et al. |
| 2009/0287301 A1 | 11/2009 | Weber |
| 2009/0306765 A1 | 12/2009 | Weber |
| 2009/0317766 A1 | 12/2009 | Heidenau et al. |
| 2010/0008970 A1 | 1/2010 | O'Brien et al. |
| 2010/0030326 A1 | 2/2010 | Radhakrishnan et al. |

| | | | | | | |
|---|---|---|---|---|---|---|
| 2010/0042206 | A1 | 2/2010 | Yadav et al. | CA | 2258898 | 1/2005 |
| 2010/0057197 | A1 | 3/2010 | Weber et al. | CA | 2308177 | 1/2005 |
| 2010/0070022 | A1 | 3/2010 | Kuehling | CA | 2475968 | 1/2005 |
| 2010/0070026 | A1 | 3/2010 | Ito et al. | CA | 2489668 | 6/2005 |
| 2010/0131050 | A1 | 5/2010 | Zhao | CA | 2490170 | 6/2005 |
| | | | | CA | 2474367 | 1/2006 |

FOREIGN PATENT DOCUMENTS

| | | | | | |
|---|---|---|---|---|---|
| AT | 288234 | 2/2005 | CA | 2374090 | 5/2007 |
| AU | 4825696 | 10/1996 | CA | 2282748 | 11/2007 |
| AU | 5588896 | 12/1996 | CA | 2336650 | 1/2008 |
| AU | 5266698 | 6/1998 | CA | 2304325 | 5/2008 |
| AU | 6663298 | 9/1998 | CN | 1430491 | 7/2003 |
| AU | 716005 | 2/2000 | CN | 1547490 | 11/2004 |
| AU | 5686499 | 3/2000 | CN | 1575154 | 2/2005 |
| AU | 2587100 | 5/2000 | CN | 1585627 | 2/2005 |
| AU | 2153600 | 6/2000 | CN | 1669537 | 9/2005 |
| AU | 1616201 | 5/2001 | DE | 3516411 | 11/1986 |
| AU | 2317701 | 8/2001 | DE | 19916086 | 10/1999 |
| AU | 5890401 | 12/2001 | DE | 19855421 | 5/2000 |
| AU | 3597401 | 6/2002 | DE | 19916315 | 9/2000 |
| AU | 2002353068 | 3/2003 | DE | 9422438 | 4/2002 |
| AU | 2002365875 | 6/2003 | DE | 1096902 | 5/2002 |
| AU | 2003220153 | 9/2003 | DE | 10064596 | 6/2002 |
| AU | 2003250913 | 1/2004 | DE | 10107339 | 9/2002 |
| AU | 2003249017 | 2/2004 | DE | 69712063 | 10/2002 |
| AU | 2003256499 | 2/2004 | DE | 10127011 | 12/2002 |
| AU | 2003272710 | 4/2004 | DE | 10150995 | 4/2003 |
| AU | 2003285195 | 6/2004 | DE | 69807634 | 5/2003 |
| AU | 2003287633 | 6/2004 | DE | 69431457 | 6/2003 |
| AU | 2003290675 | 6/2004 | DE | 10200387 | 8/2003 |
| AU | 2003290676 | 6/2004 | DE | 69719161 | 10/2003 |
| AU | 2003291470 | 6/2004 | DE | 02704283 | 4/2004 |
| AU | 2003295419 | 6/2004 | DE | 60106962 | 4/2005 |
| AU | 2003295535 | 6/2004 | DE | 60018318 | 12/2005 |
| AU | 2003295763 | 6/2004 | DE | 69732439 | 1/2006 |
| AU | 2004202073 | 6/2004 | DE | 69828798 | 1/2006 |
| AU | 2003300323 | 7/2004 | DE | 69830605 | 5/2006 |
| AU | 2004213021 | 9/2004 | DE | 102005010100 | 9/2006 |
| AU | 2003293557 | 1/2005 | DE | 602005001867 | 5/2008 |
| AU | 780539 | 3/2005 | DE | 69829015 | 3/2009 |
| BR | 8701135 | 1/1988 | DK | 914092 | 8/2002 |
| BR | 0207321 | 2/2004 | EP | 0129147 | 1/1990 |
| BR | 0016957 | 6/2004 | EP | 0734721 | 10/1996 |
| BR | 0316065 | 9/2005 | EP | 0650604 | 9/1998 |
| BR | 316102 | 9/2005 | EP | 0865762 | 9/1998 |
| CA | 1283505 | 4/1991 | EP | 0875217 | 11/1998 |
| CA | 2172187 | 10/1996 | EP | 0633840 | 11/1999 |
| CA | 2178541 | 12/1996 | EP | 0953320 | 11/1999 |
| CA | 2234787 | 10/1998 | EP | 0971644 | 1/2000 |
| CA | 2235031 | 10/1998 | EP | 0982041 | 3/2000 |
| CA | 2238837 | 2/1999 | EP | 1105169 | 6/2001 |
| CA | 2340652 | 3/2000 | EP | 1124594 | 8/2001 |
| CA | 2392006 | 5/2001 | EP | 1127582 | 8/2001 |
| CA | 2337565 | 8/2001 | EP | 1131127 | 9/2001 |
| CA | 2409862 | 11/2001 | EP | 1132058 | 9/2001 |
| CA | 2353197 | 1/2002 | EP | 1150738 | 11/2001 |
| CA | 2429356 | 8/2002 | EP | 1172074 | 1/2002 |
| CA | 2435306 | 8/2002 | EP | 1181943 | 2/2002 |
| CA | 2436241 | 8/2002 | EP | 0914092 | 4/2002 |
| CA | 2438095 | 8/2002 | EP | 0747069 | 9/2002 |
| CA | 2460334 | 3/2003 | EP | 0920342 | 9/2002 |
| CA | 2425665 | 4/2003 | EP | 1242130 | 9/2002 |
| CA | 2465704 | 4/2003 | EP | 0623354 | 10/2002 |
| CA | 2464906 | 5/2003 | EP | 0806211 | 10/2002 |
| CA | 2468677 | 6/2003 | EP | 1275352 | 1/2003 |
| CA | 2469744 | 6/2003 | EP | 0850604 | 2/2003 |
| CA | 2484383 | 1/2004 | EP | 1280512 | 2/2003 |
| CA | 2497602 | 4/2004 | EP | 1280568 | 2/2003 |
| CA | 2499976 | 4/2004 | EP | 1280569 | 2/2003 |
| CA | 2503625 | 5/2004 | EP | 1294309 | 3/2003 |
| CA | 2504524 | 5/2004 | EP | 0824900 | 4/2003 |
| CA | 2505576 | 5/2004 | EP | 1308179 | 5/2003 |
| CA | 2513721 | 5/2004 | EP | 1310242 | 5/2003 |
| CA | 2505080 | 6/2004 | EP | 1314405 | 5/2003 |
| CA | 2506622 | 6/2004 | EP | 1316323 | 6/2003 |
| CA | 2455670 | 7/2004 | EP | 1339448 | 9/2003 |
| CA | 2508247 | 7/2004 | EP | 1347791 | 10/2003 |
| CA | 2458172 | 8/2004 | EP | 1347792 | 10/2003 |
| CA | 2467797 | 11/2004 | EP | 1348402 | 10/2003 |
| | | | EP | 1348405 | 10/2003 |

| | | | | | | |
|---|---|---|---|---|---|---|
| EP | 1359864 | 11/2003 | | EP | 1561436 | 8/2007 |
| EP | 1365710 | 12/2003 | | EP | 1863408 | 12/2007 |
| EP | 1379290 | 1/2004 | | EP | 1071490 | 1/2008 |
| EP | 0902666 | 2/2004 | | EP | 1096902 | 1/2008 |
| EP | 1460972 | 2/2004 | | EP | 0895762 | 2/2008 |
| EP | 0815806 | 3/2004 | | EP | 0916317 | 2/2008 |
| EP | 1400219 | 3/2004 | | EP | 1891988 | 2/2008 |
| EP | 0950386 | 4/2004 | | EP | 1402849 | 4/2008 |
| EP | 1461165 | 4/2004 | | EP | 1466634 | 7/2008 |
| EP | 1416884 | 5/2004 | | EP | 1572032 | 7/2008 |
| EP | 1424957 | 6/2004 | | EP | 1527754 | 8/2008 |
| EP | 1429816 | 6/2004 | | EP | 1968662 | 9/2008 |
| EP | 1448116 | 8/2004 | | EP | 1980223 | 10/2008 |
| EP | 1448118 | 8/2004 | | EP | 1988943 | 11/2008 |
| EP | 1449545 | 8/2004 | | EP | 1490125 | 1/2009 |
| EP | 1449546 | 8/2004 | | EP | 1829626 | 2/2009 |
| EP | 1254674 | 9/2004 | | EP | 1229901 | 3/2009 |
| EP | 1453557 | 9/2004 | | EP | 1128785 | 4/2009 |
| EP | 1457214 | 9/2004 | | EP | 2051750 | 4/2009 |
| EP | 0975340 | 10/2004 | | EP | 1427353 | 5/2009 |
| EP | 1319416 | 11/2004 | | ES | 2169012 | 7/2002 |
| EP | 1476882 | 11/2004 | | FR | 2867059 | 9/2005 |
| EP | 1479402 | 11/2004 | | GB | 2397233 | 7/2004 |
| EP | 1482867 | 12/2004 | | JP | 3673973 | 2/1996 |
| EP | 1011529 | 1/2005 | | JP | 3249383 | 10/1996 |
| EP | 0875218 | 2/2005 | | JP | 3614652 | 11/1998 |
| EP | 1181903 | 2/2005 | | JP | 10295824 | 11/1998 |
| EP | 1504775 | 2/2005 | | JP | 11188109 | 7/1999 |
| EP | 1042997 | 3/2005 | | JP | 2000312721 | 11/2000 |
| EP | 1754684 | 3/2005 | | JP | 2001098308 | 4/2001 |
| EP | 1520594 | 4/2005 | | JP | 2001522640 | 11/2001 |
| EP | 1521603 | 4/2005 | | JP | 2002065862 | 3/2002 |
| EP | 1028672 | 6/2005 | | JP | 2002519139 | 7/2002 |
| EP | 1539041 | 6/2005 | | JP | 2002523147 | 7/2002 |
| EP | 1543798 | 6/2005 | | JP | 2003024449 | 1/2003 |
| EP | 1550472 | 6/2005 | | JP | 2003521274 | 7/2003 |
| EP | 1328213 | 7/2005 | | JP | 2003290361 | 10/2003 |
| EP | 1551569 | 7/2005 | | JP | 2003533333 | 11/2003 |
| EP | 1554992 | 7/2005 | | JP | 2004500925 | 1/2004 |
| EP | 1560613 | 8/2005 | | JP | 2004522559 | 7/2004 |
| EP | 1562519 | 8/2005 | | JP | 2004223264 | 8/2004 |
| EP | 1562654 | 8/2005 | | JP | 2004267750 | 9/2004 |
| EP | 1570808 | 9/2005 | | JP | 2004275748 | 10/2004 |
| EP | 1575631 | 9/2005 | | JP | 2004305753 | 11/2004 |
| EP | 1575638 | 9/2005 | | JP | 2005501654 | 1/2005 |
| EP | 1575642 | 9/2005 | | JP | 2005502426 | 1/2005 |
| EP | 0900059 | 10/2005 | | JP | 2005040584 | 2/2005 |
| EP | 1581147 | 10/2005 | | JP | 2005503184 | 2/2005 |
| EP | 1586286 | 10/2005 | | JP | 2005503240 | 2/2005 |
| EP | 1254673 | 11/2005 | | JP | 2005507285 | 3/2005 |
| EP | 1261297 | 11/2005 | | JP | 2005511139 | 4/2005 |
| EP | 0927006 | 1/2006 | | JP | 2005511242 | 4/2005 |
| EP | 1621603 | 2/2006 | | JP | 2005131364 | 5/2005 |
| EP | 1218665 | 5/2006 | | JP | 2005152526 | 6/2005 |
| EP | 1222941 | 5/2006 | | JP | 2005152527 | 6/2005 |
| EP | 1359867 | 5/2006 | | JP | 2005199054 | 7/2005 |
| EP | 1656961 | 5/2006 | | JP | 2005199058 | 7/2005 |
| EP | 1277449 | 6/2006 | | JP | 2008516726 | 5/2008 |
| EP | 0836839 | 7/2006 | | KR | 2002/0066996 | 8/2002 |
| EP | 1684817 | 8/2006 | | KR | 2004/0066409 | 7/2004 |
| EP | 1687042 | 8/2006 | | KR | 2005/0117361 | 12/2005 |
| EP | 0907339 | 11/2006 | | NZ | 331388 | 1/2000 |
| EP | 1359865 | 11/2006 | | SU | 393044 | 12/1973 |
| EP | 1214108 | 1/2007 | | WO | WO86/06617 | 11/1986 |
| EP | 1416885 | 1/2007 | | WO | WO93/06792 | 4/1993 |
| EP | 1441667 | 1/2007 | | WO | WO93/07934 | 4/1993 |
| EP | 1192957 | 2/2007 | | WO | WO93/16656 | 9/1993 |
| EP | 1236447 | 2/2007 | | WO | WO94/16646 | 8/1994 |
| EP | 1764116 | 3/2007 | | WO | WO95/03083 | 2/1995 |
| EP | 1185215 | 4/2007 | | WO | WO96/04952 | 2/1996 |
| EP | 1442757 | 4/2007 | | WO | WO96/09086 | 3/1996 |
| EP | 1786363 | 5/2007 | | WO | WO96/32907 | 10/1996 |
| EP | 1787602 | 5/2007 | | WO | WO97/41916 | 11/1997 |
| EP | 1788973 | 5/2007 | | WO | WO98/17331 | 4/1998 |
| EP | 1796754 | 6/2007 | | WO | WO98/18408 | 5/1998 |
| EP | 1330273 | 7/2007 | | WO | WO98/23228 | 6/1998 |
| EP | 0900060 | 8/2007 | | WO | WO98/36784 | 8/1998 |
| EP | 1355588 | 8/2007 | | WO | WO98/38946 | 9/1998 |
| EP | 1355589 | 8/2007 | | WO | WO98/38947 | 9/1998 |

| | | | | | | |
|---|---|---|---|---|---|---|
| WO | WO98/40033 | 9/1998 | | WO | WO2004/043300 | 5/2004 |
| WO | WO98/57680 | 12/1998 | | WO | WO2004/043509 | 5/2004 |
| WO | WO99/16386 | 4/1999 | | WO | WO2004/043511 | 5/2004 |
| WO | WO99/23977 | 5/1999 | | WO | WO2004/045464 | 6/2004 |
| WO | WO99/42631 | 8/1999 | | WO | WO2004/045668 | 6/2004 |
| WO | WO99/49928 | 10/1999 | | WO | WO2004/058100 | 7/2004 |
| WO | WO99/52471 | 10/1999 | | WO | WO2004/060428 | 7/2004 |
| WO | WO99/62432 | 12/1999 | | WO | WO2004/064911 | 8/2004 |
| WO | WO00/01322 | 1/2000 | | WO | WO2004/071548 | 8/2004 |
| WO | WO00/10622 | 3/2000 | | WO | WO2004/072104 | 8/2004 |
| WO | WO00/25841 | 5/2000 | | WO | WO2004/073768 | 9/2004 |
| WO | WO00/27303 | 5/2000 | | WO | WO2004/080579 | 9/2004 |
| WO | WO00/30710 | 6/2000 | | WO | WO2004/087251 | 10/2004 |
| WO | WO00/48660 | 8/2000 | | WO | WO2004/096176 | 11/2004 |
| WO | WO00/64506 | 11/2000 | | WO | WO2004/105639 | 12/2004 |
| WO | WO01/35928 | 5/2001 | | WO | WO2004/108021 | 12/2004 |
| WO | WO01/41827 | 6/2001 | | WO | WO2004/108186 | 12/2004 |
| WO | WO01/45862 | 6/2001 | | WO | WO2004/108346 | 12/2004 |
| WO | WO01/45763 | 7/2001 | | WO | WO2004/110302 | 12/2004 |
| WO | WO01/66036 | 9/2001 | | WO | WO2005/004754 | 1/2005 |
| WO | WO01/80920 | 11/2001 | | WO | WO2005/006325 | 1/2005 |
| WO | WO01/87263 | 11/2001 | | WO | WO2005/011529 | 2/2005 |
| WO | WO01/87342 | 11/2001 | | WO | WO2005/014892 | 2/2005 |
| WO | WO01/87374 | 11/2001 | | WO | WO2005/027794 | 3/2005 |
| WO | WO01/89417 | 11/2001 | | WO | WO2005/032456 | 4/2005 |
| WO | WO01/89420 | 11/2001 | | WO | WO2005/034806 | 4/2005 |
| WO | WO02/26162 | 4/2002 | | WO | WO2005/042049 | 5/2005 |
| WO | WO02/30487 | 4/2002 | | WO | WO2005/044361 | 5/2005 |
| WO | WO02/38827 | 5/2002 | | WO | WO2005/049520 | 6/2005 |
| WO | WO02/42521 | 5/2002 | | WO | WO2005/051450 | 6/2005 |
| WO | WO02/43796 | 6/2002 | | WO | WO2005/053766 | 6/2005 |
| WO | WO02/47581 | 6/2002 | | WO | WO2005/063318 | 7/2005 |
| WO | WO02/058753 | 8/2002 | | WO | WO2005/072437 | 8/2005 |
| WO | WO02/060349 | 8/2002 | | WO | WO2005/082277 | 9/2005 |
| WO | WO02/060350 | 8/2002 | | WO | WO2005/082283 | 9/2005 |
| WO | WO02/060506 | 8/2002 | | WO | WO2005/086733 | 9/2005 |
| WO | WO02/064019 | 8/2002 | | WO | WO2005/089825 | 9/2005 |
| WO | WO02/065947 | 8/2002 | | WO | WO2005/091834 | 10/2005 |
| WO | WO02/069848 | 9/2002 | | WO | WO2005/099621 | 10/2005 |
| WO | WO02/074431 | 9/2002 | | WO | WO2005/099626 | 10/2005 |
| WO | WO02/076525 | 10/2002 | | WO | WO2005/110285 | 11/2005 |
| WO | WO02/078668 | 10/2002 | | WO | WO2005/115276 | 12/2005 |
| WO | WO02/083039 | 10/2002 | | WO | WO2005/115496 | 12/2005 |
| WO | WO02/085253 | 10/2002 | | WO | WO2005/117752 | 12/2005 |
| WO | WO02/085424 | 10/2002 | | WO | WO2006/014969 | 2/2006 |
| WO | WO02/085532 | 10/2002 | | WO | WO2006/015161 | 2/2006 |
| WO | WO02/096389 | 12/2002 | | WO | WO2006/020742 | 2/2006 |
| WO | WO03/009779 | 2/2003 | | WO | WO2006/029364 | 3/2006 |
| WO | WO03/022178 | 3/2003 | | WO | WO2006/029708 | 3/2006 |
| WO | WO03/024357 | 3/2003 | | WO | WO2006/036801 | 4/2006 |
| WO | WO03/026713 | 4/2003 | | WO | WO2006/055237 | 5/2006 |
| WO | WO03/035131 | 5/2003 | | WO | WO2006/061598 | 6/2006 |
| WO | WO03/037220 | 5/2003 | | WO | WO2006/063157 | 6/2006 |
| WO | WO03/037221 | 5/2003 | | WO | WO2006/063158 | 6/2006 |
| WO | WO03/037223 | 5/2003 | | WO | WO2008/063539 | 6/2006 |
| WO | WO03/037398 | 5/2003 | | WO | 2006/083418 | 8/2006 |
| WO | WO03/039407 | 5/2003 | | WO | WO2006/083418 | 8/2006 |
| WO | WO03/045582 | 6/2003 | | WO | WO 2006083418 A2 * | 8/2006 |
| WO | WO03/047463 | 6/2003 | | WO | WO2006/104644 | 10/2006 |
| WO | WO03/051233 | 6/2003 | | WO | WO2006/104976 | 10/2006 |
| WO | WO03/055414 | 7/2003 | | WO | WO2006/105256 | 10/2006 |
| WO | WO03/061755 | 7/2003 | | WO | WO2006/107677 | 10/2006 |
| WO | WO03/072287 | 9/2003 | | WO | WO2006/116752 | 11/2006 |
| WO | WO03/077802 | 9/2003 | | WO | WO2006/124365 | 11/2006 |
| WO | WO03/083181 | 10/2003 | | WO | WO2007/016961 | 2/2007 |
| WO | WO03/094774 | 11/2003 | | WO | WO2007/034167 | 3/2007 |
| WO | WO2004/004602 | 1/2004 | | WO | WO2007/070666 | 6/2007 |
| WO | WO2004/004603 | 1/2004 | | WO | WO2007/095167 | 8/2007 |
| WO | WO2004/006491 | 1/2004 | | WO | WO2007/124137 | 11/2007 |
| WO | WO2004/006807 | 1/2004 | | WO | WO2007/126768 | 11/2007 |
| WO | WO2004/006976 | 1/2004 | | WO | WO2007/130786 | 11/2007 |
| WO | WO2004/006983 | 1/2004 | | WO | WO2007/133520 | 11/2007 |
| WO | WO2004/010900 | 2/2004 | | WO | WO2007/143433 | 12/2007 |
| WO | WO2004/014554 | 2/2004 | | WO | WO2007/145961 | 12/2007 |
| WO | WO2004/026177 | 4/2004 | | WO | WO2007/147246 | 12/2007 |
| WO | WO2004/028347 | 4/2004 | | WO | WO2008/002586 | 1/2008 |
| WO | WO2004/028587 | 4/2004 | | WO | WO2008/002778 | 1/2008 |
| WO | WO2004/043292 | 5/2004 | | WO | WO2008/024149 | 2/2008 |
| WO | WO2004/043298 | 5/2004 | | WO | WO2008/024477 | 2/2008 |

| | | |
|---|---|---|
| WO | WO2008/024669 | 2/2008 |
| WO | WO2008/033711 | 3/2008 |
| WO | WO2008/034048 | 3/2008 |
| WO | WO2008/036549 | 3/2008 |
| WO | WO2008/039319 | 4/2008 |
| WO | WO2008/045184 | 4/2008 |
| WO | WO2008/057991 | 5/2008 |
| WO | WO2008/061017 | 5/2008 |
| WO | WO2008/082698 | 7/2008 |
| WO | WO2008/106223 | 9/2008 |
| WO | WO2008/108987 | 9/2008 |
| WO | WO2008/124513 | 10/2008 |
| WO | WO2008/124519 | 10/2008 |
| WO | WO2008/140482 | 11/2008 |
| WO | WO2008/147848 | 12/2008 |
| WO | WO2008/147853 | 12/2008 |
| WO | WO2009/009627 | 1/2009 |
| WO | WO2009/009628 | 1/2009 |
| WO | WO2009/012353 | 1/2009 |
| WO | WO2009/014692 | 1/2009 |
| WO | WO2009/014696 | 1/2009 |
| WO | WO2009/020520 | 2/2009 |
| WO | WO2009/059081 | 5/2009 |
| WO | WO2009/059085 | 5/2009 |
| WO | WO2009/059086 | 5/2009 |
| WO | WO2009/059098 | 5/2009 |
| WO | WO2009/059129 | 5/2009 |
| WO | WO2009/059141 | 5/2009 |
| WO | WO2009/059146 | 5/2009 |
| WO | WO2009/059165 | 5/2009 |
| WO | WO2009/059166 | 5/2009 |
| WO | WO2009/059180 | 5/2009 |
| WO | WO2009/059196 | 5/2009 |
| WO | WO2009/089382 | 7/2009 |
| WO | WO2009/091384 | 7/2009 |
| WO | WO2009/094270 | 7/2009 |
| WO | WO2009/126766 | 10/2009 |
| ZA | 9710342 | 6/1998 |

OTHER PUBLICATIONS

Cho et al., "Preparation and Characterization of Iridium Oxide Thin Films Grown by DC Reactive Sputtering," *Jpn. J. Appl. Phys.*, 36(I)3B:1722-1727 (1997).
Glocker et al., "AC Reactive Sputtering with Inverted Cylindrical Magnetrons," Society of Vacuum Coaters, 43$^{rd}$ Annual Technical Conference Proceedings (Denver), p. 81 (Apr. 15-20, 2000).
Schetsky, L. McDonald, "Shape Memory Alloys," *Encyclopedia of Chemical Technology (3$^{rd}$ Edition)*, (John Wiley & Sons), 20:726-736 (1982).
Siegfried et al., "Reactive Cylindrical Magnetron Deposition of Titanium Nitride and Zirconium Nitride Films," Society of Facuum Coaters, 39$^{th}$ Annual Technical Conference Proceedings, p. 97-101 (1996).
Wessling et al., "RF-sputtering of Iridium Oxide to be Used as Stimulation Material in Functional Medical Implants," *J. Micromech. Microeng.*, 16:5142-5148 (2006).
U.S. Appl. No. 11/752,736, filed May 23, 2007, Shue et al.
Di Mario et al., "Moonlight: a controlled registry of an iridium oxide-coated stent with angographic follow-up," International Journal of Cardiology, vol. 95, pp. 329-331, (2004).
U.S. Appl. No. 11/694,436, filed Mar. 30, 2007, Atanasoska et al.
"Cyclic voltammetry"—from Wikipedia, (http://en.wikipedia.org/wiki/Cyclic_voltammetry) (downloaded [2007]).
"Electrophoretic deposition"—from Wikipedia, (http://en.wikipedia.org/wiki/electrophoretic_deposition) (downloaded [2007]).
"Impressive Progress in Interventional Cardiology—From 1st Balloon Inflation To First Bioabsorbable Stent," Medical News Today, May 15, 2006, (http://www.medicalnewstoday.com/articles/43313.php).
"JOMED Starts Clinical Studies on Tacrolimus-Eluting Coronary Stents," Jomed Press Release, 2 pages, Jan. 14, 2002.
"Nano PLD" PVD Products, Inc. Wilmington, MA, (2003).
"Sputtering," Wikipedia.com, (http://en.wikipedia.org/wiki/Sputtering) (downloaded [2009]).

"Ultraviolet-Ozone Surface Treatment," Three Bond Technical News #17, pp. 1-10, Issued Mar. 20, 1987, (http://www.threebond.co.jp/en/technical/technicalnews/pdf/tech17.pdf).
Abbott et al., "Voltammetric and impedance studies of the electropolishing of type 316 stainless steel in a choline chloride based ionic liquid," Electrochimica Acta, vol. 51, pp. 4420-4425, (2006).
Adanur et al., "Nanocomposite Fiber Based Web and Membrane Formation and Characterization," Journal of Industrial Textiles, vol. 36, No. 4, pp. 311-327, Apr. 2007.
Advincula et al., "Surface modification of surface sol-gel derived titanium oxide films by self-assembled monolayers (SAMs) and non-specific protein adsorption studies," Colloids and Surfaces B: Biointerfaces, vol. 42, pp. 29-43, (2005).
Akhras, "Bare metal stent, lunar IrOx2 coated or drug-eluting stent for patients with CAD?", PowerPoint presentation, Oct. 2006.
Akhras, Comparison of Iridiumoxide Coated Stent with Paclitaxel-Eluting Stent and a Bare Metal Stent in Patients With Coronary Artery Disease; Abstract, Oct. 2006.
Al-Lamee, "Programmable Elution Profile Coating for Drug-Eluting Stents," Medical Device Technology: Materials, pp. 12-15, Mar. 2005.
Amanatides et al., "Electrical and optical properties of $CH_4/H_2$ RF plasmas for diamond-like thin film deposition," Diamond & Related materials, vol. 14, pp. 292-295, (2005).
Amberg et al., "Silver Deposition on Temperature Sensitive Substrates by Means of an Inverted Cylindrical Magnetron," Poster, 2003.
Anders, "Ion Plating and Beyond: Pushing the Limits of Energetic Deposition," Vacuum Technology & Coating, pp. 41-46, Dec. 2002.
Andersson et al., "Influence of Systematically Varied Nanoscale Topography on the Morphology of Epithelial Cells," IEEE Transactions on Nanobioscience, vol. 2, No. 2, pp. 49-57, Jun. 2003.
Andersson et al., "Nanoscale features influence epithelial cell morphology and cytokine production," Biomaterials, 2003. vol. 24, No. 20, pp. 3427-3436, (2003).
Annis et al., "An Elastomeric Vascular Prosthesis," Transactions—American Society for Artificial Internal Organs. vol. XXIV, pp. 209-214, (1978).
Ansell et al., "X-Ray Rhotoelectron Spectroscopic Studies of Tin Electrodes after Polarization in Sodium Hydroxide Solution," Journal of Electrochemical Society: Electrochemical Science and Technology, vol. 124, No. 9, pp. 1360-1364, Sep. 1977.
Antunes et al., "Characterization of Corrosion Products Formed on Steels in the First Months of Atmospheric Exposure", Materia, vol. 8, No. 1, pp. 27-34, (2003).
Armani et al., "Microfabrication Technology for Polycaprolactone, a Biodegradable Polymer," Journal of Micromechanics and Microengineering, vol. 10, pp. 80-84, (2000).
Arnold et al., "Activation of Integrin Function by Nanopatterned Adhesive Interface," ChemPhysChem, vol. 5, pp. 383-388, (2004).
Ashfold et al., "Pulsed laser ablation and deposition of thin films," Chem. Soc. Rev., vol. 33, pp. 23-31, (2004).
Asoh et al., "Conditions for Fabrication of Ideally Ordered Anodic Porous Alumina Using Pretextured Al," Journal of The Electrochemical Society, vol. 148, pp. B152-B156, (2001).
Atanasoska et al., "XPS Studies on Conducting Polymers: Polypyrrole Films Doped with Perchlorate and Polymeric Anions," Chemistry Materials vol. 4, pp. 988-994, (1992).
Aughenbaugh et al., "Silica sol-gel for the controlled release of antibiotics. II. The effect of synthesis parameters on the in vitro release kinetics of vancomycin," Journal of Biomedical Materials Research, vol. 57, No. 3, pp. 321-326, Dec. 5, 2001.
Awad et al., "Deposition of duplex $Al_2O_3$/TiN coatings on aluminum alloys for tribological applications using a combined microplasma oxidation (MPO) and arc ion plating (AIP)," Wear, vol. 260, pp. 215-222, (2006).
AxynTec product review, AxynTec Dunnschichttechnik GmbH (www.axyntec.de) (2002).
Ayon et al., "Drug loading of nonopouros $TiO_2$ films," Institute of Physics Publishing, Biomedical Materials, vol. 1, pp. L11-L15, (2006).

Azom, "Porous Coatings for Improved Implant Life—Total Hip Replacements," [downloaded Sep. 1, 2005], (http://www.azom.com/Details.asp?ArticleID=1900).

Bak et al., "Electrodeposition of polymer next to the three-phase boundary," Electrochemisty Communications, vol. 7, pp. 1098-1104, (2005).

Balamuguran et al., "Bioactive Sol-Gel Hydroxyapatite Surface for Biomedical Applications—In Vitro Study," Trends in Biomaterials & Artificial Organs, vol. 16, No. 1, pp. 18-20, (2002).

Balas et al., "Formation of Bone-Like Apatite on Organic Polymers Treated with a Silane-Coupling Agent and a Titania Solution," Biomaterials, vol. 27, pp. 1704-1710, (2006).

Balaur et al., "Tailoring the wettability of $TiO_2$ nanotube layers," Electrochemistry Communications, vol. 7, pp. 1066-1070, (2005).

Banks et al., "Femtosecond Laser-Induced Forward Transfer (LIFT): A Technique for Versatile Micro-Printing Applications," European Conference on Lasers and Electro-Optics and the International Quantum Electronics Conference, Jun. 17-22, 2007.

Banks et al., "Nano-droplets Deposited in Microarrays by Femtosecond Ti:Saphire Laser-Induced Forward Transfer," Optoelectronics Reaserch Centre, University of Southhampton, Applied Physics Letters, vol. 89, Issue 19, (2006).

Barbucci et al, Micro and nano-structured surfaces,: Journal Of Materials Science: Materials In Medicine, vol. 14, No. 8, pp. 721-725, (2003).

Bates et al. "Description of research activites: Block copolymers," Organization for Minnesota Nanotechnology Institute, University of Minnesota, (2002).

Bayoumi et al., "Formation of self-organized titania nano-tubes by dealloying and anodic oxidation," Electrochemistry Communications, vol. 8, pp. 38-44, (2006).

Békési et al., "Efficient Submicron Processing of Metals with Femtosecond UV Pulses," Applied Physics A, vol. 76, pp. 355-357 (2003).

Benson, "Drug Delivery Technology and Access," Polygenetics, Inc., pp. 1-10, Oct. 2005.

Benson, "Highly Porous Polymers," American Laboratory, pp. 1-14, Apr. 2003.

Berg et al., "Controlled Drug Release from Porous Polyelectrolyte Multilayers," Biomacromolecules, vol. 7, pp. 357-364, (2006).

Berkland et al., "Controlling surface nano-structure using flow-limited field-injection electrostatic spraying (FFESS) of poly(D,L-lactide-co-glycolide)," Biomaterials, vol. 25, pp. 5649-5658, (2004).

Belly et al., "The fibroblast response to tubes exhibiting internal nanotopography," Biomaterials, vol. 26, No. 24, pp. 4985-4992, (2005).

Biederman et al. "Plasma Polymer-Metal Composite Films," Plasma Deposition, Treatment and Etching of Polymers, pp. 269-320, (1990).

Bock et al., "Anion and water involvement in hydrous Ir oxide redox reactions in acidic solutions," Journal of Electroanalytical Chemistry, vol. 475, pp. 20-27, (1999).

Bolle et al., "Characterization of submicrometer periodic structures produced on polymer surfaces with low-fluence ultraviolet laser radiation," Journal of Applied Physics, vol. 73, No. 7, pp. 3516-3524, Apr. 1, 1993.

Bolzán et al., "The Potentiodynamic behaviour of iridium electrodes in aqueous 3.7 M $H_2SO_4$ in the 293-195 K Range," Journal of Electroanalytical Chemistry, vol. 461, pp. 40-51, (1999).

Boulmedais et la., "Controlled Electrodissolution of Polyelectrolyte Multilayers: A Platform Technology Towards the Surface-Initiated Delivery of Drugs," Advanced Functional Materials, vol. 63, pp. 63-70, (2006).

Boura et al., "Endothelial cell—interactions with polyelectrolyte multilayer films," Biomaterials, vol. 26. pp. 4568-4575, (2005).

Bradley et al., "Visuotopic Mapping Through a Multichannel Stimulating Implant in Primate V1," Journal of Neurophysiology, vol. 93, pp. 1659-1670, (2005).

Bretagnol et al., "Functional Micropatterning Surface by Combination of Plasma Polymerization and Lift-Off Process," Plasma Process and Polymers, vol. 3, pp. 30-38, Nov. 14, 2005.

Bretagnol et al., "Surface Functionalization and Patterning Techniques to Design Interfaces for Biomedical and Biosensor Applications," Plasma Processes and Polymers, vol. 3, pp. 443-455, (2006).

Brody et al., "Characterization Nanoscale topography of the Aortic Heart Valve Basement Membrane for Tissue Engineering Heart Valve Scaffold Design," Tissue Engineering, vol. 12, No. 2, pp. 413-421, Nov. 2, 2006.

Brukner et al., "Metal plasma immersion ion implantation and deposition (MPIIID): chromium on magnesium," Surface and Coatings Technology vol. 103-104, pp. 227-230, (1998).

Brunetti et al., "Oxide/hydroxide films on tin. Part I: Kinetic aspects of the electroformation and electroreductions of the films," Journal of Electroanalytical Chemisty, (2007).

Bu et al., "Synthesis of $TiO_2$ Porous Thin Films by Polyethylene Glycol Templating and Chemistry of the Process," Journal of the European Ceramic Society, vol. 25, pp. 673-679 (2005).

Burmeister et al., "Colloid Monolayers as Versatile Lithographic Masks," Langmuir, vol. 13, pp. 2983-2987, (1997).

Buster et al., "Crystal habits of the Magnesium Hydroxide mineral Brucite within Coral Skeletons," American Geophysical Union Annual Meeting, Abstract and Poster, (2006).

Buttiglieri et al., "Endothelization and adherence of leucocytes to nanostructured surfaces," Biomaterials, vol. 24, pp. 2731-2738, (2003).

Calcagno et al., "Structural modification of polymer films by ion irradiation," Nuclear Instruments and Methods in Physics Research, vol. B65, pp. 413-422, (1992).

Carp et al., "Photoinduced Reactivity of Titanium Dioxide," Progress in Solid State Chemistry, vol. 32, pp. 33-177, (2004).

Caruso, "Nanoscale Particle Modifications via Sequential Electrostatic Assembly," Colloids and Colloid Assemblies: Synthesis, Modification, Organization and Utilization of Colloid Particles, pp. 266-269, Mar. 19, 2004.

Cassak, "ART: Bucking the Trend in Bioabsorbable Stents", Windhover Information Inc., In Vivo Jun. 2008.

Catledge et al, "Structure and Mechanical Properties of Functionally-Graded Nanostructured Metalloceramic Coatings," Mat. Res. Soc. Symp. Proc. vol. 778, pp. U7.8.1-U7.8.6, (2003).

Catledge et al., "Structural and mechanical properties of nanostructured metalloceramic coatings on cobalt chrome alloys," Applied Physics Letters, vol. 82, No. 10, pp. 1625-1627, Mar. 10, 2003.

Caves et al., "The evolving impact of microfabrication and nanotechnology on stent design," Journal of Vascular Surgery, pp. 1363-1368, Dec. 2006.

Caves et al., "The evolving impact of microfabrication and nanotechnology on stent design," Journal of Vascular Surgury, vol. 44, pp. 1363-1368, (2006).

Cernigoj et al., "Photocatalytically Active TiO2 Thin Films Produced by Surfactant-Assistant Sol-Gel Processing," Thin Solid Films, vol. 495, pp. 327-332, (2006).

Ceruti et al., "Preparation, characterization, cytotoxicity and pharmacokinetics of liposomes containing water-soluble prodrugs of paclitaxel," Journal of Controlled Release, vol. 63, pp. 141-153, (2000).

Champagne et al., "Nanometer-scale scanning sensors fabricated using stencil lithography," Applied Physics Letters, vol. 82, No. 7, pp. 1111-1113, Feb. 17, 2003.

Chandra et al., "Biodegradable Polymers," Progress in Polymer Science, vol. 23, pp. 1273-1335, (1998).

Chang et al., "Preparation and Characterization of Nanostructured Tin Oxide Films by Electrochemical Deposition," Electrochemical and Solid-State Letters, vol. 5, No. 8, pp. C71-C74, (2002).

Chen et al., "Blood compatiblity and $sp^3/sp^2$ contents of diamond-like carbon (DLC) synthesized by plasma immersion ion implantation-deposition," Surface and Coatings Technology, vol. 156, pp. 289-294, (2002).

Chen et al., "Fabrication of micro-field emitters on ceramic substrates," Microelectronic Engineering, vol. 84, pp. 94-100, (2007).

Chen et al., "Behavior of Cultured Human Umbilical Vein Endothelial Cells on Titanium Oxie Films Fabricated by Plasma Immersion Ion Implantation and Deposition," Surface & Coatings Technology, vol. 186, pp. 270-276, (2004).

Cheng et al., "Anatase Coating on NiTi Via a Low-Temperature Sol-Gel Route for Improving Corrosion Resistance," Scripta Materialia, vol. 51, pp. 1041-1045, (2004).

Cho et al., "A Novel Route to Three-Dimensionally Ordered Macroporous Polymers by Electron Irradiation of Polymer Colloids" Advanced Materials, vol. 17, No. 1, pp. 120-125, Jan. 6, 2005.

Cho et al., "Influence of Silica on Shape Memory Effect and Mechanical Properties of Polyurethane-Silica Hybrid," European Polymer Journal, vol. 40, pp. 1343-1348, (2004).

Cho et al., "Preparation and Characterization of Iridium Oxide Thin Films Grown by DC Reactive Sputtering," Japanese Journal of Applied Physics, vol. 36, Part 1, No. 3B, pp. 1722-1727, Mar. 1997.

Choi et al., "Synthesis and Characterization of Diamond-Like Carbon Protective AR Coating," Journal of the Korean Physical Society, vol. 45, p. S864, Dec. 2004.

Chougnet et al., "Substrates do influence the ordering of mesoporous thin films," Journal of Materials Chemistry, vol. 15, pp. 3340-3345, (2005).

Chougnet et al., "The Influence of the Nature of the Substrate on the Ordering of Mesoporous Thin Films," Thin Solid Films, vol. 495, pp. 40-44, (2006).

Chow et al., "Nanostructured Films and Coating by Evaporation, Sputtering, Thermal Spraying, Electro and Electroless Deposition," Handbook of Nanophase and Nanostructured Materials, vol. 1, Chapter 9, pp. 246-272, (2003).

Chow et al., "Preliminary Evaluation of Kem for Fabrication," Proceedings of the 12th General Meeting of JOWOG 31, Livermore, CA, University of California, (1996).

Chronakis, "Novel nanocomposites and nanoceramics based on polymer nanofibers using electrospinning process—a review," Journal of Materials Processing Technology, vol. 167, pp. 283-293, (2005).

Chu, "Recent developments and applications of plasma immersion ion implantation," Journal of Vacuum Science Technology, vol. B22, No. 1, pp. 289-296, Jan./Feb. 2004.

Chuang et al., "Titanium Oxide and Polyaniline Core-Shell Nanocomposites," Synthetic Metals, vol. 152, pp. 361-364, (2005).

Chung et al., "Roles of discontinuities in bio-inspired adhesive pads," Journal of The Rolyal Society: Interface, vol. 2, pp. 55-61, Feb. 8, 2005.

Clark, "Micropatterning Cell Adhesiveness", Immobilized Biomolecules in Analysis, Oxford University Press, pp. 95-111, (1998).

Clevy et al., "Micromanipulation and Micro-Assembly Systems," IEEE/RAS International Advanced Robotics Program, IARP'06, Paris, France, (2006).

Colina et al., "Dna deposition through laser induced forward transfer," Biosensors and Bioelectronics, vol. 20, pp. 1638-1642, (2005).

Costanzo et al., "Model-Based Simulations to Engineer Nanoporous Thin Films," LPCM Research, Pennsylvania State University, (2004), (http://lpcm.esm.psu.edu/~tjy107/research.htm).

Course: C-103, "An Introduction to Physical Vapor Deposition (PVD) Processes," Society of Vacuum Coaters, SVC Education Programs: course description and syllabus, Apr. 19, 2008.

Course: C-208, "Sputter Deposition in Manufacturing" Society of Vacuum Coaters, SVC Education Programs: course description and syllabus, Apr. 22, 2008.

Csete et al., "The existence of sub-micrometer micromechanical modulation generated by polarized UV laser illumination on polymer surfaces," Materials Science and Engineering C, vol. 23, pp. 939-944, (2003).

Csete et al., "The role of original surface roughness in laser-induced periodic surface structure formation process on poly-carbonate films," Thin Solid Films, vol. 453-454, pp. 114-120, (2004).

Curtis et al. "Cells react to nanoscale order and symmetry in their surroundings," IEEE Transactions on Nanobioscience, vol. 3, No. 1, pp. 61-65, Mar. 2004.

Curtis et al., "Nantotechniques and approaches in biotechnology," Trends in Biotechnology, vol. 19, No. 3, pp. 97-101, Mar. 2001.

Curtis et al., "New Depths in Cell Behaviour: Reactions of Cells to Nanotopography," Biochem, Soc, Symp, vol. 65, pp. 15-26, (1999).

Curtis et al., "New depths in cell behaviour: Reactions of cells to nanotopography," Biochemical Society Symposium, No. 65, pp. 15-26 (1997).

Curtis et al., "Topographical Controls of Cells," Biomaterials, vol. 18, pp. 1573-1583, (1997).

Curtis, "Tutorial on the biology of nanotopography," IEEE Transactions on Nanobioscience, vol. 3, No. 4, pp. 293-295, Dec. 2004.

Cyster et al., "The effect of surface chemistry and nanotopography of titanium nitride (TiN) films on 3T3-L1 fibroblasts," Journal of Biomedical Materials Research: A., vol. 67, No. 1, pp. 138-147, Oct. 2003.

Cyster et al., "The effect of surface chemistry and nanotopography of titanium nitride (TiN) films on primary hippocampal neurones," Biomaterials, vol. 25, pp. 97-107, (2004).

da Cruz et al., "Preparation, structure and electrochemistry of a polypyrrole hybrid film with $[Pd(dmit)_2]^{2-}$, bis(1,3-dithiole-2-thione-4,5-dithiolate)palladate(II)," Electrochimica Acta, vol. 52, pp. 1899-1909, (2007).

Dalby et al., "In vitro reaction of endothelial cells to polymer demixed nanotopography," Biomaterials, vol. 23, No. 14, pp. 2945-2954, (2002).

Dalby, "Topographically induced direct cell mechanotransduction," Medical Engineering & Physics, vol. 27, No. 9, pp. 730-742, (2005).

Damen et al., "Paclitaxel Esters of Malic Acid as Prodrugs with Improved Water Solubility," Bioorganic & Medicinal Chemistry, vol. 8, pp. 427-432, (2000).

D'Aquino, "Good Drug Therapy: It's Not Just the Molecule—It's the Delivery," CEP Magazine, (www.cepmagazine.org), 3 pages, Feb. 2004.

Datta et al., "Fundamental aspects and applicatio of electrochemical microfabrication," Electrochimica Acta, vol. 45, pp. 2535-2558, (2000).

Daxini et al., "Micropatterned polymer surface inprove retention of endothelial cells exposed to flow-induced shear stress," Biorheology, vol. 43, pp. 45-55, (2006).

De Aza et al., "Crack growth resistance of alumina, zirconia and zirconia toughened alumina ceramics for joint prostheses," Biomaterials, vol. 23, No. 3, pp. 937-945, Feb. 2002.

Deakin et al., "De-alloying of type 316 stainless steel in hot, concentrated sodium hydroxide solution," Corrosion Science, vol. 46, pp. 2117-2133, (2004).

Debiotech, "Debiostar, An Innovative Solution for Sustained Drug Delivery," Copyright 2001, (http://www.debiotech.com/products/drugdd/stent_page_1.html).

Debiotech, "Debiostent: An Innovatice Ceramic Coating for Implantable Medical Devices," [first downloaded on Sep. 1, 2005], (http://www.debiotech.com/products/drugdd/stent_page_1.html).

Debiotech, "Debiostent: Polymer free drug eluting coating," Jun. 14, 2007, (www.debiotech.com/products/dmggd/stent_page_1.html).

Debiotech, "Debiotech Obtains Exclusive Rights to an Innovative Drug Eluting Stent Technology," Press release, 1 page, Mar. 7, 2003.

Demisse, "Computational Investigation of Conducting Polythiophenes and Substituted Polythiophenes," A Thesis Submitted to the School of Graduate Studies of Addis Ababa University, Ethiopia, Jun. 2007.

Deniau et al., "Study of the polymers obtained by electroreduction of methacrylonitrile," Journal of Electroanalytical Chemistry, vol. 505, pp. 33-43, (2001).

Desai et al., "Characterization of micromachined silicon membranes for imrnunoisolation and bioseparation applications," Journal of Membrane Science, vol. 159, pp. 221-231, (1999).

Desai et al., "Use of Microfabricated 'Nanopore' Membranes as a Rate-Limiting Barrier to Diffusion of Small and Large Molecules: Possible Role in Drug Delivery" BioMEMs and Nanotechnology World, (2001).

Desai, Integrating Cells with Microsystems: Application in Tissue Engineering and Cell-Based Delivery, PowerPoint presentation, May 10, 2002.

Di Mario et al., "Drug-eluting bioabsorbable magnesium stent," Journal of Interventional Cardiology, vol. 17, Issue 6, Dec. 2004.

Di Mario et al., "Moonlight: a controlled registry of an iridium oxide-coated stent with angographic follow-up," International Journal of Cardiology, vol. 95, pp. 329-331, (2004).

Di Mario, The Moonlight Study: Multicenter Objective Observational Lunar Iridium Oxide Intimal Growth Trial, PowerPoint presentation in 2002.

Dibra et al., "Influence of the stent surface topology on the outcomes of patients undergoing coronary stenting: a randomized double-blind controlled trial", Catheterization and Cardiovascular Interventions, vol. 65, pp. 374-380, (2005).

Dittmar et al., "Nanostructured Smart Drug Delivery Coatings," European Cells and Materials, vol. 31, Supplinment 2, p. 73, (2007).

Dong et al., "Preparation of Submicron Polypyrrole/Poly(methly methacrylate) Coaxial Fibers and conversion to Polypyrrole Tubes and Carbon Tubes," Langmuir, vol. 22, pp. 11384-11387, (2006).

Doraiswamy et al., "Excimer laser forward transfer of mammalian cells using a novel triazene absorbing layer," Applied Surface Science, vol. 252, pp. 4743-4747, (2006).

DTI Technology Group: Materials-Coating, "Kinetic spray coating method," www.delphi.com, Jul. 2004.

Dumas et al., "Characterization of magnesium fluoride thin films produced by argon ion beam-assisted deposition," Thin Solid Films, vol. 382, pp. 61-68, (2001).

Duncan et al., "Polymer-drug conjugates, PDEPT and PELT: basic principals for design and transfer from laboratory to clinic," Journal of Controlled Release, vol. 74, pp. 135-146, (2001).

Duncan, "The Dawning Era of Polymer Therapeutics," Nature Reviews: Drug Discovery, vol. 2, pp. 347-360, May 2003.

Dutta et al., "Self-Organization of Colloidal Nanoparticles," Encyclopedia of Nanoscience and Nanotechnology, vol. 9, pp. 617-640, (2003).

Duwez et al., "Mechanochemistry: targeted delivery of single molecules," Nature Nanotechnology, vol. 1, pp. 122-125, (2006).

EAG Technical Note, "Functional Sites on Non-polymeric Materials: Gas Plasma Treatment and Surface Analysis," Evans Analytical Group, (2003).

Eberli et al., "The Lunar Coronary Stent System," Handbook of coronary stents, 4th edition, Chapter 17 (Martin Dunitz Ltd 2002).

Eesley et al., "Thermal properties of kinetics spray A1-SiC metal-matrix composite," Journal of Materials Research, vol. 18, No. 4, pp. 855-860, Apr. 2003.

Egerhazi et al., "Thickness distribution of carbon nitride films grown by inverse-pulsed laster deposition," Applied Surface Science, vol. 247, pp. 182-187, (2005).

Electropolymerization, (http://intel.ucc.ie/sensors/Electropolym.htm) (downloaded [2007]).

Eriebacher et al., "Evolution of nonoporosity in dealloying," Nature, vol. 410, pp. 450-453, Mar. 22, 2001.

Erlebacher et al., "Evolution of nanoporosity in dealloying," *Nature*, vol. 410, pp. 450-453, Mar. 22, 2001.

Esrom et al., "New approach of a laser-induced forward transfer for deposition of patterned thin metal films," Applied Surface Science, vol. 86, pp. 202-207, (1995).

Faupel et al., "Microstructure of pulsed laser deposited ceramic-metal and polymer-metal nanocomposite thin films," Applied Physics A, vol. 79, pp. 1233-1235 (2004).

Faust et al., "Biofunctionalised Biocompatible Titania Coatings for Implants," Euro Ceramics VII, Key Engineering Materials, vol. 206, No. 2, pp. 1547-1550, (2006).

Fernandez-Pradas et al., "Laser-induced forward transfer of biomolecules," Thin Solid Films, vol. 453-454, pp. 27-30, (2004).

Ferraz et al., "Influence of nanoporesize on platelet adhesion and activation," Journal of Materials Science: Materials in Medicine, vol. 19, pp. 3115-3121, (2008).

Figallo et al., "Micropatterned Biopolymer 3D Scaffold for Static and Dynamic Culture of Human Fibroblasts," Biotechnology Progress, vol. 23, pp. 210-216, (2007).

Flemming et al., "Effects of synthetic micro- and nano-structured surfaces on cell behavior," Biomaterials, vol. 20, No. 6, pp. 573-588, (1999).

Flemming et al., "Effects of synthetic micro-and nano-structured surfaces on cell behavior," Biomaterials, vol. 20, pp. 573-588, (1999).

Fogarassy et al., "Laser-induced forward transfer: A new approach for the deposition of high $T_c$ superconducting thin films," Journal of Materials Research, vol. 4, No. 5, pp. 1082-1086, Sep./Oct. 1989.

Fonseca et al., "Paclitaxel-loaded PLGA nanoparticles: preparation, physicochemical characterization and in vitro anti-tumoral activity," Journal of Controlled Release, vol. 83 pp. 273-286, (2002).

Forty, "Corrosion micromorphology of noble metal alloys and depletion gilding," Nature, vol. 282, pp. 597-598, Dec. 6, 1979.

Frechet, "Functional Polymers: from Plastic Electronics to Polymer-Assisted Therapeutics," Progress in Polymer Science, vol. 30, pp. 844-857, (2005).

Free Online Dictionary, "Aperture," definition, [first viewed Oct. 9, 2009].

Freitas et al., "Nimesulide PLA microsphere as a potential sustained release system for the treatment of inflammatory diseases," International Journal of Pharmaceutics, Vo. 295, pp. 201-211, (2005).

Freitas, "Nanomedicine, vol. I: Basic Capabilities," Landes Bioscience, pp. 87, 90, 255 and 265, (1999).

Friedrich et al., "Developing Interdisciplinary Undergraduate and Graduate Courses Through the Integration of Recent Research Results into the Curricula," (http://www.ineer.org/Events/ICEE1997/Proceedings/paper326.htm), 10 pages, [first downloaded Mar. 10, 2005.].

Fu et al., "Effects of mesh-assisted carbon plasma immersion ion implantation on the surface propoerties of insulating silicon carbide ceramics," Journal of Vacuum Science Technology, vol. A22, No. 2, pp. 356-360, Mar./Apr. 2004.

Fu et al., "Influence of thickness and dielectric properties on implantation efficacy in plasma immersion ion implantation of insulators," Journal of Applied Physics, vol. 95, No. 7, pp. 33193323, Apr. 1, 2004.

Fujisawa et al., "A novel textured surface for blood-contact," Biomaterials, vol. 20, pp. 955-962, (1999).

Fulton, "Ion-Assisted Filtered Cathodic Arc Deposition (IFCAD) System for Volume Production of Thin-Film Coatings," Society of Vacuum Coaters, 42nd Annual Technical Conference Proceedings, (1999).

Gabel et al., "Solid-State Spray Forming of Aluminum Near-Net Shapes," Journal of Metals, vol. 49, No. 8, pp. 31-33, (1997).

Gabel, "Low Temperature Metal Coating Method," Lawrence Livermore National Laboratory, Apr. 3, 2000.

Gadegaard et al., "Tubes with Controllable Internal Nanotopography," Advanced Materials, vol. 16, No. 20, pp. 1857-1860, Oct. 18, 2004.

Galinski et al., "Ionic liquids as electrolytes," Electrochimica Acta, vol. 51, 5567-5580, (2006).

Gao, "Chemical Vapor Deposition," Handbook of Nanophase and Nanostructured Materials, vol. 1: Synthesis, Chapter 5, (2003).

Geretovszky et al., "Correlation of compositional and structural changes during pulsed laser deposition of tantalum oxide films," Thin Solid Films, vol. 453-454, pp. 245-250, (2004).

Gillanders et al., "A Composite Sol-Gel/Fluoropolymer Matrix for Dissolved Oxygen Optical Sensing," Journal of Photochemistry and Photobiology A: Chemistry, vol. 163, pp. 193-199, (2004).

Glocker et al., "AC Reactive Sputtering with Inverted Cylindrical Magnetrons," Society of Vacuum Coaters, 43rd Annual Technical Conference Proceedings—Denver, pp. 81-85, Apr. 15-20, 2000.

Glocker et al., "Recent developments in inverted cylindrical magnetron sputtering," PowerPoint presentation, (2001).

Glocker et al., "Recent developments in inverted cylindrical magnetron sputtering," Surface and Coatings Technology, vol. 146-147, pp. 457-462, (2001).

Goddard et al., "Polymer surface modification for the attachmend of bioactive compounds," Progress in Polymer Science, vol. 32, pp. 698-725, (2007).

Goh et al., "Nanostructuring Titania by Embossing with Polymer Molds Made from Anodic Alumina Templates," Nano Letters, vol. 5, No. 8, pp. 1545-1559, (2005).

Gollwitzer et al., "Titania Coating as Local "Drug" Delivery System with Antibacterial and Biocompatible Properties," (2003).

Gong et al., "Controlled molecular release using nanopourous alumina capsules," Biomedical Microdevices, vol. 5, No. 1, pp. 75-80, Mar. 2003.

Gong et al., "Titanium oxide nanotube arrays prepared by anodic oxidation," Journal of Material Research, vol. 16, No. 12, pp. 3331-3334, (2001).

Goodison et al., "CD44 cell adhesion molecules," Journal of Clinical Pathology: Molecular Pathology, vol. 52, pp. 189-196, (1999).

Goodman et al., "Three-dimensional extracellular matrix textured biomaterials," Biomaterials, vol. 17, pp. 2087-295, (1996).

Gorb et al., "Biological microtribology: anisotropy in frictional forces of orthopteran attachment pads reflects the unitrastructure of a highly deformable material," Proceeding of the Royal Society, London series B, vol. 267, pp. 1239-1244, (2000).

Gotszalk et al., "Diagnostics of micro- and nanostructure using the scanning probe microscopy," Journal of Telecommunications and Information Technology, pp. 41-46, (2005).

Granqvist et al., "Biodegradable and bioactive hybrid organic-inorganic PEG-siloxane fibers: Preparation and Characterization," Colloid Polymer Science, vol. 282, pp. 495-501, (2004).

Greeley et al., "Electrochemical dissolution of surface alloys in acids: Thermodynamic trends from first-principles calculations," Electrochimica Acta, vol. 52, pp. 5829-5836, (2007).

Green et al., "XPS Characterisation of Surface Modified Ni-Ti Shape Memory Alloy," Materials Science and Engineering, vol. A224, pp. 21-26, (1997).

Gressel-Michel et al., "From a Microwave Flash-Synthesized $TiO_2$ Colloidal Suspension to $TiO_2$ Thin Films," Journal of Colloid and Interface Science, vol. 285, pp. 674-679, (2005).

Groth et al., "Layer-by-Layer Deposition of Polyelectrolytes—A Versatile Tool for the In Vivo Repair of Blood Vessels," Angewandte Chemie, International Edition, vol. 43, pp. 926-928, (2004).

Grubmuller, "What happens if the Room at the Bottom Runs Out? A Close Look at Small Water Pores," PNAS, vol. 100, No. 13, pp. 7421-7422, Jun. 24, 2003.

Gu et al., "Biomimetic titanium dioxide film with structural color and extremely stable hydrophilicity," Applied Physics Letters, vol. 85, No. 21, pp. 5067-5069 (2004).

Guangliang et al., "The effects of current density on the phase composition and microstructure properties of micro-arc oxidation coating," Journal of Alloys and Compounds, vol. 345, pp. 169-200, (2002).

Guo et al., "Formation of oxygen bubbles and its influence on current efficiency in micro-arc oxidation process of AZ91D magnesium alloy," Thin Solid Films, vol. 485, pp. 53-58, (2005).

Guo et al., "Growth of ceramic coatings on AZ91D magnesium alloys by micro-arc oxidation in aluminate-fluoride solutions and evalucation of corrosion resistance," Applied Surface Science, col. 246, pp. 229-238, (2005).

Guo et al., "Investigation of corrosion behaviors of Mg-6Gd-3Y-0.4Zr alloy in NaCl aqueous solutions," Electrochimica Acta, vol. 52, pp. 2570-2579, (2007).

Guo et al., "Sol gel derived photocatalytic porous $TiO_2$ thin films," Surface & Coatings Technology, vol. 198, pp. 24-29, (2005).

GVD Corporation, "Nanocoatings for a New Era," [first downloaded Nov. 12, 2003].

Haag et al., "Polymer Therapeutics: Concepts and Applications," Angewandte Chemie, vol. 45, pp. 1198-1215, (2006).

Haberland et al., "Filling of micron-sized contact holes with copper by energetic cluster impact," Journal of Vacuum Science Technology A, vol. 12, No. 5, pp. 2925-2930, Sep./Oct. 1994.

Haery et al., "Drug-eluting stents: The beginning of the end of restenosis?," Cleveland Clinic Journal of Medicine, vol. 71, No. 10, pp. 815-824, (2004).

Hahn et al., "A novel approach for the formation of Mg(OH)2/MgO nanowhiskers on magnesium: Rapid anodization in chloride containing solutions", Electrochemistry Communications, vol. 10, pp. 288-292, (2008).

Halme et al., "Spray Deposition and Compression of $TiO_2$ Nanoparticle Films for Dye-Sensitized Solar Cells on Plastic Substrates," Solar Energy Materials & Solar Cells, vol. 90, pp. 887-899, (2006).

Hamley et al., "Nanostructure fabrication using block copolymers," Nanotechnology, vol. 14, pp. R39-R54, (2003).

Han et al., "Electron injection enhancement by diamond-like carbon film in organic electroluminescence devices," Thin Solid Films, vol. 420-421, pp. 190-194, (2002).

Han et al., "Pourous nanocrystalline titania films by plasma electrolytic oxidation," Surface and Coatings Technology, vol. 154, pp. 314-318, (2002).

Han et al., "Structure and in vitro bioactivity of titania-based films by micro-arc oxidation," Surface and Coatings Technology, vol. 168, pp. 249-258, (2003).

Han et al., "Synthesis of nanocrystalline titaniaa films by micro-arc oxidation," Materials Letters, vol. 56, pp. 744-747, (2002).

Hanley et al., "The growth and modification of materials via ion-surface processing," Surface Science, vol. 500, pp. 500-522, (2002).

Harris et al., "Fabrication of Perforated Thin Films with Helical and Chevron Pore Shapes," Electrochemical and Solid-State Letters, vol. 4, pp. C39-C42, (2004).

Harvard Nanopore, "Ion Beam Sculpting: Material Science—Fabricating Nanopores and Other Nanoscale Feature," [first downloaded Jul. 2, 2003], (http://www.mcb.harvard.edu.branton/projects-IonBeam/htm).

Hattori et al., "Photoreactivity of Sol-Gel $TiO_2$ Films Formed on Soda-Lime Glass Substrates: Effect of $SiO_2$ Underlayer Containing Flurine," Langmuir, vol. 15, pp. 5422-5425, (1999).

Hau et al., "Surface-chemistry technology for microfluidics," Journal of Micromechanics and Microengineering, vol. 13, pp. 272-278, (2003).

Hausleiter et al., "Prvention of restenosis by a novel drug-eluting stent system with a dose-adjustable, polymer-free, on-site stent coating," European Heart Journal, vol. 26, pp. 1475-1481, (2005).

He et al., "Electrochemical Fabrication of Metal Nanowires," Encyclopedia of Nanoscience and Nanotechnology, vol. X, pp. 1-18, (2003).

He et al., "Optical properties of diamond-like carbon synthesized by plasma immersion ion processing," Journal of Vacuum Science Technology, vol. B17, No. 2, pp. 822-827, Mar./Apr. 1999.

Heidenau et al., "Structured Porous Titania as a Coating for Implant Materials," Key Eng Mater. vol. 192-195, pp. 87-90, (2001).

Heinig et al., "Modeling and Simulation of Ion Beam Systhesis of Nanoclusters," 6 pages, [first downloaded Jan. 3, 2000], (http://www.fz-rossendorf.de/pls/rois/Cms?pOId=10960&pFunc=Print&pLang=de).

Helmersson et al., "Ionized physical vapor deposition (IPVDd): A review of technology and applications," Thin Solid Films, vol. 513, pp. 1-24, (2006).

Helmus et al. "Surface Analysis of a Series of Copolymers of $_L$-Glutamic Acid and $_L$-Leucine," Journal of Colloid and Interface Science, vol. 89, No. 2, pp. 567-570, (1982).

Helmus et al., "Plasma Interaction on Block Copolymers as Determined by Platelet Adhesion," Biomaterials: Interfacial Phenomena and Applications: Chapter 7, pp. 80-93, (1981).

Helmus et al., "The Effect of Surface Charge on Arterial Thrombosis," Journal of Biomedical Materials Research, vol. 18, pp. 165-183, (1984).

Hentze et al., "Porous polymers and resins for biotechnological and biomedical applications," Reviews in Molecular Biology, vol. 90, pp. 27-53, (2002).

Hoa et al., "Preparation of porous meterials with ordered hole structure," Advances in Colloid and Interface Science, vol. 121, pp. 9-23, (2006).

Hoffman, "Non-Fouling Surface Technologies," Journal of Biomaterials Science, Polymer Edition, vol. 10, No. 10, pp. 1011-1014, (1999).

Hoglund, "Controllable Degradation Product Migration From Biomedical Polyester-ethers," KTH Chemical Science and Engineering, Stockholm, May 24, 2007.

Holland et al., "Synthesis of Macroporous Minerals with Highly Ordered Three-Dimensional Arrays of Spheroidal Voids," Science, vol. 281, pp. 538-540, Jul. 24, 1998.

Hong et al., "The super-hydrophilicities of Bi-TiO2, V-TiO2, and Bi-V-TiO2 nano-sized particles and their benzene photodecompositions with H2O addition," Materials Letters, vol. 60, pp. 1296-1305, (2006).

Hopp et al., "Absorbing film assisted laser induced forward transfer of fungi (*Trichoderma conidia*)," Journal of Applied Physics, vol. 96, No. 6, pp. 3478-3481, Sep. 15, 2004.

Houbertz, "Laser interaction in sol-gel based materials—3-D lithography for photonic applications," Applied Surface Science, vol. 247, pp. 504-512, (2005).
Houdayer et al., "Preparation of new antimony(0)/polyaniline nanocomposites by a one-pot solution phase method," Materials Letter, vol. 61, pp. 171-176, (2007).
Hrudey et al., "Organic Alq$_3$ Nanostructures Fabricated with Glancing Angle Depostion," Vacuum Technology & Coating, May 2006.
Hsiao et al., "Soluble aromatic polyamides bearing asymmetrical diaryl ether groups," Polymer, vol. 45, pp. 7877-7885, (2004).
Hu et al., "Cyclic voltammetric deposition of hydrous ruthenium oxide for electrochemical capacitors: effects of codeposting iridium oxide," Electrochimica Acta, vol. 45, pp. 2684-2696, (2000).
Hu et al., "Voltammetric investigation of platinum oxides II. Efect of hydration on the reduction behavior," Electrochimica Acta, vol. 45, pp. 3063-3068, (2000).
Hiippauff et al., "Valency and Structure of Iridium in Anodic Iridium Oxide Films," Journal of Electrochemical Society, vol. 140, No. 3, pp. 598-602, Mar. 1993.
Hurley et al., "Nanopatterning of Alkynes on Hydrogen-Terminated Silicon Surfaces by Scanning Probe-Induced Cathodic Eletrografting," Journal of American Chemistry Society, vol. 125, pp. 11334-11339, (2003).
Hussain et al., "Atomic force microscope study of three-dimensional nanostructure sidewalls," Nanotechnology, vol. 18, pp. 1-8, (2007).
Ichinose et al., "A surface sol-gel process of $TiO_2$ and other metal oxide films with molecular precision," Chem. Mater. vol. 9, pp. 1296-1298, (1997).
Ichinose et al., "Ultrathin composite films: An indispensable resource for nanotechnolo ," Riken Review, No. 37, pp. 34-37, Jul. 2001.
Ignatova et al., "Combination of Electrografting and Aton-Transfer Radical Polymerization for Making the Stainless Steel Surface Antibacterial and Protein Antiadhesive," Langmuir, vol. 22, pp. 255-262, (2006).
Imai et al., "Preparation of Porous Anatase Coatings from Sol-Gel-Derived Titanium Dioxide and Titanium Dioxide-Silica by Water-Vapor Exposure," Journal of American Ceramics Society, vol. 82, No. 9, pp. 2301-2304, (1999).
Inflow Dynamics starts "LUSTY" Study, Company Press Release: First clinical trial with Niobium stents, (www.tctmd.com/industry-news/one.html?news_id=3364), Jun. 25, 2002.
Inoue et al., "Corrosion rate of magnesium and its alloys in buffered chloride solutions," Corrosion Science, vol. 44, pp. 603-610, (2002).
Inovati, "Award Winning—Environmentally-Safe, High-Quality, Metal Spray Process," Press Release, (2002), (http://www.inovati.com/papers/KM-PressRelease.doc).
Inovati, "Inovati to Develop Green Metal Coating Technology" Press Release, [first downloaded Sep. 1, 2005], (http://www.inovati.com/papers/bmdopr.html).
Inovati, "Low temperature, high-speed sprays make novel coatings," [first downloaded on Mar. 18, 2003], (http://www.inovati.com/papers/ampmar01.html).
Introduction to the Metal Printing Process: Future manufacturing equipment of advanced materials and complex geometrical shapes, (www.mpp.no/introfintro.htm), downloaded Mar. 18, 2002.
Irhayem et al., "Glucose Detection Based on Electrochemically Formed Ir Oxide Films," Journal of Electroanalytical Chemisty, vol. 538-539, pp. 153-164, (2002).
Irvine et al., Nanoscale clustering of RGD peptides at surfaces using Comb polymers. 1. Synthesis and characterization of Comb thin films, Biomacromolecules, vol. 2, No. 1, pp. 85-94, Spring 2001.
Irvine et al., "Nanoscale clustering of RGD peptides at surfaces using comb polymers. 2. Surface segregation of comb polymers in polylactide," Biomacromolecules, vol. 2, No. 2, pp. 545-556, Summer 2001.
Ishizawa et al., "Characterization of thin hydroxyapatite layers formed on anodic titanium oxide films containing Ca and P By hydrothermal treatment," Journal of Biomedical Materials Research, vol. 29, pp. 1071-1079, (1995).
Ishizawa et al., "Histomorphometric evaluation of the thin hydroxyapatite layer formed through anodization followed by hydrothermal treatment," Journal of Biomedical Materials Research, vol. 35, pp. 199-206, (1997).

Isoflux Inc., "Isoflux specializes in vacuum coating equipment and coating process," http://www.isofluxinc.com/about.shtml, Jul. 2009.
Iurhayem et al. "Glucose detection based on electrochemically formed Ir oxide films," Journal of Electroanalytical Chemistry, vol. 539-539, pp. 153-164, (2002).
Jensen et al., "Low-temperature preparation of nanocrystalline anatase films through a sol-gel rout," Journal of Sol-Gel Science and Technology, vol. 39, pp. 229-233, (2006).
Jewell et al., "Multilayered polyelectolyte films promote the direct and localized delivery of DNA to cells," Journal of Controlled Release, vol. 106, pp. 214-223, (2005).
JMAR LLC, "Collimated Plasma Lithography (CPL)," [first downloaded Jul. 2, 2003], (http://www.jmar.com/co451.html).
Johnson, "What's an Ionic Liquid?," The Electrochemical Society: Interface, pp. 38-41, Spring 2007.
Juodkazis et al., "Alternative view of anodic surface oxidation of nobel metals," Electrochimica Acta, vol. 51, pp. 6159-6164, (2006).
Kamei et al., "Hydrophobic drawings on hydrophilic surfaces of single crystalline titanium dioxide: surface wettability control by mechanochemical treatment," Surface Science Letters, vol. 463 pp. L609-L612, (2000).
Kanda et al., "Characterization of Hard Diamond-Like Carbon Films Formed by Ar Gas Cluster Ion Beam-Assisted Fullerene Deposition," Japanese Journal of Applied Physics, vol. 41, Part 1, No. 6B, pp. 4295-4298, Jun. 2002.
Kang et al., "Controlled drug release using nanoporous anodic aluminum oxide on stent," Thin Solid Films, vol. 515, pp. 5184-5187, (2007).
Kaplan, "Cold Gas Plasma and Silanes," Presented at the 4th International Symposium on Silanes and Other Coupling Agents, Jul. 11-13, 2003.
Karuppuchamy et al., "Cathodic Electrodeposition of Oxide Semiconductor Thin Films and their Application to Dye-Sensitized Solar Cells," Solid State Ionics, vol. 151, pp. 19-27, (2002).
Karuppuchamy et al., "Photoinduced Hydrophilicity of Titanium Dioxide Thin Films Prepared by Cathodic Electrode position," Vacuum, vol. 80, pp. 494-498, (2006).
Karuppuchamy et al., "Super-hydrophilic amorphous titanium dioxide thin film deposited by cathodic electrodeposition," Materials Chemisty and Physics, vol. 93, pp. 251-254, (2005).
Karuri et al., "Biological length scale topography enhances cell-substratum adhesion of human corneal epithelial cells," Journal of Cell Science, vol. 117, No. 15, pp. 3153-3164, (2004).
Kasemo et al., "Implant surfaces and interface processes," Adv. Dent. Res. vol. 13, pp. 8-20 Jun. 1999.
Kasemo, "Biological surface science," Surface Science, vol. 500, pp. 656-677, (2002).
Kato et al., "N-succinyl-chitosan as a drug carrier: water-insoluble and water-soluble conjugates," Biomaterials, vol. 25, pp. 907-915, (2004).
Katsumata et at., "Effect of Microstructure on Photoinduced Hydrophilicity of Transparent Anatase Thin Films," Surface Science, vol. 579, pp. 123-130, (2005).
Katz, "Developments in Medical Polymers for Biomaterials Applications," Medical Device Link, Jan. 2001, (http://www.devicelink.com/mddi/archive/01/01/003.html).
Kean et al. "The Analysis of Coatings Produced by Accelerated Nanoparticles," Mantis Deposition Ltd., Presentaction at NSTI Nano Tech 2006, Boston, May 7-11, 2006.
Kesapragada et al., "Two-component nanopillar arrays grown by Glancing Angle Deposition," Thin Solid Films, vol. 494, pp. 234-239, (2006).
Kesler et al., "Enhanced Strength of Endothelial Attachment on Polyester Elastomer and Polytetrafluoroethylene graft Surfaces with Fibronectin Substrate," Journal of Vascular Surgery, vol. 3, No. 1, pp. 58-64, (1986).
Kesting, "Synthetic Polymeric Membranes—A Structural Perspective", Chapters 6-7, pp. 225-286, Oct. 1985.
Kickelbick, "Concepts for the incorporation of inorganic building blocks into organic polymers on a nanoscale," Progress in Polymer Science, vol. 28, pp. 81-114, (2003).

Kidambi et al., "Selective Depositions on Polyelectrolyte Multilayers: Self-Assembled Monolayers on m-dPEG Acid as Molecular Template," Journal of the American Chemistry Society, vol. 82, No. 9, pp. 4697-4703, (2004).

Kilian et al., "Plasma transglutaminase factor XIII induces microvessel ingrowth into biodegradable hydroxyapatite implants in rats," Biomaterials, vol. 26, pp. 1819-1827, (2005).

Kim et al. "Porous ZrO2 bone scaffold coated with hydroxyapatite with fluorapatite intermediate layer," Biomaterials, vol. 24, pp. 3277-3284, (2003).

Kim et al., "Adhesion of RF bias-sputtered Cr thin films onto photosensitivepolyimide substrates," IEEE, International Symposium on Eelectrical Materials and Pakaging, pp. 202-207, (2001).

Kim et al., "Fabrication of WC-Co coatings by cold spray deposition," Surface & Coatings Technology, vol. 191, pp. 335-340, (2005).

Kim et al., "Hollow Silica Spheres of Controlled Size and Porosity by Sol-Gel Processing," Journal of Americal Ceramic Society, vol. 74, Nol. 8, pp. 1987-1992, (1991).

Kim et al., "Proton conducting polydimethylsiloxane/metal oxide hybrid membranes added with phosphotungstic acid(II)," Electrochimica Acta, vol. 49, pp. 3429-3433, (2004).

Kim et al., "Fabrication and Characterization of $TiO_2$ Thin Film Prepared by a Layer-By-Layer Self-Assembly Method," Thin Solid Films, vol. 499, pp. 83-89, (2006).

Kitagawa et al., "Near-Edge X-Ray Absorption Fine Structure Study for Optimization of Hard Diamond-Like Carbon Film Formation with Ar Cluster Ion Beam," Japanese Journal of Applied Physics, vol. 42, pp. 3971-3975, (2003).

Kitagawa et al., Optimum Incident Angle of Ar Cluster Ion Beam for Superhard Carbon Film Deposition, Japanese Journal of Applied Physics, vol. 43, No. 6B, pp. 3955-3958, (2004).

Kittaka et al., "The Structure of Water Monolayers on a Hydroxylated Chromium Oxide Surface," Adsorption, vol. 11, pp. 103-107, (2005).

Kleinertz et al., "Lusty Studie: Lunar STF Study," PowerPoint presentation on Sep. 4, 2004.

Kleisner et al., "A system based on metal alkyl species that forms chemically bound organic overlays on hydroxylated planar surfaces," Thin Solid Films, vol. 381, pp. 10-14, (2001).

Kogure et al., "Microstructure of nemalite, fibrous iron-bearing brucite", Mineralogical Journal, vol. 20, No. 3, pp. 127-133, Jul. 1998.

Kohli et al., "Arrays of lipid bilayers and liposomes on patterned polyelectrolyte templates," Journal of Colloid and Interface Science, vol. 301, pp. 461-469, (2006).

Kokubo et al., "Novel bioactive materials with different mechanical properties," Biomaterials, vol. 24, pp. 2161-2175, (2003).

Kommireddy et al., "Layer-by-Layer Assembly of $TiO_2$ Nanoparticles for Stable Hydrophilic Biocompatible Coatings" Journal of Nanoscience and Nanotechnology, vol. 5, pp. 1081-1087, (2005).

Kondyurin et al., "Plasma Immersion ion implantation of polyethylene," Vacuum, vol. 64, pp. 105-111, (2002).

Kong et al., "Polyelectrolyte-functionalized multiwalled carbon nanotubes: preparation, characterization and layer-by-layer self-assembly," Polymer, vol. 46, pp. 2472-2485, (2005).

Konig et al., "Nanoprocessing with nanojoule near-infrared femtosecond laser pulses," Medical Laser Application, vol. 20, pp. 169-184, (2005).

Konishi et al., "Morphology Control of Dy-Ni Alloy Films by Electrochemical Displantation," Electrochemical and Solid-State Letters, vol. 5, No. 12, pp. B37-B39, (2002).

Koo et al., "Co-regulation of cell adhesion by nanoscale RGD organization and mechanical stimulus," Journal of Cellular Science, vol. 115, Part 7, pp. 1423-1433, Apr. 1, 2002.

Kopanski et al., "Scanning Kelvin Force Microscopy For Characterizing Nanostructures in Atmosphere," Characterization and Metrology for Nanoelectronics: 2007 International Conference on Frontiers of Characterization and Metrology. American Institute of Physics Conference Proceedings, vol. 931, pp. 530-534, Sep. 26, 2007.

Kostov et al., "Two Dimensional Computer Simulation of Plasma Immersion Ion Implantation," Brazilian Journal of Physics, vol. 34, No. 4B, pp. 1689-1695, Dec. 2004.

Kotz et al., "XPS Studies of Oxygen Evolution on Ru and $RuO_2$ Anodes," Journal of Electrochemical Society: Electrochemical Science and Technology, pp. 825-829, Apr. 1983.

Kowalski et al., "Corrosion protection of steel by bi-layered polypyrrole doped with molybdophosphate and naphthalenedisulfonate anions," Corrosion Science, Vo. 49, pp. 1635-1644, ( 2007).

Kraft et al., "Thin films from fast clusters: golden TiN layers on a room temperature substrate" Surface and Coatings Technology 158-159, pp. 131-135, (2002).

Krumeich et al., "HyFraSurf-Advanced Surface Technology for Superior Electrode Performance," European Cells and Materials, vol. 1, Suppl. 1, p. 43, (2001).

Kumar et al., "Influence of electric field type on the assembly of single walled carbon nanotubes," Chemical Physics Letters, vol. 383, pp. 235-239, (2004).

Kumar et al., "Polyanhydrides: an overview," Advanced Drug Delivery Reviews, vol. 54, pp. 889-910, (2002).

Kunitake et al., "Molecular imprinting in ultrathin titania gel films via surface sol-gel process," Analytica Chimica Acta, vol. 504, pp. 1-6, (2004).

Kurth et al., "Multilayers on Solid Planar Substrates: From Structure to Function," Multilayer Thin Films: Sequential Assembly of Nanocomposite Materials, Chapter 14, pp. 393-426, Mar. 7, 2003.

Kutsenko et al., "Structural changes in Mg alloy induced by plasma immersion ion implantation of Ag," Acta Materialia, vol. 52, pp. 4329-4335, (2004).

Kutz, "Biomaterials to Promote Tissue Regeneration," in Standard Handbook of Biomedical Engineering and Design, ISBN 0-07-135637-1, pp. 16.13-16.29, (2003).

Kvastek et al., "Electochemical properties of hydrous rithenium oxide films formed and measured at different potentials," Journal of Electroanalytical Chemistry, vol. 511, pp. 65-78, (2001).

Lakard et al., "Adhesion and proliferation of cells on new polymers modified biomaterials," Bioelectrochemistry, vol. 62, pp. 19-27, (2004).

Lakatos-Varsanyi et al., "Cyclic voltammetry measurements of different single-, bi- and multilayer TiN and single layer CrN coatings on low-carbon-steel substrates," Corrosion Science, vol. 41, pp. 1585-1598, (1999).

Lamaka et al., "$TiO_x$ self-assembled networks prepared by templating approach as nanostructured reservoirs for self-healing anticorrosion pre-treatments," Electrochemistry Comunications, vol. 8, pp. 421-428, (2006).

Lamer et al., "The Challenge of Plasma Processing—Its Diversity," Presented at the ASM Materials and Processes for Medical Devices Conference, Aug. 25-27, 2004.

Laser-Induced Forward Transfer (LIFT): Paul Scherrer Institut, (http://materials.web.psi.ch/Research/Thin_Films/Methods/LIFT.htm), downloaded Dec. 7, 2006.

Lau et al., "Hot-wire chemical vapor deposition (HWCVD) of fluorocarbon and organosilicon thin films," Thin Solid Films, vol. 395, pp. 288-291, (2001).

LaVan et al., Small-scale systems for in vivo drug delivery, Nature Biotechnology, vol. 21, No. 10, pp. 1184-1191, Oct. 2003.

Leary-Swan et al., "Fabrication and evaluation of nanoporous alumina membranes for osteoblast culture," Journal of Biomedical Materials Research: Part A, vol. 72A, pp. 288-295, (2005).

Lee et al., "A Template-Based Electrochemical Method for the Synthesis of Multisegmented Metallic Nanotubes," Angewandte Chemie, vol. 44, pp. 6050-6054, (2005).

Lee et al., "Biocompatibility and Charge Injection Property of Iridium Film Formed by Ion Beam Assisted Deposition," Biomaterials, vol. 24, pp. 2225-2231, (2003).

Lee et al., "Structural characterization of porous low-k thin films prepared by different techniques using x-ray porosimetry," Journal of Applied Physics, vol. 95, No. 5, Mar. 1, 2004.

Lee et al., "A study on electrophoretic deposition of Ni nanoparticles on pitted Ni alloy 600 with surface fractality", Journal of Colloid and Interface Science, vol. 308, pp. 413-420, (2007).

Lefaux et al., "Polyelectrolyte Spin Assembly: Influence of Ionic Strenght on the Growth of Multilayered Thin Films," Journal of Polymer Science Part B: Polymer Physics, vol. 42, pp. 3654-3666, (2004).

Lei et al., "Fabrication of Highly Ordered Nanoparticle Arrays Using Thin Porous Alumina Masks," Advanced Materials for Micro- and Nano-Systems (AMMNS), Jan. 2001.

Leng et al., "Mechanical properties and platelet adhesion behavior of diamond-like carbon films synthesized by pulsed vacuum arc plasma deposition," Surface Science, vol. 531, pp. 177-184, (2003).

Lenza et al., "In vitro release kinetics of proteins from bioactive foams," Journal of Biomedical Materials Research: A, vol. 67, No. 1, pp. 121-129, Oct. 2003.

Leoni et al., "Characterization of Nanoporous Membranes for immunoisolation: Diffusion Properties and Tissue Effects," Biomedical Microdevices, vol. 4, No. 2, pp. 131-139, (2002).

Leoni et al., "Nanoporous Platforms for Cellular Sensing and Delivery," Sensors, 51(2), pp. 111-120, (2002).

Leung et al., "Fabrication of photonic band gap crystal using microtransfer molded templates," Journal of Applied Physics, vol. 93, No. 10, pp. 5866-5870, May 15, 2003.

Lewis et al., "Silicon nonopillars formed with gold colloidal partical masking," Journal of Vacuum Science Technology B, vol. 16, No. 6, pp. 2938-2941, Nov./Dec. 1998.

Li et al., "A simple approach to fabricate amorphous silicon pattern on single crystal silicon," Tribology International, vol. 40, pp. 360-364, (2007).

Li et al., "Bioactive Hydroxyapatite Composite Coating Prepared by SOL-Gel Process," Journal of Sol-Gel Science and Technology, vol. 7, pp. 27-34, (1996).

Li et al., "Fabrication and Microstructuring of Hexagonally Ordered Two-Dimensional Nanopore Arrays in Anodic Alumina," Advanced Materials, vol. 11, pp. 483-487, (1999).

Li et al., "Hexagonal pore arrays with a 50-420 nm interpore distance formed by self-organization in anodic alumina," Journal of Applied Physics, vol. 84, No. 11, pp. 6023-6026, Dec. 1, 1998.

Li et al., "Improved biological performance of Ti implants due to surface modification by micro-arc oxidation," Biomaterials, vol. 25, pp. 2867-2875, (2004).

Li et al., "On the growth of highly ordered pores in anodized aluminum oxide," Chem. Mater., vol. 10, pp. 2470-2480, (1999).

Li et al., "pH-compensation effect of bioactive inorganic fillers on the degradation of PLGA," Composites Science and Technology, vol. 65, pp. 2226-2232, (2005).

Li et al., "Polycrystalline nanopore arrays with haxagonal ordering on aluminum," Journal of Vacuum Science Technology: A, vol. 17, pp. 1428-1431, (1999).

Li et al., "A novel method for preparing surface-modified Mg(Oh)2 nanocrystallines," Materials Science and Engineering A, 452-453, pp. 302-305, (2007).

Li, "Poly(L-glutamic acid)-anticancer drug conjugates," Advanced Drug Delivery Reviews, vol. 54, pp. 695-713, (2002).

Liaw et al., "Process Monitoring of Plasma Electrolytic Oxidation," presented at the 16th World Conference on Nondestructive Testing, Montreal, Canada, Aug. 30-Sep. 3, 2004.

Liebling et al., "Optical Properties of Fibrous Brucite from Asbestos, Quebec", American Mineralogist, vol. 57, pp. 857-864, (1972).

Lim et al., "Systematic variation in osteoblast adheasion and phenotype with substratum surface characteristics," Journal of Biomedical Materials and Research, vol. 68A, No. 3, pp. 504-511, (2004).

Lim et al., "UV-Driven Reversible Switching of a Roselike Vanadium Oxide Film between Superhydrophobicity and Superhydrophilicity," Journal of American Chemical Society, vol. 129, pp. 4126-4129, Mar. 15, 2007.

Lin et al., "PWA-doped PEG/SiO$_2$ proton-conducting hybrid membranes for fuel cell applications," Journal of Membrane Science, vol. 254, pp. 197-205, (2005).

Lindstrom et al., "A New Method for Manufacturing Nanostructured Electrodes on Glass Substrates," Solar Energy Materials & Solar Cells, vol. 73, pp. 91-101 (2002).

Lippert et al., "Chemical and Spectroscopic Aspects of Polymer Ablation: Special Features and Novel Directions," Chemical Reviews, vol. 103, pp. 453-485, (2003).

Liu et al., "A metal plasma source ion implantation and deposition system," American Institute of Physics, Review of Scientific Instruments, vol. 70, No. 3, pp. 1816-1820, Mar. 1999.

Liu et al., "Electrodeposition of Polypyrrole Films on Aluminum from Tartrate Aqueous Solution," Journal of Brazilian Chemical Society, vol. 18, No. 1, pp. 143-152, (2007).

Liu et al., "Surface modification of titanium, titanium alloys, and related materials for biomedical applications," Materials Science and Engineering R, vol. 47, pp. 49-121, (2004).

Lu et al., "Fabricating Conducting Polymer Electrochromic Devices Using Ionic Liquids," Journal of The Electrochemical Society, vol. 151, No. 2, pp. H33-H39, (2004).

Lu et al., "Micro and nano-fabrication of biodegradable polymers for drug delivery," Advanced Drug Delivery Reviews, vol. 56, pp. 1621-1633, (2004).

Lv et al., "Controlled growth of three morphological structures of magnesium hydroxide nanoparticles by wet precipitation method," Journal of Crystal Growth, vol. 267, pp. 676-684, (2004).

Lv et al., "Controlled synthesis of magnesium hydroxide nanoparticles with different morphological structures and related properties in flame retardant ethyolene-vinyl acetate blends", Nanotechnology, vol. 15, pp. 1576-1581, (2004).

Lv et al., "In situ synthesis of nanolamellas of hydrophobic magnesium hydroxide", Colloids and Surfaces A: Physicochemical and Engineering Aspects, vol. 296, pp. 97-103, (2007).

Maeda et al., "Effect of Silica Addition on Crystallinity and Photo-Induced Hydrophilicity of Titania-Silica Mixed Films Prepared by Sol-Gel Process," Thin Solid Films, vol. 483, pp. 102-106, (2005).

Maehara et al., "Buildup of Multilayer Structures of Organic-Inorganic Hybrid Ultra Thin Films by Wet Process," Thin Solid Films, vol. 438-439, pp. 65-69, (2003).

Maheshwari et al., "Cell adhesion and motility depend on nanoscale RGD clustering," Journal of Cell Science, vol. 113, Part 10, pp. 1677-1686, May 2000.

Maitz et al., "Blood Compatibility of Titanium Oxides with Various Crystal Structure and Element Doping," Journal of Biomaterials Applications, vol. 17, pp. 303-319, Apr. 2003.

Manna et al., "Microstructural Evalution of Laser Surface Alloying of Titanium with Iridium," Scripta Materialia, vol. 37, No. 5, pp. 561-568, (1997).

Manoharan et al., "Ordered macroporous rutile titanium dioxide by emulsion templating," Proceedings of SPIE, vol. 3937, pp. 44-50, (2000).

Mantis Deposition Ltd., "Nanocluster Deposition," Thame, Oxforshire, United Kingdom, [downloaded on Feb. 2, 2007], (http://www.mantisdeposition.com/nanocluster.html).

Martin et al., "Microfabricated Drug Delivery Systems: Concepts to Improve Clinical Benefit," Biomedical Microdevices, vol. 3, No. 2, pp. 97-107, Jun. 2001.

Martin, "Pulsed Laser Deposition and Plasma Plume Investigations," Andor Technology, Ltd. (2003).

Masuda et al., "Highly ordered nanochannel-array architecture in anodic alumina," Applied Physics Letters, vol. 71, pp. 2770-2772, (1997).

Matijević, "Colloid Chemical Aspects of Corrosion of Metals", Pure & Applied Chemisty, vol. 52, pp. 1179-1193, (1980).

Mattox, "Introduction: Physical Vapor Deposition (PVD) Processes," Vacuum Technology & Coating, pp. 60-63, Jul. 2002.

Mattox, "The History of Vacuum Coating Technology: Part V," Vacuum Technology & Coating, pp. 32-37, Oct. 2002.

Mattox, "The History of Vacuum Coating Technology: Part VI," Vacuum Technology & Coating, pp. 52-59, Oct. 2002.

Mauritz Group Homepage, "Sol-Gel Chemistry and Technology," (htty://www.psrc.usin.edu/mauritz/solgel.html) (downloaded [2006]).

McGuigan et al., "The influence of biomaterials on endothelial cell thrombogenicity," Biomaterials, vol. 28, pp. 2547-2571, (2007).

McNally et at., "Cathodic Electrodeposition of Cobalt Oxide Films Using Polyelectrolytes," Materials Chemistry and Physics, vol. 91, pp. 391-398, (2005).

Meijer et al., "Laser Machining by short and ultrashort pulses, state of the art and new opportunities in the age of the photons," Annals of CIRP 2002: Manufacturing Technology, vol. 51, No. 2, pp. 531-550, (2002).

Meletis et al., "Electrolytic plasma processing for cleaning and metal-coating of steel surfaces," Surface and Coatings Technology, vol. 150, pp. 246-256, (2002).

Merriam-Webster's Dictionary Website: For definition of Strut, [first cited Jul. 21, 2010], (http://www.merriam-webster.com/dictionary/strut).

MicroFab Technologies Inc. "MicroFab: Biomedical Applications—Stents," [first downloaded Mar. 23, 2007], (http://www.microfab.com/technology/biomedical/Stents.html).

Mikhaylova et al., "Nanowire formation by electrodeposition in modified nanoporous polycrystalline anodic alumina templates," Mat. Res. Soc. Symp. Proc., vol. 704, pp. w6.34.1-W6.34.6, (2002).

Miller et al., "Endothelial and vascular smooth muscle cell function on poly(lactic-co-glycolic acid) with nano-structured surface features," Biomaterials, vol. 25, No. 1, pp. 53-61, (2004).

Miller et al., "Mechanism(s) of increased vascular cell adhesion on nanostructured poly(lactic-coglycolic acid) films," Journal of Biomedical Materials Research A, vol. 73, No. 4, pp. 476-484, (2005).

MIV Therapeutics, "Hydroxyapatite Coating," [first downloaded Jun. 25, 2003], (http://www.mivtherapeutics.com/technology/hap/).

Mobedi et al., "Studying the Degradation of Poly(L-lactide) in Presence of Magnesium Hydroxide", Iranian Polymer Journal, vol. 15, No. 1, pp. 31-39, (2006).

Mu et al., "A novel controlled release formulation for the anticancer drug paclitaxel (Taxol): PLGA nanoparticles containing vitamin E TPGS," Journal of Controlled Release, vol. 86, pp. 33-48, (2003).

Mu et al., "Vitamin E TPGS used as emulsifier in the solvent evaporation/extraction technique for fabrication of polymeric nanospheres O for controlled release of paclitaxel (Taxol)", Journal of Controlled Release, vol. 80, pp. 129-144, (2002).

Muller et al., "Solid lipid nanoparticles (SLN) for controlled drug delivery: a review of the state of the art," European Journal of Pharmaceutics and Biopharmaceutics, vol. 50, pp. 161-177, (2000).

Munchow et al., "Poly[(oligoethylene glycol) Dihydroxytitanate] as Organic-Inorganic Polymer-Electrolytes," Electrochimica Acta, vol. 45, pp. 1211-1221, (2000).

Murray et al., "Electrosynthesis of novel photochemically active inherently conducting polymers using an ionic liquid electrolyte," Electrochimica Acta, vol. 51, pp. 2471-2476, (2006).

Naganuma et al., "Preparation of Sol-Gel Derived Titanium Oxide Thin Films Using Vacuum Ultraviolet irradiation with a Xenon Excimer Lamp," Japanese Journal of Applied Physics, vol. 43, No. 9A, pp. 6315-6318, (2004).

Nair et al., "Biodegradable polymers as biomaterials", Progress in Polymer Science, vol. 32, pp. 732-798, (2007).

Nakajima et al., "Effect of Vacuum Ultraviolet Light Illumination on the Crystallization of Sol-Gel-Derived Titanium Dioxide Precursor Films," Surface & Coatings Technology, vol. 192, pp. 112-116, (2005).

Nakayama et al., "Fabrication of drug-eluting covered stents with micropores and differential coating of heparin and FK506," Cardiovascular Radiation Medicine, vol. 4, pp. 77-82, (2003).

NanoBiotech News, vol. 2, No. 26, Jun. 30, 2004.

Nanoparticle coatings: Application note, "Antimicrobial Coatings," MANTIS Deposition Ltd, (2006).

Nanu, "Nanostructured TiO2-CuInS2 based solar cells," Symposium D, Thin Film and Nano-Structured Materials for Photovoltaics, E-MRS Spring Meeting 2003, Jun. 10-13, 2003.

NASA Glenn Research Center, "Fast Three-Dimensional Method of Modeling Atomic Oxygen Undercutting of Protected Polymers," [first downloaded on Jul. 3, 2003], (http://www.grc.nasa.gov/WWW/epbranch/suurtxt/surfaceabs.htm).

Neves et al., "The morphology, mechanical properties and ageing behavior of porous injection molded starch-based blends for tissue engineering scafolding," Materials Science and Engineering, vol. C25, pp. 195-200, (2005).

Newman et al., "Alloy Corrosion," MRS Bulletin, pp. 24-28, Jul. 1999.

Ngaruiya et al., "Structure formation upon reactive direct current magnetron sputtering of transition metal oxide films," Applied Physics Letters, vol. 85, No. 5, pp. 748-750, Aug. 2, 2004.

Ngaruiya et al., "The reactive DC-Magnetron Sputtering Process," (circa 2004).

Nicoll et al., "In vitro release kinetics of biologically active transforming growth factor-beta 1 from a novel porous glass carrier," Biomaterials, vol. 18, Issue 12, pp. 853-859, (1997).

Nicoll et al., "Nanotechnology and Biomaterials—Drugs, Drug Delivery Systems, Quantum Dots and Disease Treatment," Azom. com, [first downloaded Mar. 22, 2004], (http://www.azom.com/details.asp?ArticleID=1853).

Nie et al., "Deposition of layered bioceramic hydroxyapatite/$TiO_2$ coatings on titanium alloys using a hybrid technique of micro-arc oxidation and electrophoresis," Surface Coatings Technology, vol. 125, pp. 407-414, (2000).

Nishio et al., "Preparation and properties of electrochromic iridium oxide thin film by sol-gel process," Thin Solid Films, vol. 350, pp. 96-100, (1999).

Noguera et al., "3D fine scale ceramic components formed by ink-jet prototyping process," Journal of the European Ceramic Society, vol. 25, pp. 2055-2059, (2005).

O'Brien et al., "Passivation of Nitinol Wire for Vascular Implants-A Demonstration of the Benefits," Biomaterials, vol. 23, pp. 1739-1748, (2002).

Oh et al., "Microstructural characterization of biomedical titanium oxide film fabricated by electrochemical method," Surface & Coatings Technology, vol. 198, pp. 247-252, (2005).

Orloff et al., "Biodegradable implant strategies for inhibition of restenosis," Advanced Drug Delivery Reviews, vol. 24, pp. 3-9, (1997).

Oxford Applied Research, "Nanocluster Deposition Systems—Nanodep60," [first downloaded Nov. 3, 2006], (http://www.oaresearch.co.uk.nanodep60.htm).

Paik et al., "Micromachining of mesoporous oxide films for microelectromechanical system structures," Journal of Materials Research, vol. 17, pp. 2121-2129, (2002).

Palasis et al., "Analysis of Adenoviral Transport Mechanisms in the Vessel Wall and Optimization of Gene Transfer Using Local Delivery Catheters," Human Gene Therapy, vol. 11, pp. 237-246, Jan. 20, 2000.

Palasis et al., "Site-Specific Drug Delivery from Hydrogel Coated Angioplasty Catheters," Proceedings of the International Symposium on Controlled Release: Bioactive Materials, vol. 24, pp. 825-826, (1997).

Palmaz et al., "Influence of surface topography on endothelialization of intravascular metallic material," Journal of Vascular and Interventional Radiology, vol. 10, No. 4, pp. 439-444, (1999).

Pang et al., "Electrodeposition of composite hydroxyapatite-chitosan films," Materials Chemistry and Physics, vol. 94, pp. 245-251, (2005).

Pang et al., "Electropolymerization of high quality electrochromic poly(3-alkyl-thiophene)s via a room ternmperature ionic liquid," Electrochimica Acta, vol. 52, pp. 6172-6177, (2007).

Park et al., "Multilayer Transfer Printing for Polyelectrolyte Multilayer Patterning. Direct Transfer of Layer-by-Layer Assembled Micropatterned Thin Films," Advanced Materials, vol. 16, No. 6, pp. 520-525, Mar. 18, 2004.

Park et al., "Novel Phenylethynyl Imide Silanes as Coupling Agents for Titanium Alloy," The 22nd Annual Meeting of the Adhesion Society, Feb. 21-24, 1999.

Park et al., "Cathodic electrodeposition of $RuO_2$ thin films from $Ru(III)Cl_3$ solution", Materials Chemistry and Physics, vol. 87, pp. 59-66, (2004).

Park et al., "Microstructural change and precipitation hardeningin melt-spun Mg-X-Ca alloys," Science and Technology of Advanced Materials, vol. 2, pp. 73-78, (2001).

Pathan et al., "A chemical route to room-temperature synthesis of nanocrystalline TiO2 thin films," Applied Surface Science, vol. 246, pp. 72-76, (2005).

Pelletier et al., "Plasma-based ion implantation and deposition: A review for physics, technology, and applications," Lawrence Berkeley and National Laboratory, pp. 1-68, May 16, 2005.

Peng et al., "Role of polymers in improving the results of stenting in coronary arteries," Biomaterials, vol. 17, No. 7, pp. 658-694 (1996).

Perlman et al., "Evidence for rapid onset of apoptosis in medial smooth muscle cells after balloon injury," Circulation, vol. 95, No. 4, pp. 981-987, Feb. 18, 1997.

Pharmaceutical Science Technology, Chapter 6: Electropolymerization, pp. 24-28, (2007).
Piazza et al., "Protective diamond-like carbon coatings for future optical storage disks," Diamond & Related Materials, vol. 14, pp. 994-999, (2005).
Pitt et al., "Attachment of hyaluronan to metallic surfaces," Journal of Biomedical Materials Research, vol. 68A, pp. 95-106, (2004).
Polygenetics, "Advanced Drug Delivery," [first downloaded on May 4, 2007], 5 pages, (http://www.polygenetics.com/drug_delivery.htm).
Ponte et al., "Porosity determination of nickel coatings on copper by anodic voltammetry," Journal of Applied Electrochemistry, vol. 32, pp. 641-646, (2002).
Prior Clinicals, Boston Scientific memo, (more than a year prior to May 23, 2007).
Prokopowicz et al., "Synthesis and Application of Doxorubicin-Loaded Silica Gels as Solid Materials for Spectral Analysis," Talanta, vol. 65, pp. 663-671, (2005).
Prokopowicz et al., "Utilization of Standards Generated in the Process of Thermal Decomposition Chemically Modified Silica Gel or a Single Point Calibration of a GC/FID System," Talanta, vol. 44, pp. 1551-1561, (1997).
Pulsed Laser Deposition, (http://www.physandtech.net), Apr. 28, 2001.
PVD Materials—Materials Available for Physical Vapour Deposition (PVD) from Williams Advanced Materials. (www.azom.com), [first downloaded Apr. 28, 2006].
Qasem et al., "Kinetics of Paclitaxel 2'-N-Methylpyridinium Mesylate Decomposition," AAPS PharmaSciTech, vol. 4, No. 2, Article 21, (2003).
Qian et al., "Preparation, characterization and enzyme inhibition of methylmethacrylate copolymer nanoparticles with different hydrophilic polymeric chains," European Polyer Journal, vol. 42, pp. 1653-1661, (2006).
Qiang et al., "Hard coatings (TiN, $Ti_xAl_{1-x}N$) deposited at room temperature by energetic cluster impact," Surface and Coatings Technology, 100-101, pp. 27-32, (1998).
Qiu et al., "Self-assembled growth of MgO nanosheet arrays via a micro-arc oxidations technique," Applied Surface Science vol. 253, pp. 3987-3990, (2007).
Radin et al., "Biocompatible and Resorbable Silica Xerogel as a Long-Term Controlled Release Carrier of Vancomycin," Orthopaedic Research Society, 47th Annual Meeting, Feb. 25-28, 2001, San Francisco, CA.
Radin et al., "Silica sol-gel for the controlled release of antibiotics. I. Synthesis, characterization, and in vitro release," Journal of Biomedical Materials Research, vol. 27, No. 2, pp. 313-320, Nov. 2001.
Radin, S. et al., "In vitro bioactivity and degradation behavior of silica xerogels intended as controlled release materials," Biomaterials, vol. 23, No. 15, pp. 3113-3122, Aug. 2002.
Radtchenko et al., "A Novel Method for Encapsulation of Poorly Water-Soluble Drugs: precipitation in Polyelectrolyte multilayer shells", International Journal of Pharmaceutics, vol. 242, pp. 219-223, (2002).
Razzacki et al., "Integrated microsystems for controlled drug delivery," Advanced Drug Delivery Reviews, vol. 56, pp. 185-198, (2004).
Rees et al., "Glycoproteins in the Recognition of Substratum by Cultured Fibroblasts," Symposia of the Society for Experimental Biology: Cell-Cell Recognition, No. 32, pp. 241-260 (1978).
Reyna-Gonzales et al., "Influence of the acidity level on the electropolymerization of N-vinylcarbazole: Electrochemical study and characterization of poly(3,6-N-vinylcarbazole)," Polymer, vol. 47, pp. 6664-6672, (2006).
Rice, "Limitations of pore-stress concentrations on the mechanical properties of porous materials," Journal of Material Science, vol. 32, pp. 4731-4736, (1997).
Ristoscu, "Thin Films and Nanostructured Materials." [first downloaded Jul. 3, 2003], (http://www..fisica.unile.it/radiazioni/ThinY02Ofilms%20and%20nanostmctured%20materials.htm).
Robbie et al., "Advanced techniques for glancing angle deposition," Journal of Vacuum Science and Technology B, vol. 16, No. 3, pp. 1115-1122, (May/Jun. 1998).
Robbie et al., "Sculptured thin films and glancing angle deposition: Growth mechanics and applications," Journal of Vacuum Science Technology: A., vol. 15, pp. 1460-1465, (1997).
Roder et al., "Tuning the microstructure of pulsed laser deposited polymer-metal nanocomposites," Applied Physics A. vol. 85, pp. 15-20 (2006).
Roder et al., "Tuning the microstructure of pulsed laster deposited polymer-metal nanocomposites," Applied Physics A, vol. 85, pp. 15-20, (2006).
Rosen et al., "Fibrous Capsule Formation and Fibroblast Interactions at Charged Hydrogel Interfaces," Hydrogels or Medical and Related Applications, Chapter 24, pp. 329-343, Jun. 1, 1976.
Rossi et al., "Pulsed Power Modulators for Surface Treatment by Plasma Immersion Ion Impantation," Brazilian Journal of Physics, vol. 34, No. 4B, Dec. 2004.
Rossi et al., "Pulsed Power Modulators for Surface Treatment by Plasma Immersion Ion Implantation" Brazilian Journal of Physics, vol. 34, No. 4B, pp. 1565-1571, Dec. 2004.
Routkevitch, "Nano- and Microfabrication with Anodic Alumina: A Route to Nanodevices," Foresight Institute 9th Conference on Molecular Nanotechnology, Nov. 8-11, 2001, Santa Clara, CA.
Ryu et al., "Biomimetic apatite induction on Ca-containing titania," Current Applied Physics, vol. 5, pp. 512-515, (2005).
Santos et al., "Si-Ca-P xerogels and bone morphogenetic protein act synergistically on rat stromal marrow cell differentiation in vitro," Journal of Biomedical Materials Research, vol. 41, No. 1, pp. 87-94, Jul. 1998.
Santos et al., "Sol-Gel Derived Carrier for the Controlled Release of Proteins," Biomaterials, vol. 20, pp. 1695-1700, (1999).
Sardella et al., "Plasma-Aided Micro- and Nanopatterning Processes for Biomedical Applications," Plasma Processes and Polymers, vol. 3, pp. 456-469, (2006).
Sasahara et al., "Macroporous and nanosized ceramic films prepared by modified sol-gel methods with PMMA microsphere templates," Journal of the European Ceramic Society, vol. 24, pp. 1961-1967, (2004).
Sawitowski, "Nanoporous alumina for implant coating—Anovel approach towards local therapy," NanoMed 3rd Workshop, Medical Applications of Nanotechnology, Berlin, Feb. 17-18, 2003.
Sawyer et al., "The Role of Electrochemical Surface Properties in Thrombosis at Vascular Interfaces: Cumulative Experience of Studies in Animals and Man," Bulletin of the New York Academy of Medicine, Second Series, vol. 48, No. 2, pp. 235-256, (1972).
Sawyer, "Electrode-Biologic Tissue Interreactions at Interfaces—AReview;" Biomat. Med. Dev. Art. Org., 12(3-4), pp. 161-196 (1984).
Schetsky, "Shape Memory Alloys", Encyclopedia of Chemical Technology (3rd ed.), John Wiley & Sons, vol. 20, pp. 726-736, (1982).
Schlottig et al., "Characterization of nanoscale metal structures obtained by template synthesis," Fresenius' Journal of Analytical Chemistry, vol. 361, pp. 684-686, (1998).
Schneider, "Laser Cladding with Powder: Effect of some machining parameters on clad properties," Doctoral Thesis—University of Twente, The Netherlands, ISBN 9036510988, Mar. 1998.
Schnitzler et al., "Organic/Inorganic Hybrid Materials Formed From $TiO_2$ Nanoparticles and Polyaniline," Journal of Brazilian Chemistry Society, vol. 15, No. 3, pp. 378-384, (2004).
Selective laser sintering, from Wikipedia, (http://en.wikipedia.org/wiki/Selective_laser_sintering), downloaded on Sep. 28, 2007.
Senior et al., "Synthesis of tough nanoporous metals by controlled electrolytic dealloying," Nanotechnology, vol. 17, pp. 2311-2316, (2006).
Serra et al., "Preparation of functional DNA microarrays through laser-induced forward transfer," Applied Physics Letters, vol. 85, No. 9, pp. 1639-1641, Aug. 30, 2004.
Serruys et al., "The Effect of Variable Dose and Release Kinetics on Neointimal Hyperplasia Using a Novel Paclitaxel—Eluting Stent Platform," Journal of the American College of Cardiology, vol. 46, No. 2, pp. 253-260, Jul. 19, 2005.
Sgura et al., The Lunar Stent: characteristics and clinical results, Herz, vol. 27, pp. I -X, (2002).
Shabalovskaya et al., "Surface Conditions of Nitinol Wires, Tubing, and As-Cast Alloys. The Effect of Chemical Etching, Aging in Boiling Water, and Heat Treatment," Wiley Periodicals, Inc., Journal of Biomedical Materials Research Part B: Appiled Biomaterials, vol. 65B: pp. 193-203, (2003).
Shamiryan et al., "Comparative study of SiOCH low-k films with varied porosity interacting with etching and cleaning plasma," Journal of Vacuum Science Technology B, vol. 20, No. 5, pp. 1923-1928, Sep./Oct. 2002.
Shang et al., "Structure and photocatalytic characters of TiO2 film photocatalyst coated on stainless steel webnet," Journal of Molecular Catalysis A: Chemical, vol. 202, pp. 187-1995, (2003).
Shao et al., "Fiber mats of poly(vinyl alcohol)/silica composite via Electrospinning," Materials Letters, vol. 57, pp. 1579-1584, (2003).
Shchukin et al., "Micron-scale hollow polyelectrolyte capsules with naosized magnetic $Fe_3O_4$ inside," Materials Letters, vol. 57, pp. 1743-1747, (2003).
Shevchenko et al., "Porous Surface of NiTi Alloy Produced by Plasma Ion Implantation," Institute of Ion Beam Physics and Materials Research, May 2005.
Shevchenko, "Formation of nonoporous structures on stainless steel surface," Report, Apr. 2007.
Shibli et al., "Development of phosphate inter layered hydroxyapatite coating for stainless steel implants", Applied Surface Science, vol. 254, pp. 4103-4110, (2008).
Shockravi et al., "Soluable and thermally stable polyamides bearing 1,1'-thiobis(2-naphthoxy) groups," European Polymer Journal, vol. 43, pp. 620-627, (2007).
Shustak et al., "*n*-Alkanoic Acid Monolayers on 316L Stainless Steel Promote the Adhesion of electropolymerized Polypyrrole Films," Langmuir, vol. 22, pp. 5237-5240, (2006).
Siegfried et al., "Reactive Cylindrical Magnatron Deposition of Titanium Nitride and Zirconium Nitride Films," Society of Vacuum Coaters, 39th Annual Technical Conference Proceedings, pp. 97-101, (1996).
Silber et al., "A new stainless-steel-free stent with a potential of artifact free magnetic resonance compatibility: first clinical experience (Ein neuer Edelstahl-freier Stent mit Potential zur artefaktfreien MR-Kompatibilität: Erste klinische Erfahrungen)," German Society for Cardiology—Heart and Cardiovascular Research (Deutche Gesellschaft fur Kardiologie—Herz and Kreislaufforschung), Oct. 30, 2005.
Silber et al., "A new stainless-steel-free stent with a potential of artifact free magnetic resonance compatibility: first clinical experience," Abstract and Poster, May 2006.
Silber, " LUSTY-FIM Study: Lunar Starflex First in Man Study, " PowerPoint presentation at the Paris Course on Revascularization, May 2003.
Silber, "Ein edelstahfreier stent aus niobium mit iridiumoxyd (IrOx)-beschichtung: Erste Ergebnisse der LUSTY-studie" (*Stainless steel-free Stent out of niobium with iridiumoxyd (IrOx)-coating: Initial results of the LUSTY-study*), PowerPoint presentation on Oct. 15, 2004.
Silber, "LUSTY-FIM Study: Lunar Starflex First in Man Study," PowerPoint presentation in 2003.
Silber, "Niobium/iridiumoxide Stents: LUSTY randomized trial, Lunar Rox registry," PowerPoint presentation in 2003.
Silva et al., "Electrochemical characterisation of oxide films formed on Ti-6A1-4V alloy implanted with Ir for Bioengineering applications," Electrochimica Acta, vol. 43, Nos. 1-2, pp. 203-211, (1998).
Simon et al., "Influence of topography on endothelialization of stents: Clues for new designs," Journal of Long-Term Effects Of Medical Implants, Voo. 10, No. 1-2, pp. 143-151, (2000).
Singer, "Paclitaxel Poliglumex (XYOTAX, CT-2103): A Macromolecular Taxane," Journal of Controlled Release, vol. 109, 120-126, (2005).
Singh et al., "Review: Nano and macro-structured component fabrication by electron beam-physical vapor deposition (EB-PVD)," Journal of Materials Science, vol. 40, pp. 1-26, (2005).
Sniadecki et al., "Nanotechnology for Cell-Substrate Interactions," Annals of Biomedical Engineering, vol. 34, No. 1, pp. 59-74, Jan. 1, 2006.
Sofield et al., "Ion beam modification of polymers," Nuclear Instruments and Methods in Physics Research, vol. B67, pp. 432-437, (1992).
Soler-Illia et al., "Block Copolymer-Templated Mesoporous Oxides," Current Opinion in Colloid and Interface Science, vol. 8, pp. 109-126, (2003).
Song et al., "Biomimetic apatite coatings on micro-arc oxidized titania," Biomaterials, vol. 25, pp. 3341-3349, (2004).
Sousa et al., "New Frontiers in Cardiology: Drug-Eluting Stents: Part I," Circulation: Journal of the Americal Heart Associate, vol. 107, pp. 2274-2279, http/www.circ.ahajournals.org, (2003).
Sousa et al., "New Frontiers in Cardiology: Durg-Eluting Stents: Part I," Circulation, vol. 107, pp. 2274-2279, (2003).
Spasova et al., "Magnetic and optical tunable microspheres with a magnetite/gold nanoparticle shell," Journal of Material Chemisty, vol. 115, pp. 2095-2098, (2005).
Sprague et al., "Endothelial cell migration onto metal stent surfaces under static and flow conditions," Journal of Long-Term Effects of Medical Implants, vol. 10, No. 1-2, pp. 97-110, (2000).
Startschuss fur "lusty" -studie, (*Launch of "lusty" -study*), Cardio News, Oct. 2002.
Stucky "High Surface Area Materials," Published: Jan. 1998, WTEC Hyper-Librarian, (http://www.wtec.org/loyola/nano/US.Review/07_03.htm).
Studart et al., "Colloidal Stabilization of Nanoparticles in Concentrated Suspensions," Langmuir, vol. 23, pp. 1081-1090, (2007).
Sun et al., "Construction of Size-Controllable Hierarchical Nanoporous $TiO_2$ Ring Arrays and Their Modifications," Chem. Mater, vol. 18, pp. 3774-3779, (2006).
Sun et al., "Non-Fouling Biomaterial Surfaces: II Protein Adsorption on Radiation Grafted Polyethylene Glycol Methacrylate Copolymers," Polymer Preprints, vol. 28, No. 1, pp. 292-294, Apr. 1987.
Sundararajan et al., "Mechanisms underlying the formation of thick alumina coatings through the MAO coating technology," Surface and Coatings Technolgy, vol. 167, pp. 269-277, (2003).
Sung et al., "Formation of Nanoporous and Nanocrystalline Anatase Films by Pyrolysis of $PEO-TiO_2$ Hybrid Films," Journal of Crystal Growth, vol. 286, pp. 173-177, (2006).
Szycher et al., "Drug-Eluting Stents to Prevent Coronary Restenosis," CardioTech International, (2002).
Tabata et al., "Generalized Semiempirical Equations for the Extrapolated Range of Electronics," Nuclear Instruments and Methods, vol. 103, pp. 85-91, Mar. 28, 1972.
Takitani et al., "Desorption of Helium from Austenitic Stainless Steel Heavily Bombarded by Low Energy He Ions," Journal of Nuclear Materials, vol. 329-333, pp. 761-765, (2004).
Tamura et al., "Surface Hydroxyl Site Densities on Metal Oxides as a Measrure for the Ion-Exchange Capacity," Journal of Colloid and Interface Science, vol. 209, pp. 225-231, (1999).
Tan et al., "Corrosion and wear-corrosion behavior of NiTi modified by plasma source ion implantation," Biomaterials, vol. 24, pp. 3931-3939, (2003).
Tanaka et al., "Micrometer-scale fabrication and assembly using focused ion beam," Thin Solid Films, vol. 509, pp. 113-117, (2006).
Tang et al., "Electrochemical Study of a Polarized Electrochemical Vapor Deposition Process," Journal of The Electrochemical Society, vol. 147, No. 9, pp. 3338-3344, (2000).
Tang et al., "Fabrication of Macroporous Alumina with Tailored Porosity," Jornal of American Ceramic Society, vol. 86, No. 12, pp. 2050-2054, (2003).
Tang et al., "Preparation of Porous anatase titania film," Materials Letters, vol. 58, pp. 1857-1860, (2004).
Tapphorn et al., "The Solid-State Spray Forming of Low-Oxide Titanium Components," Journal of Metals, vol. 50, No. 9, pp. 45-46,76, (1998).
Tassin et al., "Improvement of the Wear Resistance of 316 L Stainless Steel by Laser Surface Alloying," Surface and Coatings Technology, vol. 80, No. 9, pp. 207-210, (1996).
Terlingen, "Functionalization of Polymer Surfaces," Europlasma Technical Paper, pp. 1-29, May 8, 2004.
Terumo Europe, "Terumo Europe N.V. Enrols First Patient in Clinical Trial of the Nobori Drug-Eluting Coronary Stent," Press Release May 26, 2005, (http://www.terumo-europe.com/_press_release/may_26_2005.html.).

Thierry et al., "Bioactive Coatings of Endovascular Stents Based on Polyelectrolyte Multilayers," Biomacromolecules, vol. 4, pp. 1564-1571, (2003).

Thompson et al., "Tuning compliance of nanoscale polyelectrolyte multilayers to modulate cell adhesion," Biomaterials, vol. 26, pp. 6836-6845, (2005).

Tierno et al., "Using Electroless Deposition for the Preparation of Micron Sized Polymer/Metal Core/Shell Particles and Hollow Metal Spheres," Journal of Physics Chemistry B, vol. 110, pp. 3043-3050, (2006).

Tollon, "Fabrication of coated biodegradable polymer scaffolds and their effects on murin embryonic stem cells," Thesis presented to the University of Florida, (2005).

Tonosaki et al., "Nano-indentation testing for plasma-based ion-implanted surface of plastics," Surface and Coatings Technology, vol. 136, pp. 249-251, (2001).

Tones-Costa et al., "RBS Characterization of Porous Silicon Multilayer Interference Filters," Electrochemical and Solid-State Letters, vol. 7, No. 11, pp. G244-G249 (2004).

Toth et al., "Ar+laser-induced forward transfer (LIFT): a novel method for micrometer-size surface patterning," Applied Surface Science, vol. 69, pp. 317-320, (1993).

Tsyganov et al., "Blood compatibilty of titanium-bases coatings prepared by metal plasma immersion ion implantation and deposition," Applied Surface Science, vol. 235, pp. 156-163, (2004).

Tsyganov et al., "Structure and Properties of Titanium Oxide Layers prepared by Metal Plasma Immersion Ion Implantation and Deposition," Surface & Coatings Technology, vol. 174-175, pp. 591-596, (2003).

Tsyganov et al., "Correlation between blood compatibility and physical surface properties of titanium-based coatings," Surface & Coatings Technology, vol. 200, pp. 1041-1044, (2005).

Uchida et al., "Apatite-forming ability of a zirconia/alumina nanocomposite induced by chemical treatment," Journal of Biomedical Materials Research, vol. 60, No. 2, pp. 277-282, May 2002.

University of Wisconsin, "Effect of Nano-Scale Textured Biomimetic Surfaces on Proliferation and Adhesion of Corneal Epithelial Cells," Materials Research Science and Engineering Center, (1997), (http://mrsec.wisc.edu/Past_proiects/seedproi4/Seedproi4.html).

Uyama et al., "Surface Modifications of Polymers by Grafting," Advances in Polymer Science, vol. 139, (1998).

Valsesia et al., "Selective immobilization of protein clusters on polymeric nanocraters," Advanced Functional Materials, vol. 16, pp. 1242-1246, (2006).

Valsesia, A. et al., "Fabrication of nanostructured polymeric surfaces for biosensing devices," Nanoletters, vol. 4, No. 6, pp. 1047-1050, (2004).

Van Alsten, "Self-Assembled Monolayers on Engineering Metals: Structure, Derivatization, and Utility," Langmuir, vol. 15, pp. 7605-7614, (1999).

Van Den Berg, "Nano particles play with electrons," [first downloaded on Nov. 12, 2003], (http://www.delftoutlook.tudelft.nl/info/index21fd.html?hoofdstuk=Article&ArtID=2243).

van der Eijk et al., " Metal Printing Process Development of a New Rapid Manufacturing Process for Metal Parts," Proceedings of the World PM2004 Conference held in Vienna, Oct. 17-21, 2004.

Van Steenkiste et al., "Kinetic spray coatings," Surface & Coatings Technology, vol. 111, pp. 62-71, (1999).

Vayssieres, "On the design of advanced metal oxide nanomaterials," International Journal of Nanotechnology, vol. 1, Nos. 1/2, (2004).

Velev et al., "Colloidal crystals as templates for porous materials," Current Opinion in Colloid & Interface Science, vol. 5, pp. 56-63, (2000).

Velev et al., "Porous silica via colloidal crystallization," Nature, vol. 389, pp. 447-448, Oct. 2, 1997.

Verheye et al., "Reduced Thrombus Formation by Hyaluronic Acid Coating of Endovascular Devices," Arteriosclerosis, Thrombosis, and Vascular Biology: Journal of The American Heart Association, vol. 20, pp. 1168-1172, (2000).

Vidal et al., "Electropolymerization of pyrrole and immobilization of glucose oxidase in a flow system: influence of the operating conditions on analytical performance," Biosensors & Bioelectronics, vol. 13, No. 3-4, pp. 371-382, (1998).

Vigil et al., "TiO2 Layers Grown from Flowing Precursor Solutions Using Microwave Heating," Langmuir, vol. 17, pp. 891-896, (2001).

Viitala et al., "Surface properties of in vitro bioactive and non-bioactive sol-gel derived materials," Biomaterials, vol. 23, pp. 3073-3086, (2002).

Vitte et al., "Is there a predictable relationship between surface physical-chemical properties and cell behaviour at the interface?" European Cells and Materials, vol. 7, pp. 52-63, (2004).

Volkel et al., "Electrodeposition of coppper and cobalt nanostructures using self-assembled monolayer templates," Surface Science, vol. 597, pp. 32-41, (2005).

Vu et al., "Eletrophoretic deposition of nanocomposites formed from polythiophene and metal oxides," Electrochimica Acta, vol. 51, pp. 1117-1124, (2005).

Vuković et al., "Anodic stability and electrochromism of electrodeposited ruthenium-iridium coatings on titanium," Journal of Electroanalytical Chemisty, vol. 330, pp. 663-673 (1992).

Walboomers et al., "Effect of microtextured surfaces on the performance of percutaneous devices," Journal of Biomedical Materials Research Part A, vol. 74A, No. 3, pp. 381-387, (2005).

Wang et al., "Deposition of in-plane textured MgO on amorphous $Si_3N_4$ substrates by ion-beamassisted deposition and comparisons with ion-beam-assistend deposidted yttria-stabilized-zirconia," Applied Physics Letters, vol. 71, No. 17, Issue 20, pp. 2955-2957, Nov. 17, 1997.

Wang et al., "Effect of substrate temperature on structure and electrical resistivity of laser ablated $IrO_2$ thin films," Applied Surface Science, vol. 253, pp. 2911-2914, (2006).

Wang et al., "Effect of the discharge pulsating on microarc oxidation coating formed on Ti6A14V alloy," Materials Chemistry and Physics, vol. 90, pp. 128-133, (2005).

Wang et al., "Novel Poly(3-nonylthiophene)-$TiO_2$ Hybrid Materials for Photovoltaic Cells," Synthetic Metals, vol. 155, pp. 677-680, (2005).

Wang et al., "Polyelectrolyte-Coated Colloid Spheres as Templates for Sol-Gel Reactions," Chem. Mater., vol. 14, pp. 1909-1913, (2002).

Wang et al., "Pulsed laser deposition of organic thin films," This Solid Films, vol. 363, pp. 58-60, (2000).

Wang et al., "Synthesis of Macroporous Titania and Inorganic Composite Materials from Coated Colloidal Spheres—A Novel Route to Tune Pore Morphology," Chem. Mater., vol. 13, pp. 364-371, (2001).

Webster et al."Enhanced functions of osteoblasts on nanophase ceramics," Biomaterials, vol. 21, No. 17, pp. 1803-1810, Sep. 2000.

Webster et al., "Increased osteoblast adhesion on nanophase metals: Ti, Ti6A14V, and CoCrMo," Biomaterials, vol. 25, No. 19, pp. 4731-4739, (2004).

Webster et al., "Specific proteins mediate enhanced osteoblast adhesion on nanophase ceramics," Journal of Biomedical Materials Research, vol. 5, No. 51, pp. 475-483, Sep. 2000.

Wei et al., "Structural Characterisation of Doped and Undoped Nanocrystalline Zinc Oxides Deposited by Ultrasonic Spray Assisted Chemical Vapour Deposition," Journal of Physics: Conference Series, vol. 26, pp. 183-186 (2006).

Wells, "Patterned Plasma Immersion Exposure of Insulating Materials for the Purpose of Modifying Optical Properties," thesis submitted to the college of William and Mary, Williamsburg, Vriginia, Apr. 2000.

Wesolowski et al., "Surface Charge and Ion Adsorption on Metal Oxides to 290° C," Division of Chemical Sciences, Geosciences, and Biosciences, Office of Basic Energy Sciences, U.S. Department of Energy, (2001).

Wessling et al., "RF-sputtering of iridium oxide to be used as stimulation material in functional medical implants," Journal of Micromechanics and Microengineering, vol. 16, pp. S142-S148 (2006).

Whelan, "Targeted Taxane Therapy for Cancer," Drug Discovery Today, vol. 7, No. 2, pp. 90-92, Jan. 2002.

Which stent is right for you? (circa 2004).

Wieneke et al., "Synergistic Effects of a Novel Nanoporous Stent Coating and Tacrolimus on Intima Proliferation in Rabbits," Catheterization and Cardiovascular Interventions, vol. 60, pp. 399-407, (2003).

Wilkinson et al., "Nanofabrication in cellular engineering," Journal of Vacuum Science & Technology B, vol. 16, No. 6, pp. 3132-3136, (1998).

Wilkinson et al., "The use of materials patterned on a nano- and micro-metric scale in cellular engineering," Materials Science & Engineering C, vol. 19, No. 1-2, pp. 263-269, (2002).

Wilson et al., "Mediation of biomaterial-cell interactions by adsorbed proteins: A review," Tissue Engineering, vol. 11, No. 1-2, pp. 1-18, (2005).

Wong et al., "Balance of chemistry, topography, and mechanics at the cell-biomaterial interface: Issues and challenges for assessing the role of substrate mechanics on cell response," Surface Science, vol. 570, No. 1-2, pp. 119-133, (2004).

Wong et al., "Polymer segmental alignment in polarized pulsed laser-induced periodic surface structures," Applied Physics A, vol. 65, pp. 519-523, (1997).

Wood, "Next-generation drug-eluting stents tackle shortcomings of Cypher, Taxus," Heart Wire, Feb. 7, 2006, (http://www.theheart.org/article/641591.do.).

World Reference definition, "Interconnected," WorldReference.com, [downloaded Jan. 21, 2010].

Wu et al., "Characterization of Mesoporous Nanocrystalline $TiO_2$ Photocatalysts Synthesized Via a Sol-Solvothermal Process at a Low Temperature," Journal of Solid State Chemistry, vol. 178, pp. 321-328, (2005).

Wu et al., "Chitosan-Mediated and Spatially Selective Electrodeposition of Nanoscale Particles," Langmuir, vol. 21, pp. 3641-3646, (2005).

Wu et al., "Corrosion resistance of $BaTiO_3$ films prepared by plasma electrolytic oxidation," Surface and Coatings Technology, vol. 166, pp. 31-36, (2002).

Wu et al., "Design of Doped Hybrid Xerogels for a Controlled Release of Brilliant Blue FCF," Journal of Non-Crystalline Solids, vol. 342, pp. 46-53, (2004).

Wu et al., "The effects of cathodic and anodic voltages on the characteristics of purous nanocrystalline titania coatings fabricated by microarc oxidation," Materials Letters, vol. 59, pp. 370-375, (2005).

Xia et al., "Monodispersed Colloidal Spheres: Old Materials with New Applications," Advanced Materials, vol. 12, No. 10, pp. 693-713, (2000).

Xu et al., "An Improved Method to Strip Aluminum from Porous Anodic Alumina Films," Langmuir, vol. 19, pp. 1443-1445, (2003).

Xu et al., "Cold spay deposition of thermoplastic powder," Surface & Coatings Technology, vol. 2001, pp. 3044-3050, (2006).

Xu et al., "Synthesis of porosity controlled ceramic membranes," Journal of Material Research, vol. 6, No. 5, pp. 1073-1081, May 1991.

Yamato et al. "Nanofabrication for micropatterned cell arrays by combining electron beam-irradiated polymer grafting and localized laser ablation," Journal of Biomedical Materials Research, vol. 67, No. 4, pp. 1065-1071, Dec. 15, 2003.

Yan et al., "New MOCVD precursor for iridium thin films deposition," Materials Letters, vol. 61, pp. 216-218, (2007).

Yan et al., "Sol-gel Processing," Handbook of Nanophase and Nanostructured Materials, vol. 1: Synthesis, Chapter 4, (2003).

Yang et al., "Laser spray cladding of porous NiTi coatings on NiTi substrates," The Hong Kong Polytechnic University, Dec. 28, 2006.

Yang et al., "Poly($_{L,L}$-lactide-$co$-glycolide)/tricalcium phosphate composite scaffold and its various changes during degradation in vitro," Polymer Degradation and Stability, vol. 91 pp. 3065-3073, (2006).

Yang et al., "Thermal oxidation products and kinetics of polyethylene composites," Polymer Degradation and Stability, vol. 91, pp. 1651-1657, (2006).

Yang et al., "Solution phase synthesis of magnesium hydroxide sulfate hydrate nanoribbons", Nanotechology, vol. 15, pp. 1625-1627, (2004).

Yankov et al., "Reactive plasma immersion ion implantation for surface passivation," Surface and Coatings Technology, vol. 201, pp. 6752-6758, (2007).

Yap et al., "Protein and cell micropatterning and its integration with micro/nanoparticles assembley," Biosensors and Bioelectronics, vol. 22, pp. 775-788, (2007).

Yerokhin et al., "Kinetic aspects of aluminium titanate layer formation on titanium alloys by plasma electrolytic oxidation," Applied Surface Science, vol. 200, pp. 172-184, (2002).

Yerokhin et al., "Plasma electrolysis for surface engineering," Surface Coatings Technology, vol. 122, pp. 73-93, (1999).

Yim et al., "Nanopattern-induced changes in morphology and motility of smooth muscle cells," Biomaterials, vol. 26, pp. 5405-5413, (2005).

Yim et al., "Significance of synthetic nanostructures in dictating cellular response," Nanomedicine: Nanotechnology, Biology and Medicine, vol. 1, No. 1, pp. 10-21, Mar. 1, 2005.

Yoldi et al., "Electrophoretic deposition of colloidal crystals assisted by hydrodynamic flows," Journal of Materials Science, vol. 41, pp. 2964-2969, (2006).

Yoshida et al., "Impact of Low Energy Helium Irradiation on Plasma Facing Metals," Journal of Nuclear Materials, vol. 337-339, pp. 946-950, (2005).

Young et al., "Polarized electrochemical vapor deposition for cermet anodes in solid oxide fuel cells," Solid State Ionics, vol. 135, pp. 457-462, (2000).

Yu et al., "Encapsulated cells: an atomic force microscopy study," Biomaterials, vol. 25, pp. 3655-3662, (2004).

Yu et al., "Enhanced photocatalytic activity of mesoporous and ordinary $TiO_2$ thin films by sulfuric acid treatment," Applied Catalysis B: Environmental, vol. 36, pp. 31, 43, (2002).

Yu et al., "Enhanced photoinduced super-hydrophilicity of the sol—gel-derived TiO2 thin films by Fe-doping," Materials Chemistry and Physics, vol. 95, pp. 193-196, (2006).

Yu et al., "Light-induced super-hydrophilicity and photocatalytic activity of mesoporous TiO2 thin films," Journal of Photochemistry and Photobiology A: Chemistry, vol. 148, pp. 331-339, (2002).

Yun et at., "Low-Temperature Coating of Sol-Gel Anatase Thin Films," Materials Letters, vol. 58, pp. 3703-3706, (2004).

Zakharian et al., "A Fullerene-Paclitaxel Chemotherapeutic: Synthesis, Characterization, and Study of Biological Activity in Tissue Culture," Journal of American Chemistry Society, vol. 127, pp. 12508-12509, (2005).

Zbroniec et al., "Laser ablation of iron oxide in various ambient gases," Applied Surface Science, vol. 197-198, pp. 883-886, (2002).

Zeng et al., "Biodegradable electrospun fibers for drug delivery," Journal of Controlled Release, vol. 92, pp. 227-231, (2003).

Zhang et al., "Surface analyses of micro-arc oxidized and hydrothermally treated titanium and effect on osteoblast behavior," Journal of Biomedical Materials Research, vol. 68A, pp. 383-391, (2004).

Zhang et al., "Surface treatment of magnesium hydroxide to improve its dispersion in organic phase by the ultrasonic technique", Applied Surface Science, vol. 253, pp. 7393-7397, (2007).

Zhao et al., "Coating deposition by the kinetic spray process," Surface & Coatings Technology, vol. 200, pp. 4746-4754, (2006).

Zhao et al., "Designing Nanostructions by Glancing Angle Deposition," Proceedings of SPIE, vol. 5219: Nanotubes and Nanowires, pp. 59-73, (2003).

Zhao et al., "Formulation of a ceramic ink for a wide-array drop-on-demand ink jet printer," Ceramics International, vol. 29, pp. 887-892, (2003).

Zheng et al., "Substrate temperature dependent morphology and resistivity of pulsed laser deposited iridium oxide thin films," Thin Solid Films, vol. 496, pp. 371-375, (2006).

Zheng et al., "Synthesis of Mesoporous Silica Materials via Nonsurfactant Templated Sol-Gel Route Using Mixture of Organic Compounds as Template," Journal of Sol-Gel Science and Technology, vol. 24. pp. 81-88, (2002).

Zhitomirsky et al., "Cathodic electrodeposition of MnOx films for electrochemical supercapacitors," Electrochimica Acta, vol. 51, pp. 3039-3045, (2006).

Zhitomirsky et al., "Electrodeposition of composite hydroxyapatite-chitosan films," Materials Chemistry and Physics, vol. 94, pages 245-251, (2005).

Zhou et al., "Branched Ta nanocolumns grown by glancing angle deposition," Applied Physics Letters, vol. 88, p. 203117, (2006).

Zoppi et al., "Hybrid Films of Poly(ethylene oxide-*b*-amide 6) Containing Sol-Gel Silicon or Titanium Oxide as Inorganic Fillers: Effect of Morphology and Mechanical Properties on Gas Permeability," Polymer, vol. 41, pp. 5461-5470, (2000).

Zou et al., "Highly textural lamellar mesostructured magnesium hydroxide via a cathodic electrodeposition process", Materials Letters, vol. 61, pp. 1990-1993, (2007).

Abstract: "Edelstahlfreier stent aus niobium mit iridiumoxyd (IrOx)-beschichtung: Erste Ergebnisse der LUSTY-studie", (Stainless steel-free Stent out of niobium with iridiumoxyd (IrOx)-coating: Initial results of the LUSTY-study), Annual Meeting of the German Society for Cardiology, Apr. 24-26, 2003.

Bu et al., "Preparation of nanocrystalline TiO2 porour films from terpineol-ethanol-PEG system," Journal of Materials Science, vol. 41, pp. 2067-2073, (2006).

\* cited by examiner

Coat Conformal Globular on Conformal Defined Grain

83 →

Insert Mandrel through Stent ID

85 →

Coat Defined Grain on OD

87 →

Remove Mandrel and Coat Conformal Globular

US 7,976,915 B2

ENDOPROSTHESIS WITH SELECT CERAMIC MORPHOLOGY

TECHNICAL FIELD

This disclosure relates to endoprostheses with select ceramic morphology.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen. Stent delivery is further discussed in Heath, U.S. Pat. No. 6,290,721, the entire contents of which is hereby incorporated by reference herein.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

SUMMARY

In an aspect, the invention features an endoprosthesis including ceramic having a morphology of defined grains with an aspect ratio of about 5:1 or more.

In another aspect, the invention features an endoprosthesis including ceramic having an Sdr of about 100 or greater.

In another aspect, the invention features an endoprosthesis including ceramic having a morphology of globular features having a height of about 20 nm or less, a diameter of about 100 nm or less, and a peak distance of about 200 nm or less.

In another aspect, the invention features an endoprosthesis including a ceramic having an Sdr of about 10 or less and an Sdr uniformity of about +/−10% on about 25% or more of an abluminal or adluminal surface.

In another aspect, the invention features an endoprosthesis including a ceramic having a morphology of defined grains, and a polymer coating over the ceramic.

In another aspect, the invention features an endoprosthesis including a ceramic coating having an Sdr of about 1 or more, and a polymer coating over the ceramic.

In another aspect, the invention features an endoprosthesis including a first ceramic having a morphology of defined grains on a first portion, and a second ceramic having a globular morphology.

In another aspect, the invention features an endoprosthesis including a first ceramic having an Sdr of about 10 or less, and a second ceramic having an Sdr of about 100 or more.

In another aspect, the invention features a method of forming a prosthesis including forming a ceramic by plasma sputtering, forming a polymer on the ceramic, and utilizing the polymer-coated ceramic in a stent.

In another aspect, the invention features a method of forming an endoprosthesis including forming a first ceramic having a first morphology on said endoprosthesis, and forming a second ceramic having a second morphology on said endoprosthesis.

Embodiments may also include one or more of the following features. The aspect ratio is about 10:1 to 20:1. The grains have a length from about 50 nm-400 nm. The grains have a width of about 5 to 15 nm. The ceramic has a peak distance of about 200 nm or less. The ceramic has a peak height of about 400 nm or less. The Sdr is about 120 to 200. The ceramic has an Sq of about 20 or more. The endoprosthesis includes a coating over the ceramic. The coating is formed of polymer. The coating includes drug. The ceramic is IROX.

Embodiments may also include one or more of the following features. The Sdr is about 120 to 200. The Sdr is about 150 or greater. The Sdr is about 180 or greater. The ceramic has an Sq of about 20 or more. The Sq is about 20 to 30. The Sdr a uniformity is about +/−20% or less. The ceramic includes defined grains having an aspect ratio of about 5:1 or more. The aspect ratio is about 10:1 to 20:1. The grains have a length from about 50 nm-200 nm. The grains have a width of about 5 to 15 nm.

The ceramic has a peak distance of about 400 nm or less. The ceramic has a peak height of about 400 nm or less.

Embodiments may also include one or more of the following features. The ceramic is a coating on a metal. The coating is on the abluminal side of a stent. The adluminal surface is substantially free of said coating. The ceramic has an Sq of about 10 or less. The ceramic has an Sq of about 10 or less. The coating is on the adluminal side of the endoprosthesis. The ceramic is exposed to tissue, free of an overcoat. The ceramic has an Sq of about 10 or less. The ceramic has a peak distance of about 200 nm or less. The ceramic has a peak height of about 200 nm or less. The ceramic has a peak distance of about 15 nm or less. The ceramic has a peak height of about 5 nm or less. The ceramic has a peak height of about 5 nm or less. The grains have an aspect ratio of about 5:1 or more. The Sdr is about 100 or greater. The Sdr is about 1 to 200.

Embodiments may also include one or more of the following features. The ceramic has a defined grain morphology. The ceramic has a globular morpholology. The first ceramic is on the abluminal side and the second ceramic is on the adluminal side. The coating over the second ceramic. The coating is polymer. The first ceramic is on top of the second ceramic. The second ceramic is on top of the first ceramic. The first ceramic is on the abluminal side and the second ceramic is on the adluminal side. The endoprosthesis includes a coating over the second ceramic. The coating is polymer. The polymer includes a drug. The second ceramic has a defined grain morphology. The first ceramic has a globular morphology.

Embodiments may also include one or more of the following. The ceramic has a morphology of defined grains with an aspect ratio of about 5:1 or more. The ceramic has a morphology of globular features having a height of about 20 nm or less, a diameter of about 100 nm or less, and a peak distance of about 200 nm or less. The ceramic has an Sdr of about 10 or less and an Sdr uniformity of about +/−10% about 25% or more of an abluminal or adluminal surface. The ceramic has a morphology of defined grains, and a polymer coating over the ceramic. The ceramic coating has an Sdr of about 1 or more, and a polymer coating over the ceramic. The first ceramic has a morphology of defined grains on a first portion, and a second ceramic having a morphology or globular features on a second portion. The first ceramic has an Sdr of about 10 or less, and the second ceramic has an Sdr of about 100 or more.

Embodiments may include one or more of the following advantages. Stents can be formed with ceramic coatings that have morphologies and/or compositions that enhance therapeutic performance. In particular, the ceramics are tuned to enhance mechanical performance and physiologic effect. Enhanced mechanical performance provides particular advantages during the challenging operations encountered in stent use, which typically includes collapsing the stent to a small diameter for insertion into the body, delivery though a tortuous lumen, and then expansion at a treatment site. Enhancing mechanical properties of the ceramic reduces the likelihood of cracking or flaking of the ceramic, and enhanced adhesion of the ceramic to the stent body and to overcoatings, such as drug eluting materials. Improved physiologic effects include discouraging restenosis and encouraging endothelialization. The ceramics are tuned by controlling ceramic morphology and composition. For example, the ceramic can have a morphology that enhances endothelial growth, a morphology that enhances the adhesion of overcoatings such as polymers, e.g. drug eluting coatings, a morphology that reduces delamination, cracking or peeling, and/or a morphology that enhances catalytic activity to reduce inflammation, proliferation and restenosis. The coverings can be tuned along a continuum of their physical characteristics, chemistries, and roughness parameters to optimize function for a particular application. Different coating morphologies can be applied in different locations to enhance different functions at different locations. For example, a high roughness, low coverage, defined-grain morphology can be provided on abluminal surfaces to enhance adhesion of a drug-eluting polymer coating and a low roughness, high coverage, globular morphology can be provided on the adluminal surface to enhance endothelialization. The composition is tuned to control hydrophobicity to enhance adhesion to a stent body or a polymer and/or control catalytic effects. The morphologies and composition can be formed by physical vapor deposition using methodologies that allow fine tuning of the morphology characteristics and permit highly uniform, predictable coatings across a desired region of the stent.

Still further aspects, features, embodiments, and advantages follow.

DETAILED DESCRIPTION

Figure 1A:
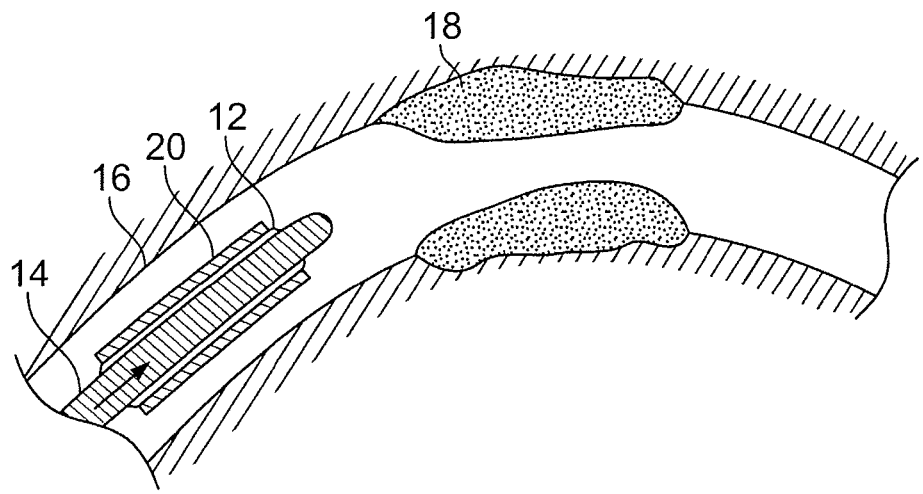
FIGS. 1A-1C are longitudinal cross-sectional views illustrating delivery of a stent in a collapsed state, expansion of the stent, and deployment of the stent.
Figure 1B:
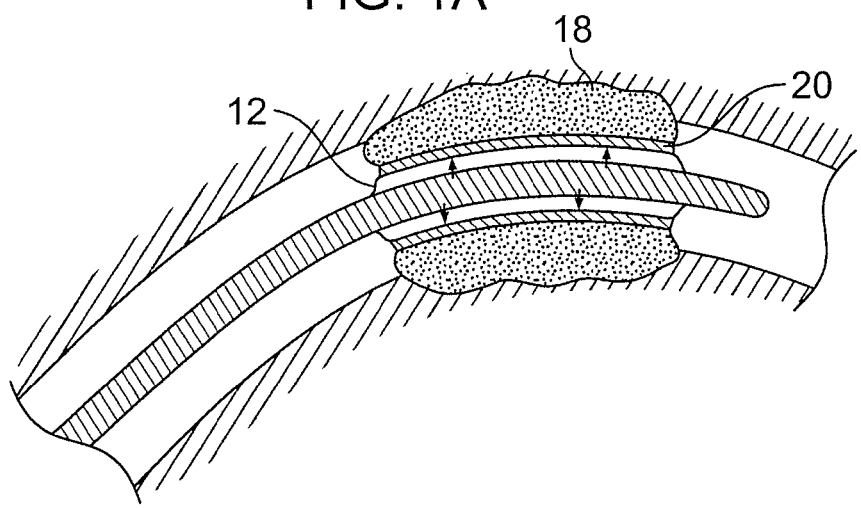
Figure 1C:
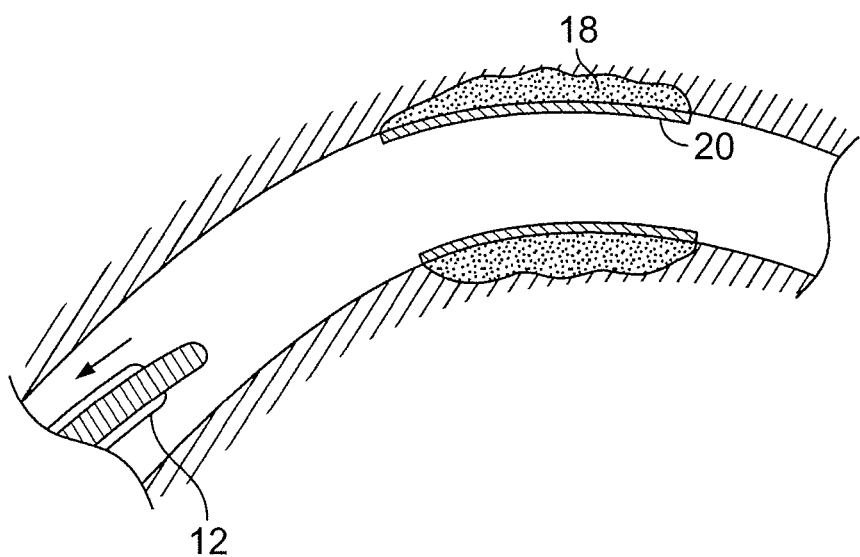

Referring to FIGS. 1A-1C, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2:
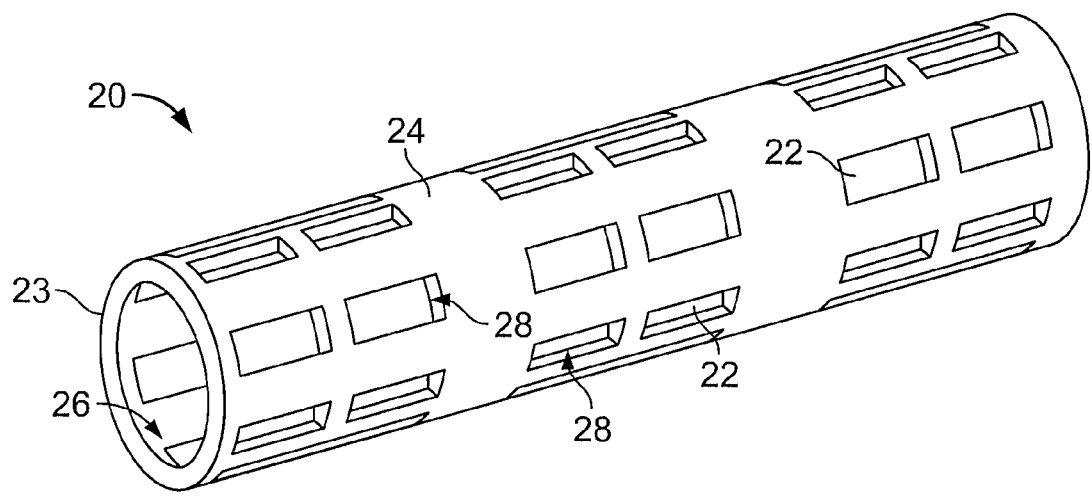
FIG. 2 is a perspective view of a stent.

Referring to FIG. 2, the stent 20 includes a plurality of fenestrations 22 between struts defined in a wall 23. Stent 20 includes several surface regions, including an outer, or abluminal, surface 24, an inner, adluminal, surface 26, and a plurality of cutface surfaces 28. The stent can be balloon expandable, as illustrated above, or self-expanding stent. Examples of stents are described in Heath '721, supra.

Figure 3:
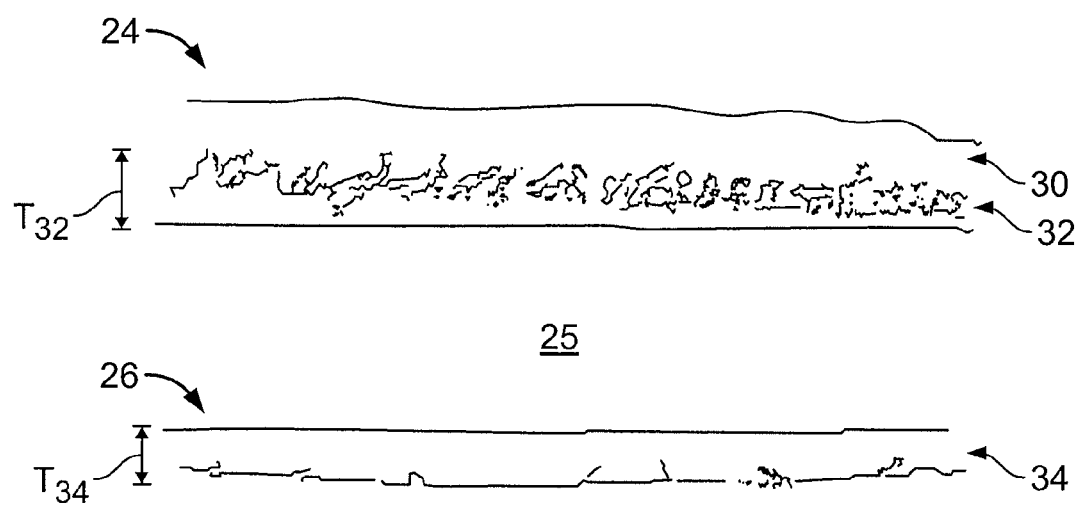
FIG. 3 is a cross-sectional view of a stent wall.

Referring to FIG. 3, an axial cross-sectional view, a stent wall 23 includes a stent body 25 formed, e.g. of a metal, and includes a first ceramic coating 32 on one side, e.g. the abluminal side, and a second ceramic coating 34 on the other side, e.g. the adluminal side. The abluminal side includes a second coating 36, such as a polymer that includes a drug. As illustrated, the coatings 32, 34 have different morphologies and roughnesses.

Figure 4A:
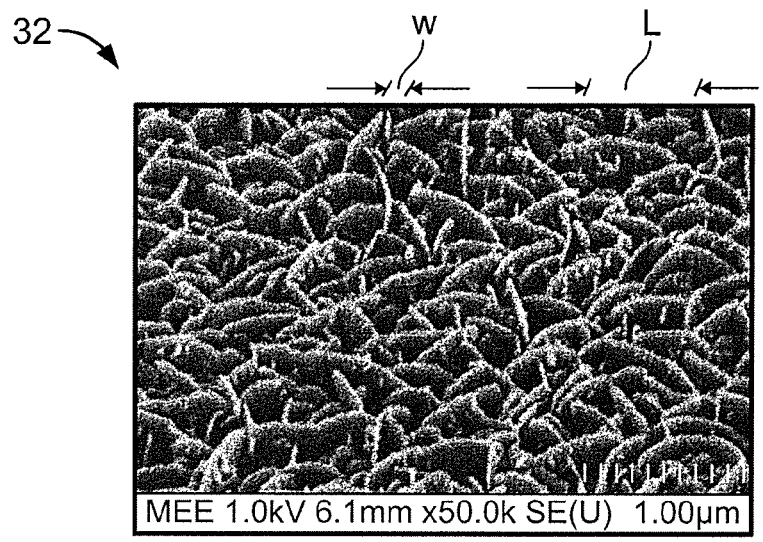
FIGS. 4A-4C are enlarged plan views of surface morphologies.

Referring as well to FIG. 4A, the coating 32 on the abluminal side includes a morphology characterized by defined grains and high roughness. The defined grain, high roughness morphology of the coating 32 provides a high surface area characterized by crevices between and around spaced grains into which the polymer coating 36 can be deposited and interlock to the surface, enhancing adhesion.

Figure 4B:
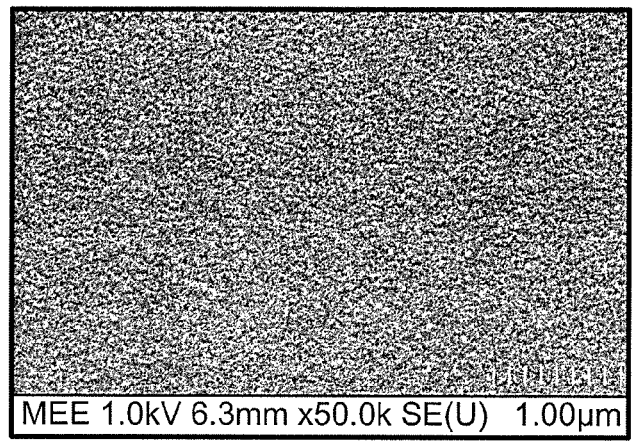

Referring as well to FIG. 4B, the coating 34 on the adluminal side has a morphology characterized by a higher coverage, globular surface of generally lower roughness. The smoother globular morphology provides a surface tuned to facilitate endothelial growth by selection of its chemical composition and/or morphological features.

The morphology and composition of the ceramic is selected for its mechanical characteristics, to enhance adhesion to the stent body and enhance adhesion of a polymer coating, for example, and/or to enhance therapeutic function such as reducing restenosis and enhancing endothelialization. Certain ceramics, e.g. oxides, can reduce restenosis through the catalytic reduction of hydrogen peroxide and other precursors to smooth muscle cell proliferation. The oxides can also encourage endothelial growth to enhance endothelialization of the stent. When a stent is introduced into a biological environment (e.g., in vivo), one of the initial responses of the human body to the implantation of a stent, particularly into the blood vessels, is the activation of leukocytes, white blood cells which are one of the constituent elements of the circulating blood system. This activation causes a release of reactive oxygen compound production. One of the species released in this process is hydrogen peroxide, $H_2O_2$, which is released by neutrophil granulocytes, which constitute one of the many types of leukocytes. The presence of $H_2O_2$ may increase proliferation of smooth muscle cells and compromise endothelial cell function, stimulating the expression of surface binding proteins which enhance the attachment of more inflammatory cells. A ceramic such as iridium oxide (IROX) can catalytically reduce $H_2O_2$. The morphology of the ceramic can enhance the catalytic effect and reduce growth of endothelial cells. Iridium oxide (IROX) is discussed further in Alt, U.S. Pat. No. 5,980,566. Defined grain morphologies may also allow for greater freedom of motion and are less likely to fracture as the stent is flexed in use and thus the coating resists delamination of the ceramic from an underlying surface and reduces delamination of an overlaying polymer coating. The stresses caused by flexure of the stent, during expansion or contraction of the stent or as the stent is delivered through a tortuously curved body lumen increase as a function of the distance from the stent axis. As a result, in embodiments, a morphology with defined grains is particularly desirable on abluminal regions of the stent or at other high stress points, such as the regions adjacent fenestrations which undergo greater flexure during expansion or contraction.

The morphology of the surface of the ceramic is characterized by its visual appearance, the size and arrangement of particular morphological features such as local maxima, and/or its roughness. In embodiments, the surface is characterized by definable sub-micron sized grains. Referring particularly to FIG. 4A, for example, in embodiments, the grains have a length, L, of the of about 50 to 500 nm, e.g. about 100-300 nm, and a width, W, of about 5 nm to 50 nm, e.g. about 10-15 nm. The grains have an aspect ratio (length to width) of about 5:1 or more, e.g. 10:1 to 20:1. The grains overlap in one or more layers. The separation between grains can be about 1-50 nm. In particular embodiments, the grains resemble rice grains.

Referring particularly to FIG. 4B, in embodiments, the surface is characterized by a more continuous surface having a series of shallow globular features. The globular features are closely adjacent with a narrow minima between features. In embodiments, the surface resembles an orange peel. The diameter of the globular features is about 100 nm or less, and the depth of the minima, or the height of the maxima of the globular function is e.g. about 50 nm or less, e.g. about 20 nm or less.

Figure 4C:
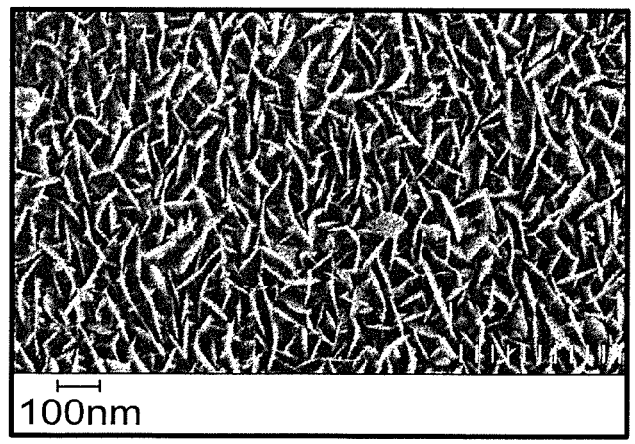

Referring to FIG. 4C, in other embodiments, the surface has characteristics between high aspect ratio definable grains and the more continuous globular surface and/or has a combination of these characteristics. For example, as shown in FIG. 4C, the morphology can include a substantially globular base layer and a relatively low density of defined grains. In other embodiments, the surface can include low aspect ratio, thin planar flakes. The morphology type is visible in FESEM images at 50 KX.

Figure 5A:
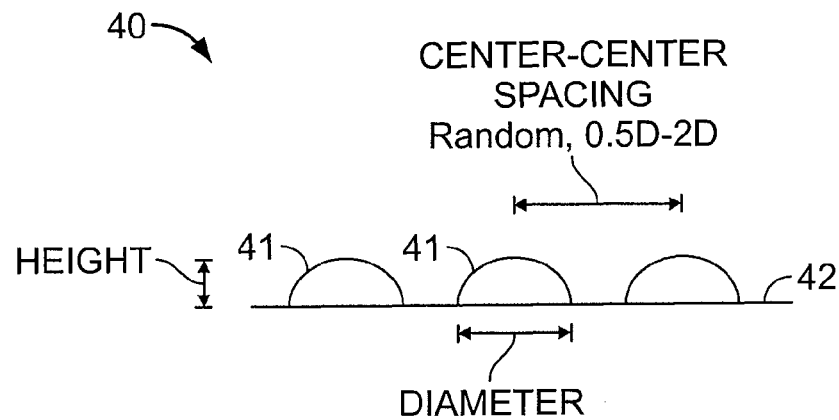
FIGS. 5A-5C are schematic views of ceramic morphologies.
Figure 5B:
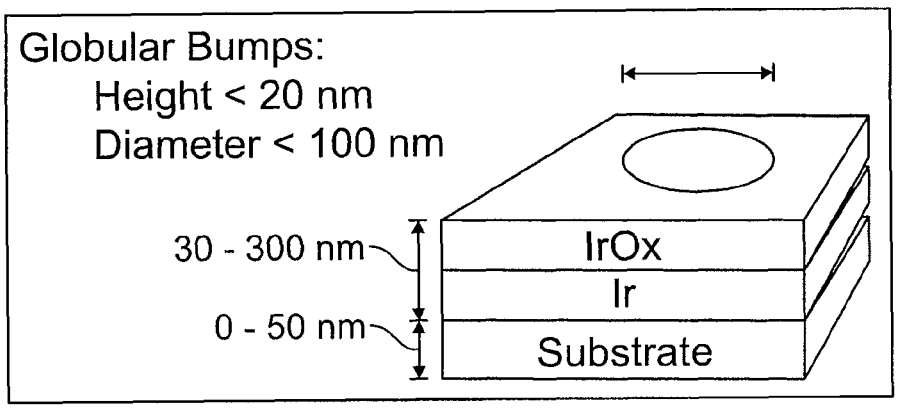
Figure 5C:
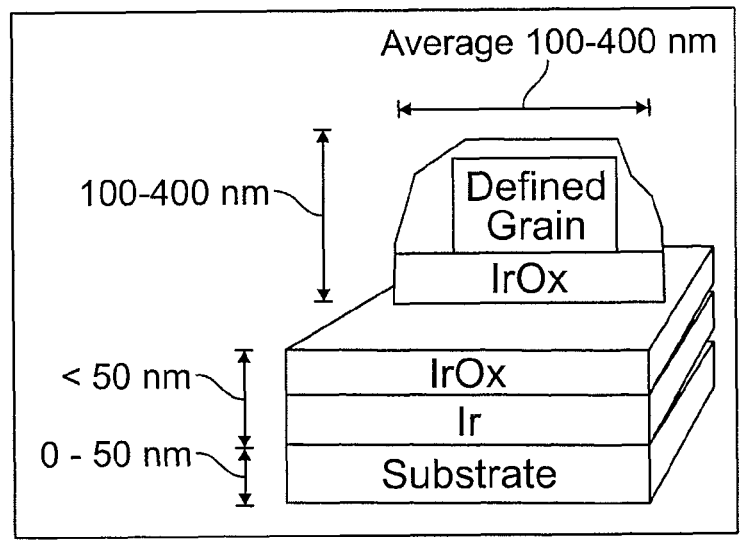

Referring to FIGS. 5A-5C, morphologies are also characterized by the size and arrangement of morphological features such as the spacing, height and width of local morphological maxima. Referring particularly to FIG. 5A, a coating 40 on a substrate 42 is characterized by the center-to-center distance and/or height, and/or diameter and/or density of local maxima. In particular embodiments, the average height, distance and diameter are in the range of about 400 nm or less, e.g. about 20-200 nm. In particular, the average center-to-center distance is about 0.5 to 2× the diameter.

Referring to FIG. 5B, in particular embodiments, the morphology type is a globular morphology, the width of local maxima is in the range of about 100 nm or less and the peak height is about 20 nm or less. In particular embodiments, the ceramic has a peak height of less than about 5 nm, e.g., about 1-5 nm, and/or a peak distance less than about 15 nm, e.g., about 10-15 nm. Referring to FIG. 5C, in embodiments, the morphology is defined as a grain type morphology. The width of local maxima is about 400 nm or less, e.g. about 100-400 nm, and the height of local maxima is about 400 nm or less, e.g. about 100-400 nm. As illustrated in FIGS. 5B and 5C, the select morphologies of the ceramic can be formed on a thin layer of substantially uniform, generally amorphous IROX, which is in turn formed on a layer of iridium metal, which is in turn deposited on a metal substrate, such as titanium or stainless steel. The spacing, height and width parameters can be calculated from AFM data. A suitable computational technique is provided below.

The roughness of the surface is characterized by the average roughness, Sa, the root mean square roughness, Sq, and/or the developed interfacial area ratio, Sdr. The Sa and Sq parameters represent an overall measure of the texture of the surface. Sa and Sq are relatively insensitive in differentiating peaks, valleys and the spacing of the various texture features. Surfaces with different visual morphologies can have similar Sa and Sq values. For a surface type, the Sa and Sq parameters indicate significant deviations in the texture characteristics. Sdr is expressed as the percentage of additional surface area contributed by the texture as compared to an ideal plane the size of the measurement region. Sdr further differentiates surfaces of similar amplitudes and average roughness. Typically Sdr will increase with the spatial intricacy of the texture whether or not Sa changes.

In embodiments, the ceramic has a defined grain type morphology. The Sdr is about 100 or more, e.g. about 120 to 200. In addition or in the alternative, the morphology has an Sq of about 20 or more, e.g. about 20 to 30. In particular embodiments, the ceramic has an Sdr of 150 or more, e.g., 180-300. In other embodiments, the ceramic has a globular type surface morphology. The Sdr is about 10 or less, e.g. about 1 to 8. The Sq is about 10 or less, e.g. about less than 3 or 1 to 5. In still other embodiments, the ceramic has a morphology between the defined grain and the globular surface, and Sdr and Sq values between the ranges above, e.g. an Sdr of about 1 to 200 and/or an Sq of about 1 to 30. The Sa, Sq, and Sdr can be calculated from AFM data. A suitable computation scheme is provided below.

The morphology of the ceramic coating can exhibit high uniformity. The uniformity provides predictable, tuned therapeutic and mechanical performance of the ceramic. The uniformity of the morphology as characterized by Sa, Sq or Sdr and/or average peak spacing parameters can be within about +/−20% or less, e.g. +/−10% or less within a 1 μm square. In a given stent region, the uniformity is within about +/−10%, e.g. about +/−1%. For example, in embodiments, the ceramic exhibits high uniformity over an entire surface region of stent, such as the entire abluminal or adluminal surface, or a portion of a surface region, such as the center 25% or 50% of the surface region. The uniformity is expressed as standard deviation. Uniformity in a region of a stent can be determined by determining the average in five randomly chosen 1 μm square regions and calculating the standard deviation. Uniformity of visual morphology type in a region is determined by inspection of FESEM data at 50 KX.

The ceramics are also characterized by surface composition, composition as a function of depth, and crystallinity. In particular, the amounts of oxygen or nitride in the ceramic is selected for a desired catalytic effect on, e.g., the reduction of $H_2O_2$ in biological processes. The composition of metal oxide or nitride ceramics can be determined as a ratio of the oxide or nitride to the base metal. In particular embodiments, the ratio is about 2 to 1 or greater, e.g. about 3 to 1 or greater, indicating high oxygen content of the surface. In other embodiments, the ratio is about 1 to 1 or less, e.g. about 1 to 2 or less, indicating a relatively low oxygen composition. In particular embodiments, low oxygen content globular morphologies are formed to enhance endothelialization. In other embodiments, high oxygen content defined grain morphologies are formed, e.g., to enhance adhesion and catalytic reduction. Composition can be determined by x-ray photoelectron spectroscopy (XPS). Depth studies are conducted by XPS after argon sputtering. The crystalline nature of the ceramic can be characterized by crystal shapes as viewed in FESEM images, or Miller indices as determined by x-ray diffraction. In embodiments, defined grain morphologies have a Miller index of <101>. Globular materials have blended amorphous and crystalline phases that vary with oxygen content. Higher oxygen content typically indicates greater crystallinity.

Figure 6:
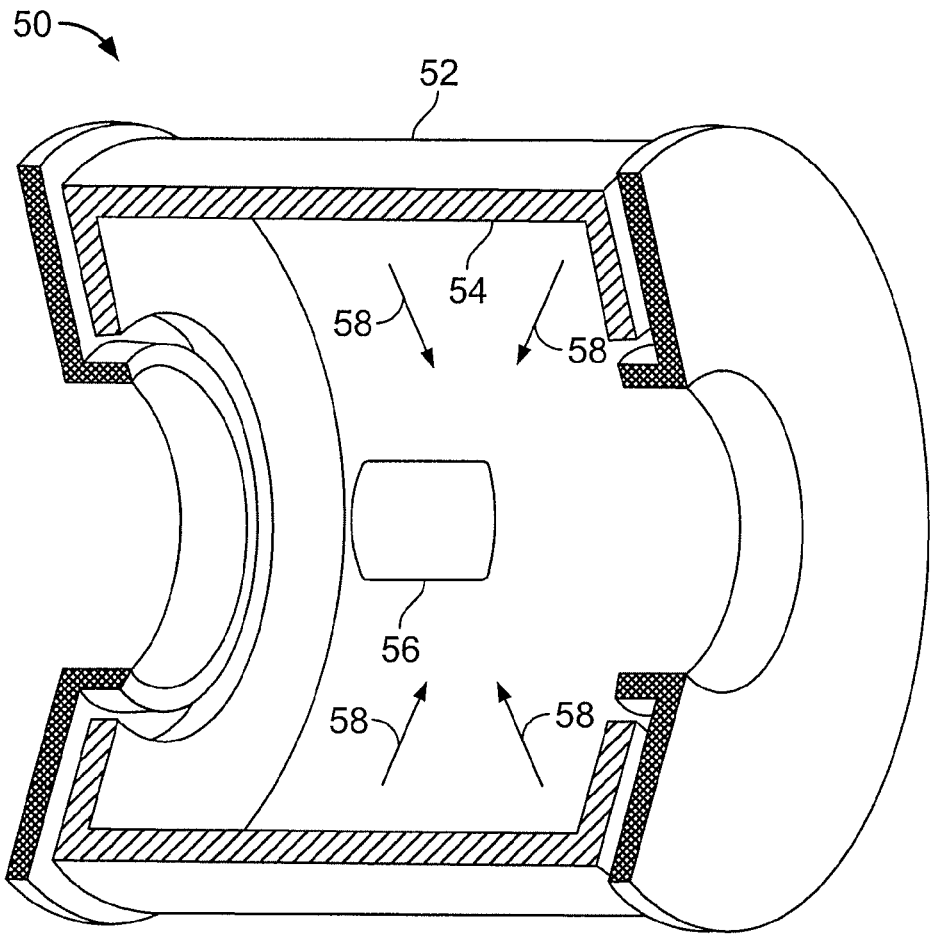
FIG. 6 is a schematic of an inverted cylindrical magnetron deposition system.

Referring to FIG. 6, the coatings can be formed using an inverted cylindrical physical vapor deposition arrangement 50 including a cathode 52 within which resides a target material 54, such as a ceramic (e.g. IROX) or a ceramic precursor metal (e.g. Ir). A stent 56 (or precursor component of a stent) is disposed within the cylinder. The cylinder also includes a gas, such as argon and oxygen. A plasma formed in the cylinder accelerates charged species toward the target. Target material is sputtered from the target and is deposited onto the stent (arrow 58).

The operating parameters of the deposition system are selected to tune the morphology and/or composition of the ceramic. In particular, the power, total pressure, oxygen/argon ratio and sputter time are controlled. By increasing the power and/or total pressure the morphology becomes more defined grain, rougher and crystalline. By decreasing these parameters the coating becomes more globular and less rough. In embodiments, the power is within about 340 to 700 watts, e.g. about 400 to 600 watts and the total pressure is about 10 to 30 mTorr. In other embodiments the power is about 100 to 350 watts, e.g. about 150 to 300 watts, and the total pressure is about 1 to 10 mTorr, e.g. about 2 to 6 mTorr. The oxygen partial pressure is in the range of about 10 to 90%. Particular ranges are about 80-90%, e.g. for defined grain morphologies, and 10 to 40%, e.g. for globular morphologies. The deposition time controls the thickness of the ceramic and the stacking of morphological features. In embodiments, the deposition time is about 0.5 to 10 minutes, e.g. about 1 to 3 minutes. The overall thickness of the ceramic is about 50-500 nm, e.g. about 100 to 300 nm. The oxygen content is increased at higher power, higher total pressure and high oxygen to oxygen ratios.

Inverted cylindrical physical vapor deposition is described further in Siegfried et al., Society of Vacuum Coaters, $39^{th}$ Annual Technical Conference Proceedings (1996), p. 97; Glocker et al., Society of Vacuum Coaters, $43^{rd}$ Annual Technical Conference Proceedings-Denver, Apr. 15-20, 2000, p. 81; and SVC: Society of Vacuum Coatings: C-103, An Introduction to Physical Vapor Deposition (PVD) Processes and C-248-Sputter Deposition in Manufacturing, available from SVC 71 Pinion Hill, NE, Albequeque, N. Mex. 87122-6726. A suitable cathode system is the Model 514, available from Isoflux, Inc., Rochester, N.Y. Other sputtering techniques include closed loop cathode magnetron sputtering. Pulsed laser deposition is described in co-pending application U.S. Ser. No. 11/752,735, filed concurrently [Attorney Docket 10527-801001]. Formation of IROX is also described in Cho et al., *Jpn. J. Appl. Phys.* 36(1)3B: 1722-1727 (1997), and Wessling et al., *J. Micromech. Microeng.* 16:5142-5148 (2006).

EXAMPLE

A series of IROX layers are formed as described in the following Table.

TABLE

| Material | Deposition System | Parameters | Type | Sq nm | $S_{dr}$ % | Uniformity (FESEM) | Peak Height (nm) | Peak Distance (nm) |
|---|---|---|---|---|---|---|---|---|
| A | magnetron sputtering | — | mixed | 33 | 25 | lower | ~44 | ~20 |
| B | magnetron sputtering | — | mixed | 12 | — | lower | | |
| C | magnetron sputtering | — | mixed | 7 | 3 | lower | ~10 | ~22 |
| D | wet chemical | — | mixed | 70 | 44 | lower | | |
| E | cylindrical vertical magnetron sputtering | — | globular | 1 | 1 | high | 4-5 | 17-22 |
| F | closed field balanced magnetron sputtering | — | defined grain | 27 | 142 | high | — | — |
| G | inverted cylindrical magnetron sputtering | P = 400-600 W<br>Pres = 18-24 mTorr<br>$O_2/A$ = 80-90%<br>T = 1-3 min | defined grain | 30 | 180 | high | — | — |
| H | inverted cylindrical magnetron sputtering | P = 150-300 W<br>Pres = 2-6 mTorr<br>$O_2/A$ = 10-40%<br>T = 1-3 min | globular | 6 | 7 | high | 1-5+/-1-5 | 10-15 |

Figure 7:
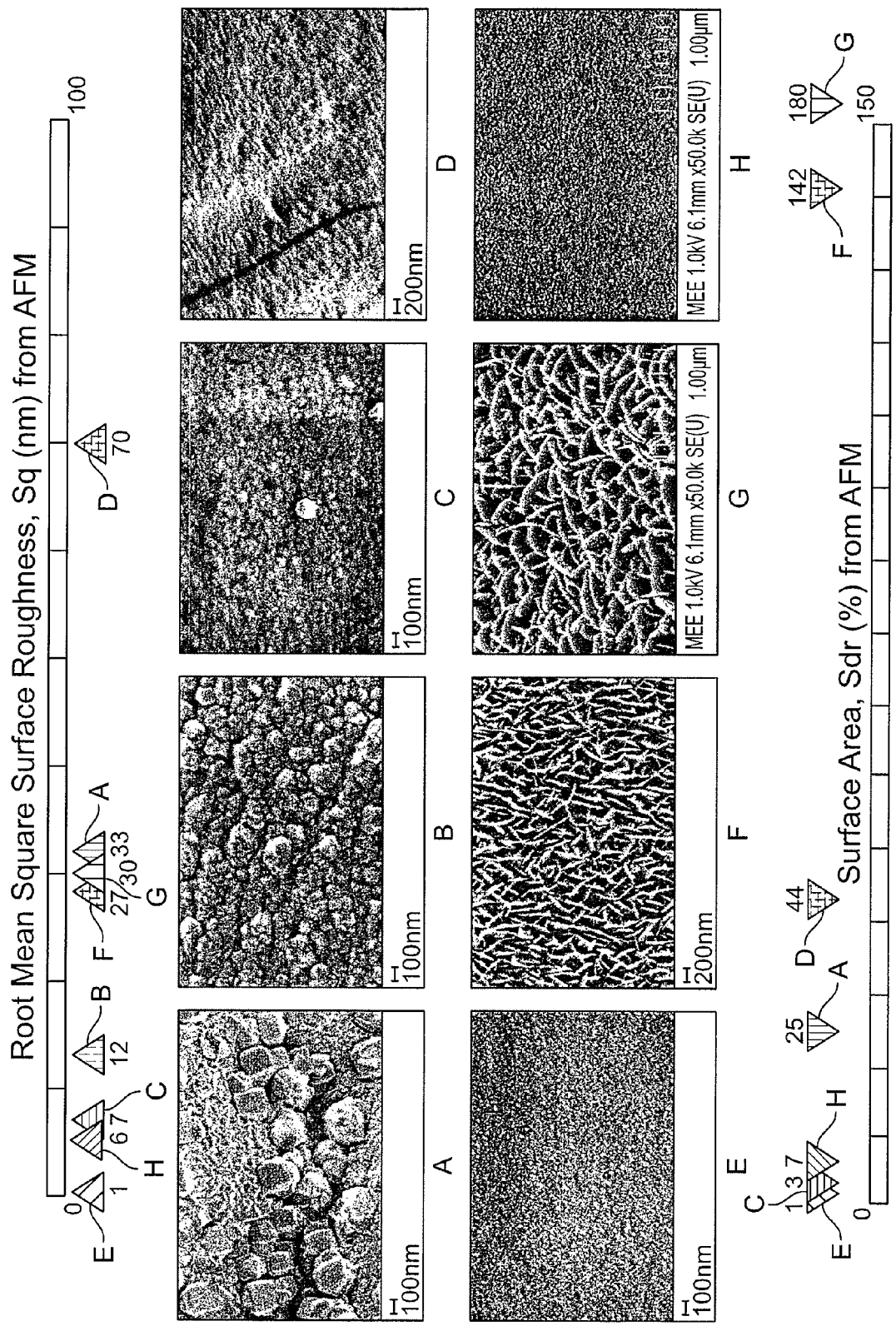
FIGS. 7A-7H are plan views of morphologies.

Referring to FIG. 7, FESEM images at 50 KX are provided for the ceramic materials A-H, along with morphology type, Sq and Sdr values, visual uniformity, and peak height and distance data. Materials A-C are formed by magnetron sputtering processes. The ceramics have surfaces that exhibit an intermediate morphology characterized by lobes or rock-like features integrated with or on top of smoother but still granulated surfaces. The uniformity is relatively low, with regions of lower and higher roughness and the presence of non-uniform features such as isolated regions of rock-like features. Material D is on a commercial pacemaker electrode formed by wet chemical techniques. The material exhibits a smoother but still granulated surface.

Material E is a globular material formed by cylindrical vertical magnetron sputtering. The material exhibits a relatively smooth surface, an Sq of about 1, and an Sdr of about 1. The peak height is about 4-5 nm and the peak distance is about 17-22 nm. Material F is a defined grain material formed by closed field balanced magnetron sputtering. This material exhibits a complex, relatively rough textured surface of intersecting grains. This material has an Sq of about 27 and an Sdr of about 142. These materials exhibit high morphology uniformity.

Materials G and H are defined grain and globular materials, respectively, both of which are formed by inverted cylindrical magnetron sputtering but under varying operating conditions. The defined grain material (Material G) is formed as relatively high power of 400-600 W, high pressure of 18-24 mTorr, and high oxygen to Argon ratio of 80-90. The globular material (Material H) is formed at lower power of 150-300 W, lower pressure of 2-6 mTorr and lower oxygen to Argon ratio of about 10-40. Material G has an Sq of about 30 and a high Sdr of about 180. Material H has an Sq of about 6 and an Sdr of about 7. Material G also has a low peak height of about 1 to 5 and a peak distance of about 10-15.

Figure 8:
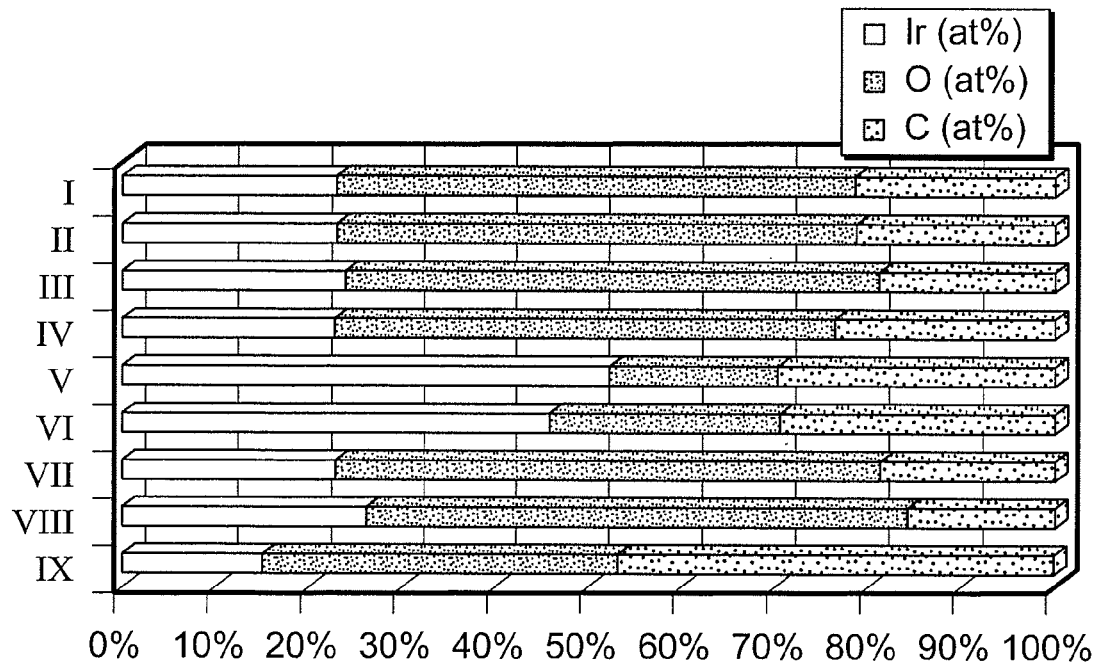
FIG. 8 is a graph of surface compositions.

Referring to FIG. 8, the surface chemistry of various materials are illustrated. Materials I-VI are formed by inverted cylindrical magnetron sputtering. Materials I-III are defined grain morphologies. Materials IV-VI are globular morphologies. Materials I-IV exhibit a greater oxygen content than Materials V and VI. Oxygen content can be increased by inverted cylindrical magnetron sputtering operating at generally higher power, high pressure and/or higher oxygen partial pressure.

Material VII, which corresponds to Material F in FIG. 8, is a relatively high oxygen content defined grain morphology formed by magnetron sputtering. Material VII, which corresponds to Material E in FIG. 8, is a relatively low oxygen content globular material. Material IX, which corresponds to the material in C in FIG. 8, is an intermediate material with intermediate surface oxygen.

Figure 9A:
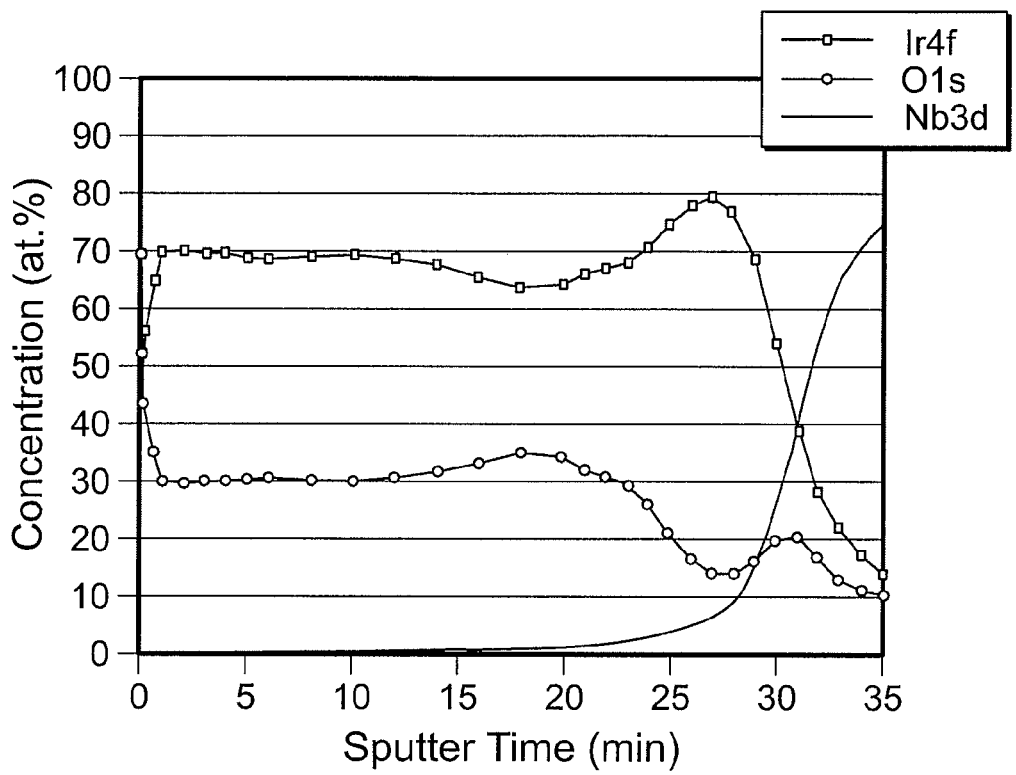
FIGS. 9A-9C are graphs of composition as a function of depth.
Figure 9B:
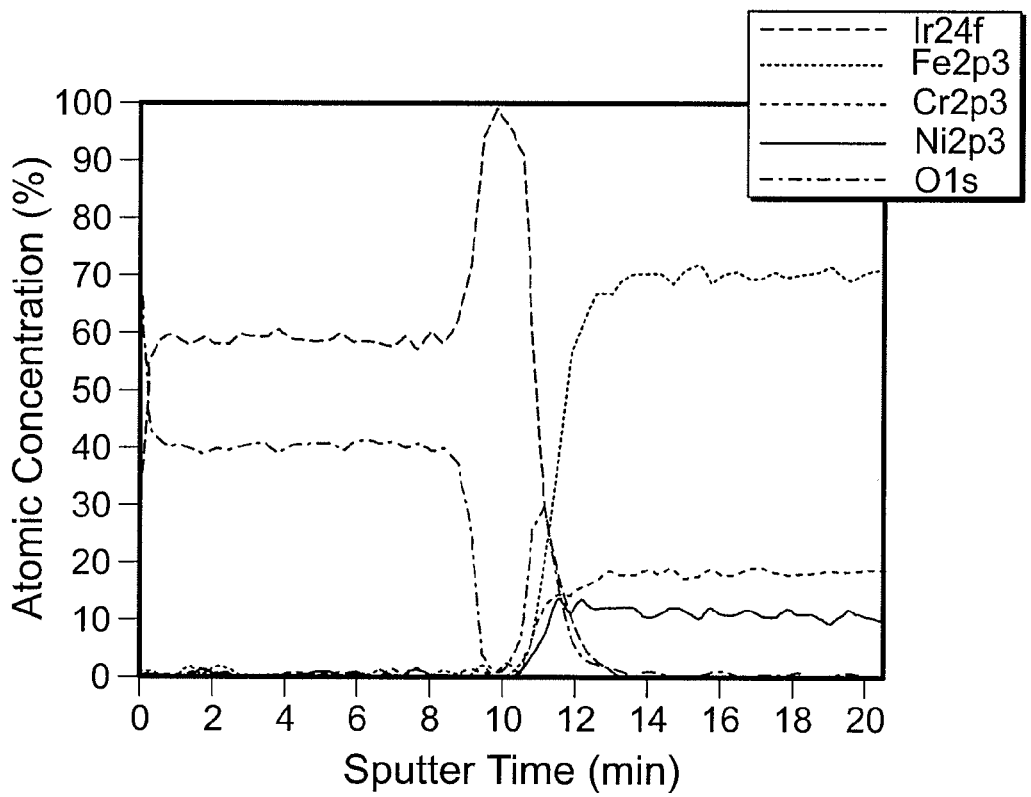
Figure 9C:
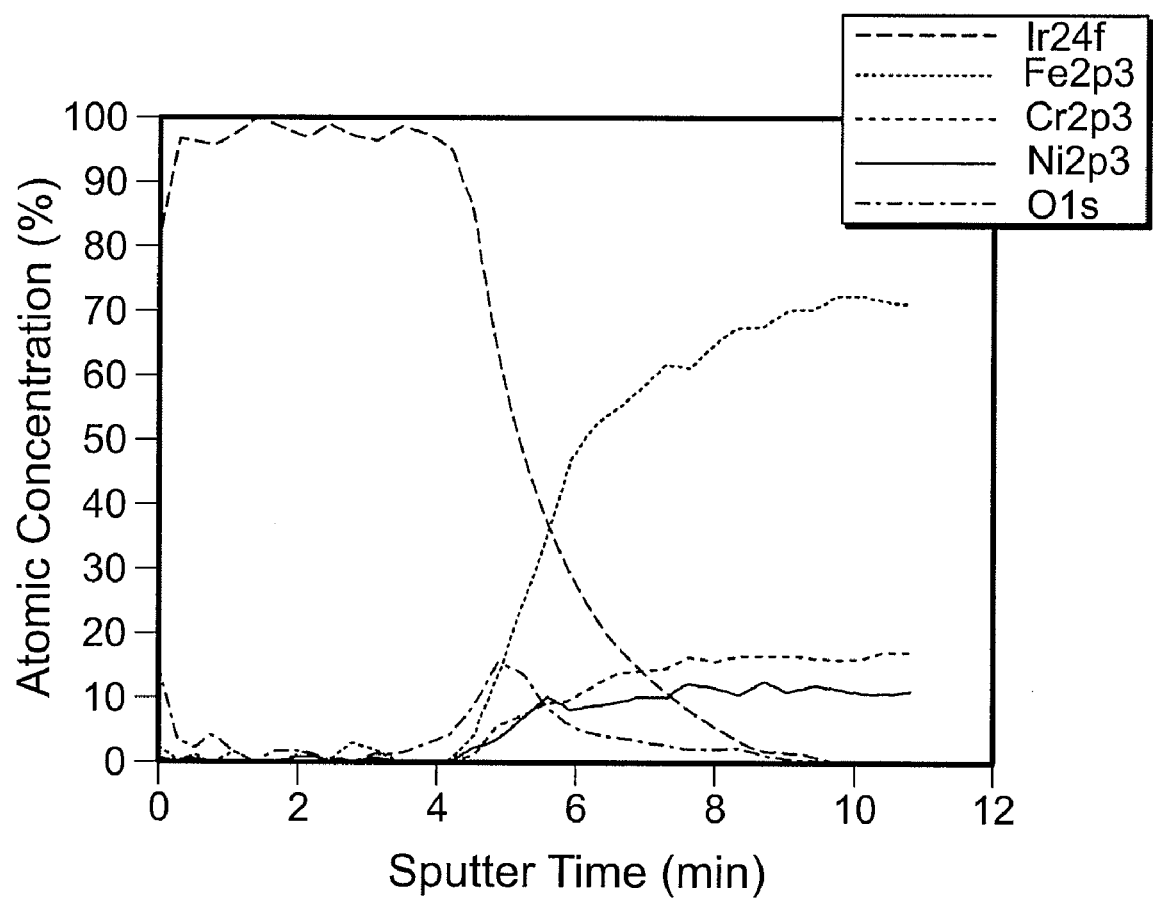
Figure 10A:
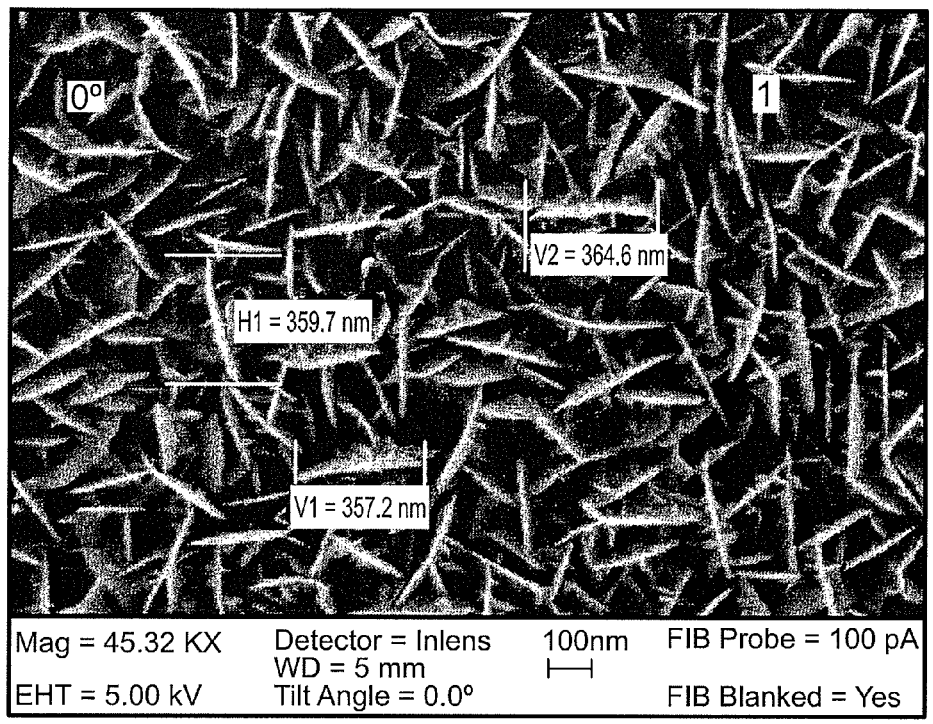
FIG. 10A is a plan view.
Figure 10B:
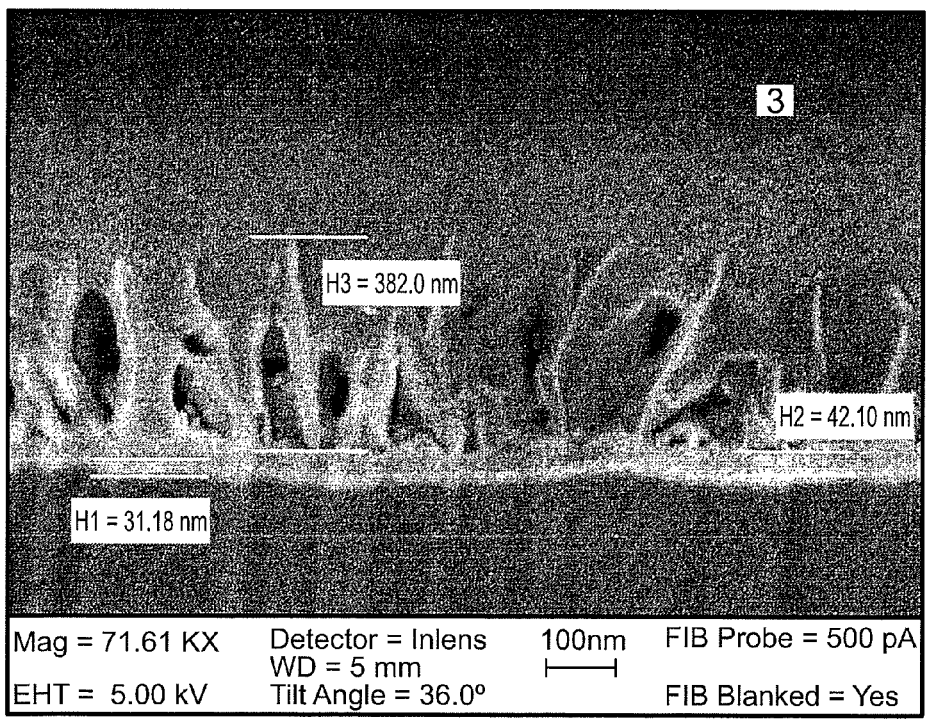
FIGS. 10B and 10C are cross-sectional views and FIG. 10D is a perspective view of a morphology.
Figure 10C:
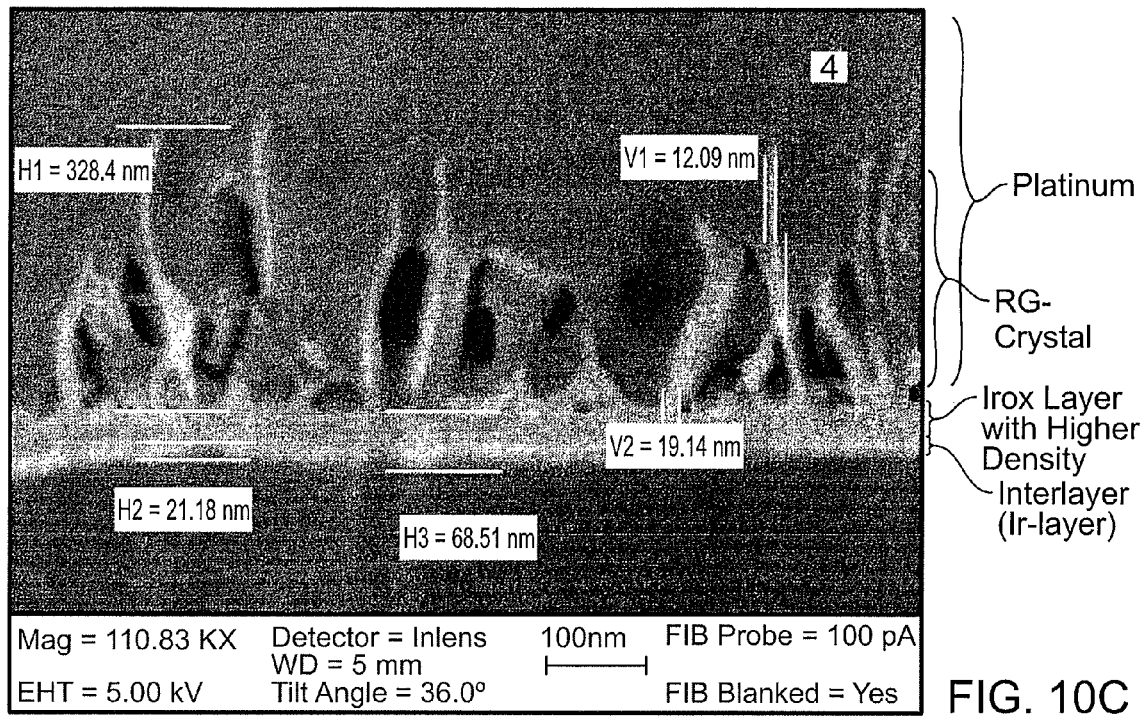
Figure 10D:
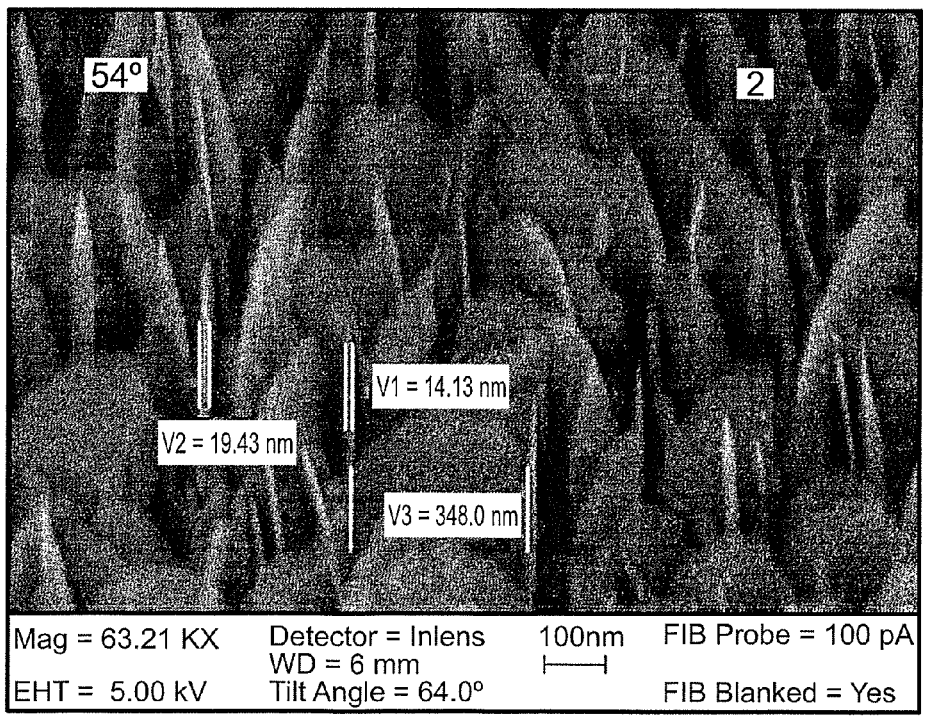

Referring to FIGS. 9A-9C, the chemistry as a function of ceramic depth is illustrated. Referring to FIG. 9A, the oxygen and iridium depth provide for intermediate material XI in FIG. 8 is substantially constant. Referring particularly to FIGS. 9B and 9C, depth profiles are illustrated for globular materials IV and VI, respectively. Surface chemistry and depth profiles can be determined by x-ray photoelectron spectroscopy.

Referring to FIG. 10, ceramic material can also be characterized by its chrystalline structure. Referring particularly to FIG. 10A, a plan FESM view of a defined grain material is provided. Referring particularly to FIGS. 10B and 10C, cross-sectional FESM views at different magnification of the same material are provided. The cross-section illustrates a structure of crystals extending from a higher density IROX layer, which in turn extends from an interlayer of Iridium. Referring to FIG. 10D, a perspective view illustrates the shape of the crystals as a function of depth.

In embodiments, ceramic is adhered only on the abluminal surface of the stent. This construction may be accomplished by, e.g. coating the stent before forming the fenestrations. In other embodiments, ceramic is adhered only on abluminal and cutface surfaces of the stent. This construction may be accomplished by, e.g., coating a stent containing a mandrel, which shields the luminal surfaces. Masks can be used to shield portions of the stent. In embodiments, the stent metal can be stainless steel, chrome, nickel, cobalt, tantalum, superelastic alloys such as nitiniol, cobalt chromium, MP35N, and other metals. Suitable stent materials and stent designs are described in Heath '721, supra. In embodiments, the morphology and composition of the ceramic are selected to enhance adhesion to a particular metal. For example, in embodiments, the ceramic is deposited directly onto the metal surface of a stent body, e.g. a stainless steel, without the use of an intermediate metal layer. In other embodiments, a layer of metal common to the ceramic is deposited onto the stent body before deposition to the ceramic. For example, a layer of iridium may be deposited onto the stent body, followed by deposition of IROX onto the iridium layer. Other suitable ceramics include metal oxides and nitrides, such as of iridium, zirconium, titanium, hafnium, niobium, tantalum, ruthenium, platinum and aluminum. The ceramic can be crystalline, partly crystalline or amorphous. The ceramic can be formed entirely of inorganic materials or a blend of inorganic and organic material (e.g. a polymer). In other embodiments, the morphologies described herein can be formed of metal. In embodiments, the thickness T of the coatings is in the range of about 50 nm to about 2 um, e.g. 100 nm to 500 nm.

Figure 11A:
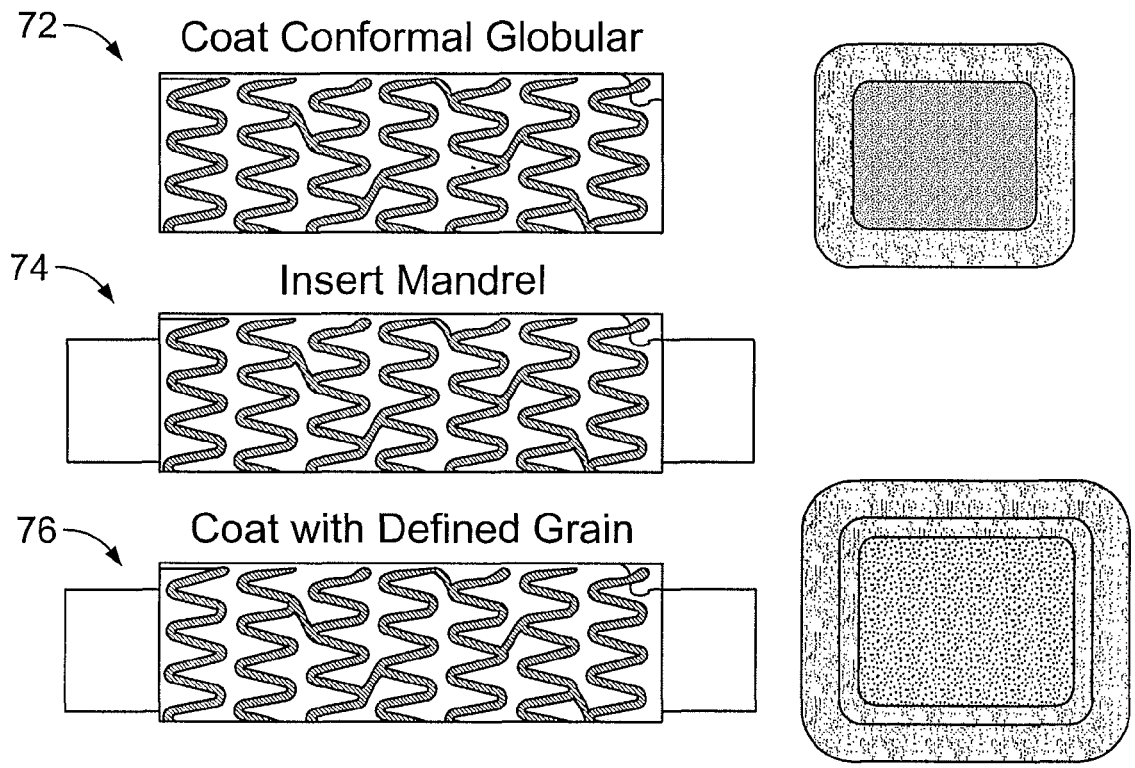
FIGS. 11A-11E are schematics of methods of providing variable morphologies on stents.

Referring to FIGS. 11A-11E, processes for providing different morphologies on different surfaces are illustrated. Referring to FIG. 11A, in an embodiment, in a first step 72, a stent is coated on all surfaces with a globular morphology. In a second step 74, a mandrel is inserted into the stent to mask the abluminal surface. In a third step 76, a defined grain morphology is coated on the abluminal and cutface surfaces over the previously deposited globular morphology.

Figure 11B:
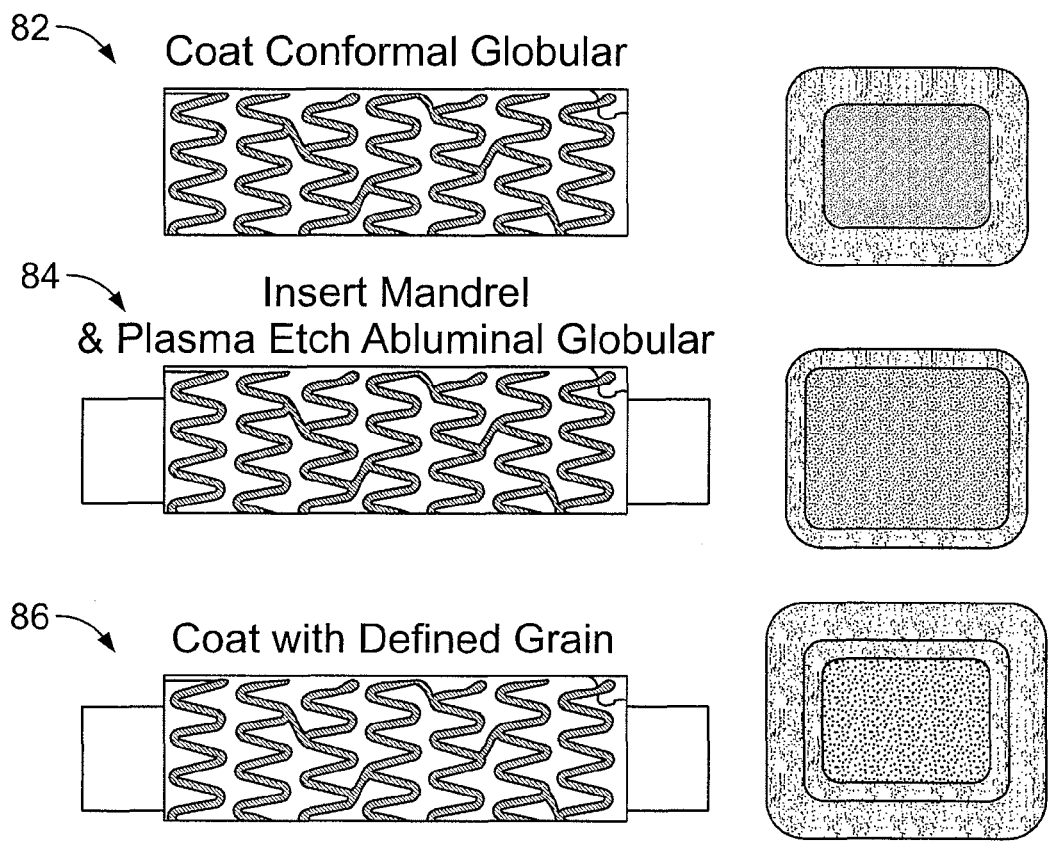

Referring to FIG. 11B, in an embodiment, in a first step 82, a stent is coated on all surfaces with a globular morphology. In a second step 84, a mandrel is inserted into the stent and the stent is subject to plasma etching to remove the covering from the abluminal surface. In a third step 86, a defined grain morphology is deposited on the abluminal surface and over the globular morphology or cutface surfaces.

Figure 11C:
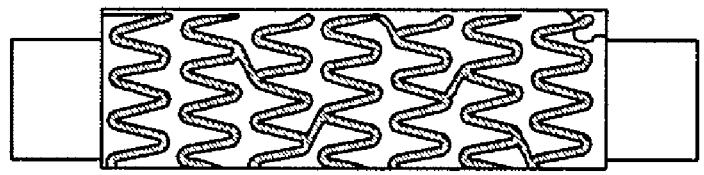
Figure 11C:
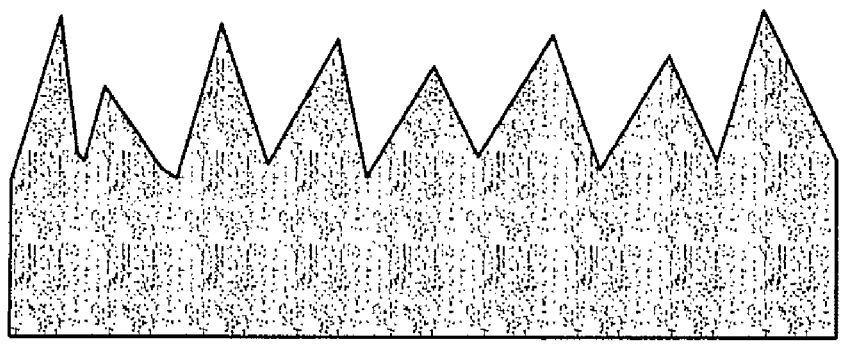
Figure 11C:
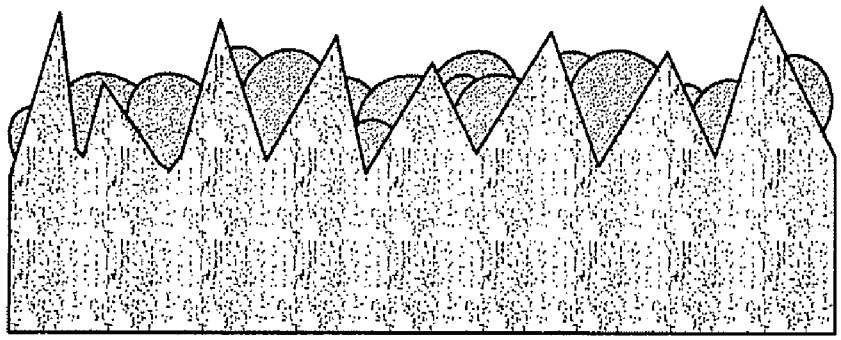

Referring to FIG. 11C, in an embodiment, in a first step 83, a mandrel is inserted in a stent. In a second step 85, a defined grain morphology is deposited onto the adluminal surface of the stent. In a third step 87, the mandrel is removed and a globular morphology is deposited on all surfaces of the stent. The thickness of the globular morphology is less than the depth of the grains of the defined grain morphology so that on the abluminal surfaces, the morphology retains a defined grain character.

Figure 11D:
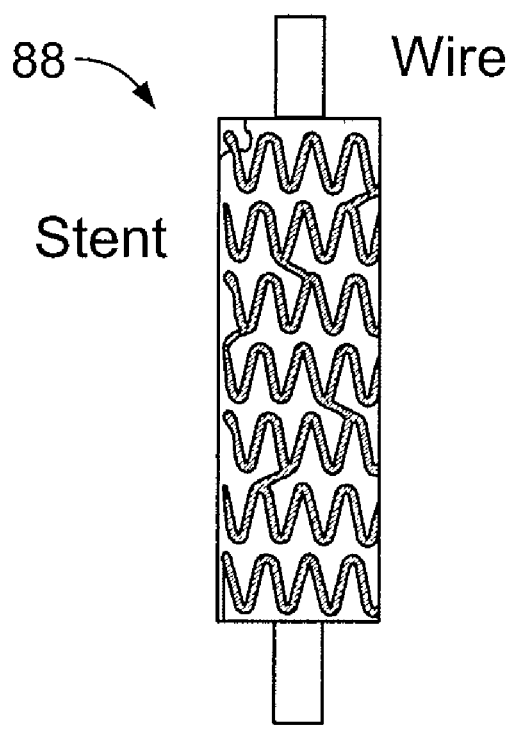
Figure 11D:
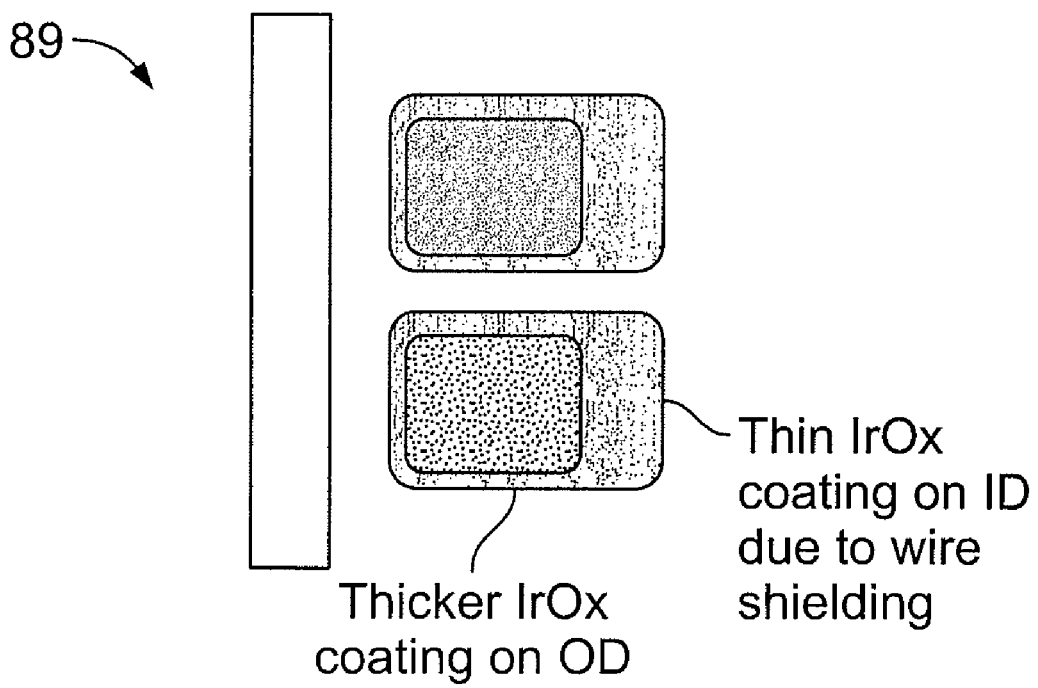

Referring to FIG. 11D, in an embodiment, in a first step 88, a wire is provided inside a stent to partially shield the stent during deposition in a second step 89. The wire also inhibits deformed grain formulations and the conditions are varied during the deposition to provide a thin coating of a globular morphology on the adluminal surface and a thicker defined grain morphology on the abluminal surface.

Figure 11E:
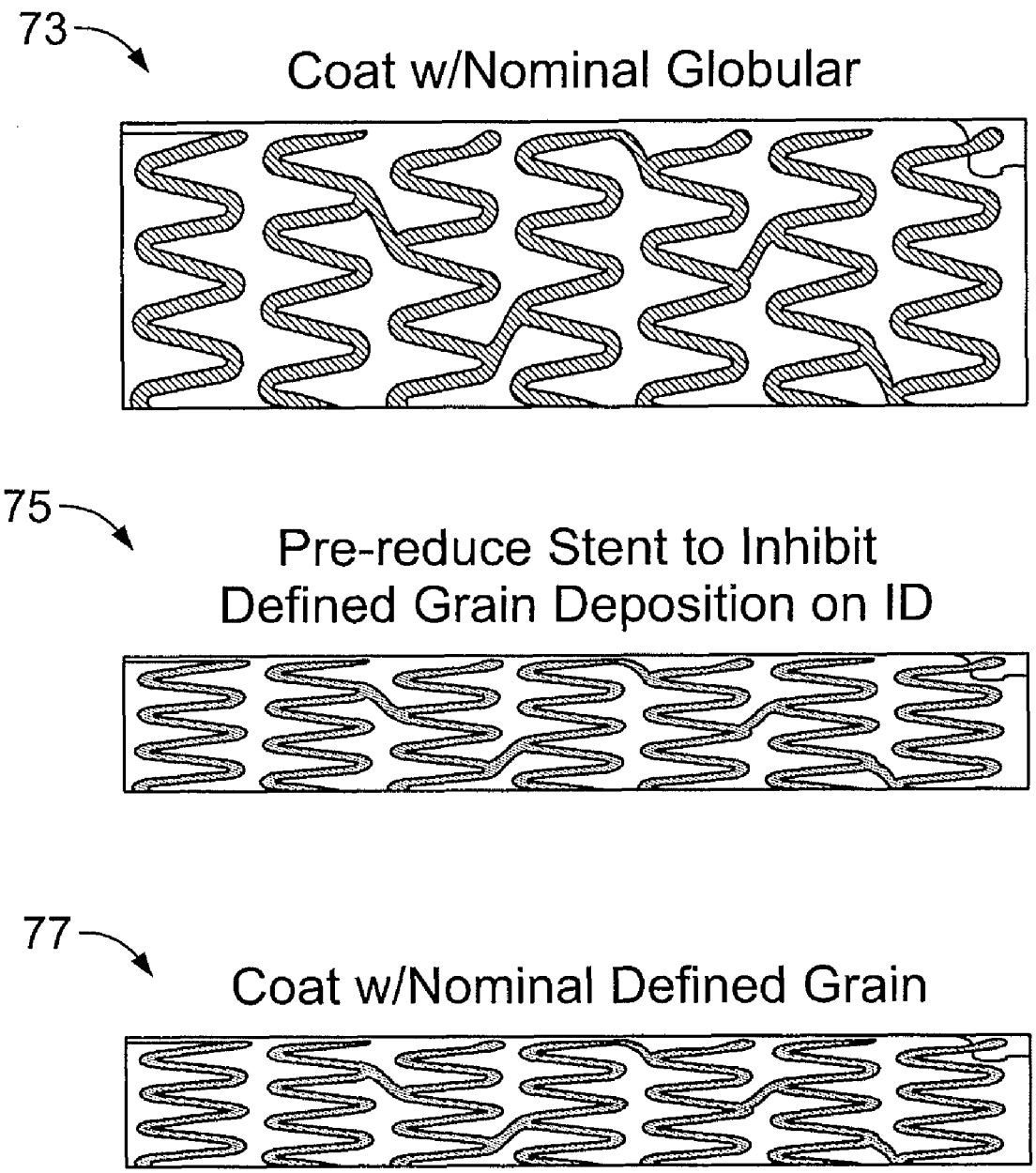

Referring to FIG. 11E, in an embodiment, in a first step 73, a stent is inserted into a surface with a globular morphology. In a second step 75, the stent is compressed to a smaller diameter. In a third step 77, a defined grain coating is deposited. The compression of the stent to a smaller diameter inhibits growth of defined grain morphology on the adluminal surfaces. The resulting stent includes a defined grain morphology on abluminal surfaces and a globular morphology on adluminal surfaces.

Figure 12:
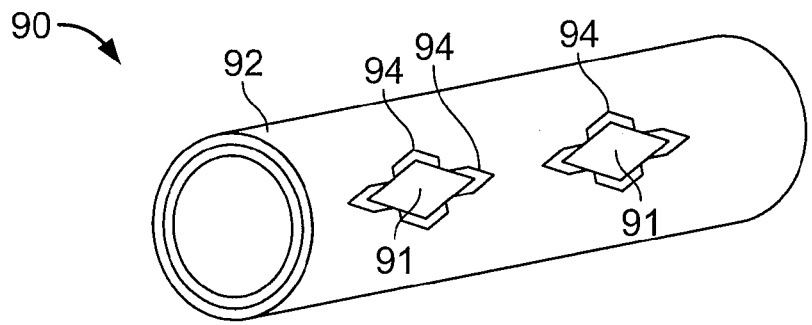
FIGS. 12-15 are perspective views of stents.

Referring to FIGS. 12-15, other deposition patterns are illustrated. Referring to FIG. 12, a stent 90 including fenestrations 91 has first and second ceramic materials 92, 94. The ceramic material 92 covers substantially a surface of a stent except high stress regions such as adjacent to the species of the fenestrations, where material 94 is provided. Material 94 is, for example, a defined grain material that resists cracking or delamination in high stress locations and material 92 is a globular material.

Figure 13:
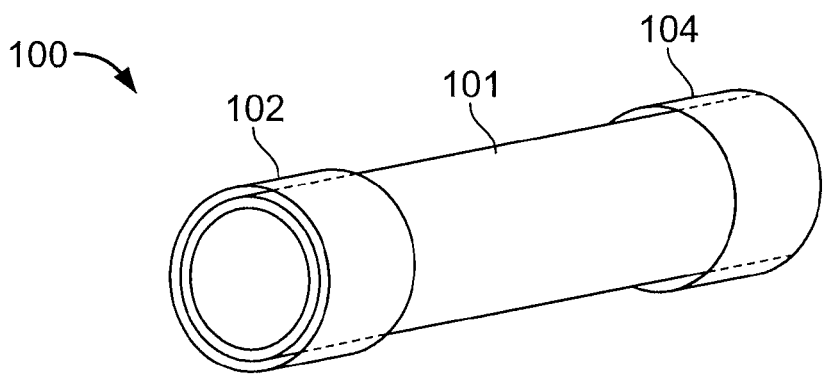
Figure 14:
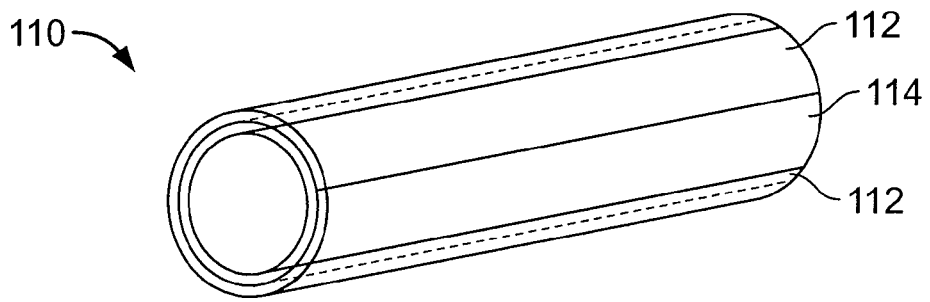
Figure 15:
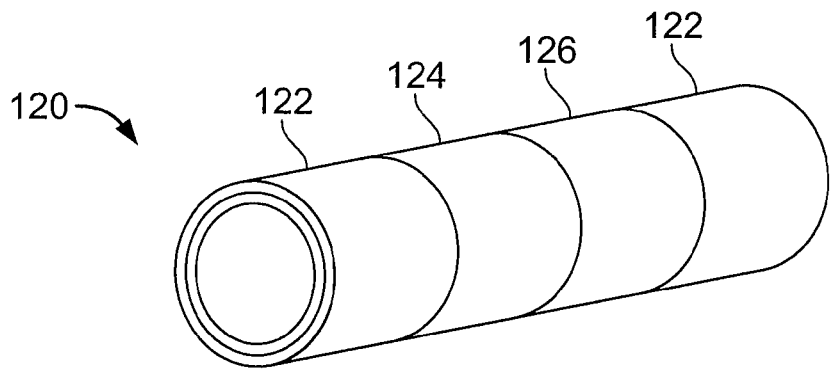

Referring particularly to FIG. 13, a stent 100 includes a body 101 ceramic material 102, 104 over its end regions which correspond to the location of untreated tissue. Ceramic materials 102, 104 may be, e.g. of the same or different morphology and/or chemistry. For example, the ceramics 102, 104 can be selected to enhance endothelialization. Referring to FIG. 14, a stent 110 has a series of different ceramic materials 112, 114 arranged along its length. Referring to FIG. 15, a stent 120 has different ceramic materials 122, 124, 126 arranged radially about the stent axis. In embodiments, a polymer is provided only on the abluminal surface, as illustrated. In other embodiments, polymer layers are provided as well or only on the luminal surface and/or cut-face surfaces.

The ceramic material can also be selected for compatibility with a particular polymer coating to, e.g. enhance adhesion. For example, for a hydrophobic polymer, the surface chemistry of the ceramic is made more hydrophobic by e.g., increasing the oxygen content, which increases polar oxygen moieties, such as OH groups. Suitable drug eluting polymers may be hydrophilic or hydrophobic. Suitable polymers include, for example, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics such as polystyrene and copolymers thereof with other vinyl monomers such as isobutylene, isoprene and butadiene, for example, styrene-isobutylene-styrene (SIBS), styrene-isoprene-styrene (SIS) copolymers, styrene-butadiene-styrene (SBS) copolymers, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, natural and synthetic rubbers including polyisoprene, polybutadiene, polyisobutylene and copolymers thereof with other vinyl monomers such as styrene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyiocyanates such that the devices become instantly lubricious when exposed to body fluids. In another preferred embodiment of the invention, the polymer is a copolymer of polylactic acid and polycaprolactone. Suitable polymers are discussed in U.S. Publication No. 2006/0038027.

In embodiments, the polymer is capable of absorbing a substantial amount of drug solution. When applied as a coating on a medical device in accordance with the present invention, the dry polymer is typically on the order of from about 1 to about 50 microns thick. Very thin polymer coatings, e.g., of about 0.2-0.3 microns and much thicker coatings, e.g., more than 10 microns, are also possible. Multiple layers of polymer coating can be provided. Such multiple layers are of the same or different polymer materials.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

Exemplary therapeutic agents include, e.g., anti-thrombogenic agents (e.g., heparin); anti-proliferative/anti-mitotic agents (e.g., paclitaxel, 5-fluorouracil, cisplatin, vinblastine, vincristine, inhibitors of smooth muscle cell proliferation (e.g., monoclonal antibodies), and thymidine kinase inhibitors); antioxidants; anti-inflammatory agents (e.g., dexamethasone, prednisolone, corticosterone); anesthetic agents (e.g., lidocaine, bupivacaine and ropivacaine); anti-coagulants; antibiotics (e.g., erythromycin, triclosan, cephalosporins, and aminoglycosides); agents that stimulate endothelial cell growth and/or attachment. Therapeutic agents can be nonionic, or they can be anionic and/or cationic in nature. Therapeutic agents can be used singularly, or in combination. Preferred therapeutic agents include inhibitors of restenosis (e.g., paclitaxel), anti-proliferative agents (e.g., cisplatin), and antibiotics (e.g., erythromycin). Additional examples of therapeutic agents are described in U.S. Published Patent Application No. 2005/0216074. Polymers for drug elution coatings are also disclosed in U.S. Published Patent Application No. 2005/019265A. A functional molecule, e.g. an organic, drug, polymer, protein, DNA, and similar material can be incorporated into groves, pits, void spaces, and other features of the ceramic.

The stents described herein can be configured for vascular, e.g. coronary and peripheral vasculature or non-vascular lumens. For example, they can be configured for use in the esophagus or the prostate. Other lumens include biliary lumens, hepatic lumens, pancreatic lumens, uretheral lumens and ureteral lumens.

Any stent described herein can be dyed or rendered radiopaque by addition of, e.g., radiopaque materials such as barium sulfate, platinum or gold, or by coating with a radiopaque material. The stent can include (e.g., be manufactured from) metallic materials, such as stainless steel (e.g., 316L, BioDur® 108 (UNS S29108), and 304L stainless steel, and an alloy including stainless steel and 5-60% by weight of one or more radiopaque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., U.S. Pat. No. 6,290,721). The ceramics can be used with other endoprostheses or medical devices, such as catheters, guide wires, and filters.

Computation

Figure 16:
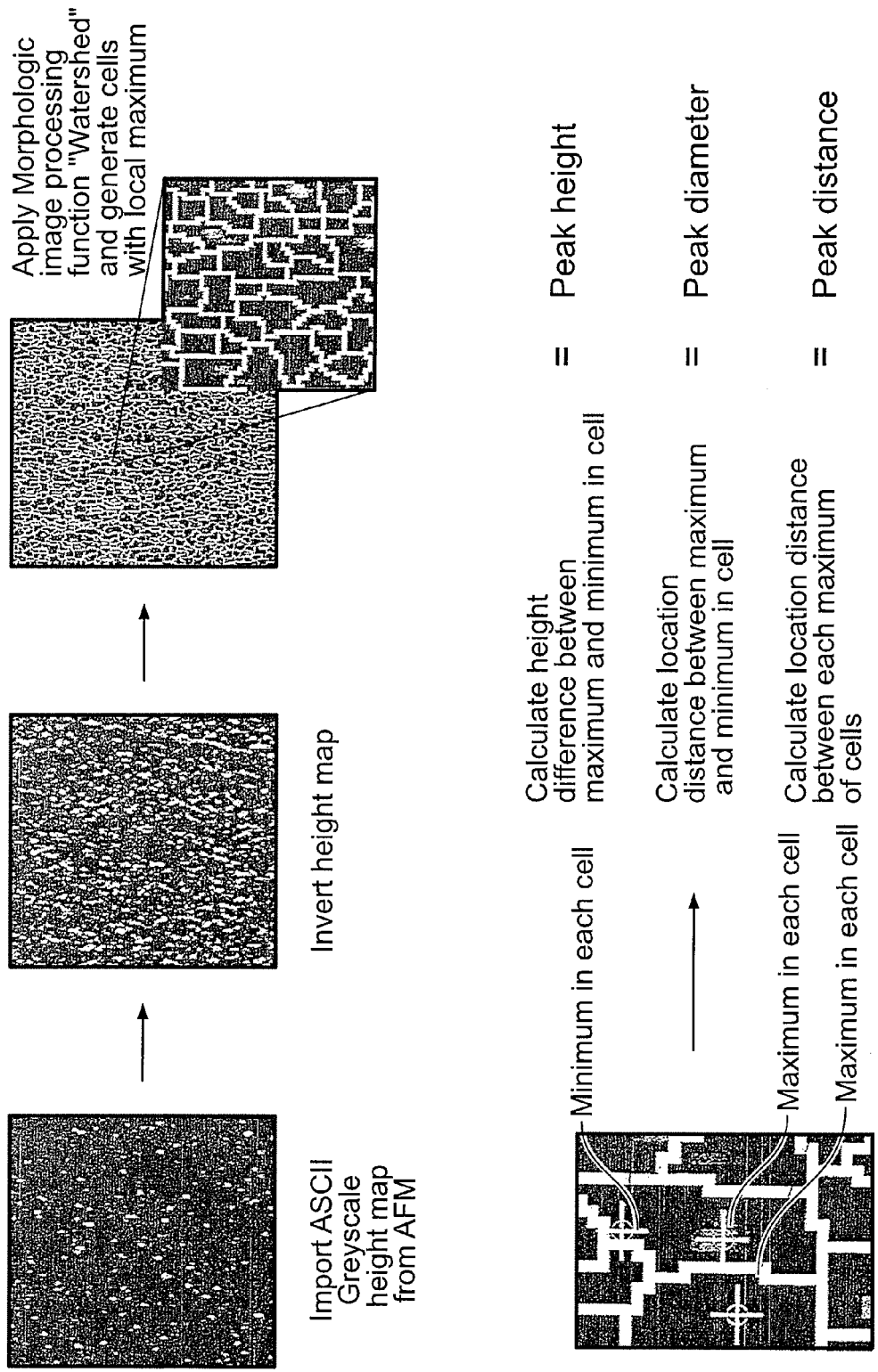
FIG. 16 is a schematic for computing morphology feature parameters.

The roughness and feature parameters are calculated from AFM data. A height map is imported from the AFM as a matrix of height values. An image of a 1 um square region is represented by a 512×512 pixel matrix for a resolution of about 2-3 nm. For morphologies that exhibit substantial defined grains, the roughness parameters, Sa, Sq, and Sdr, as well as feature parameters such as peak height, peak diameter and peak distance can be calculated directly from the pixel matrix. For globular type morphologies, in which the differential between minima and maxima are less pronounced, a watershed function can be used, which is illustrated in FIG. 16. The grey scale height map is inverted and a watershed function is used to generate local maxima and minima. The roughness parameter and the feature parameter are calculated from the watershed processed data. The watershed process is used to more efficiently find local maxima and minima in the generally smoother globular morphologies. Suitable software for calculating height map is the Scanning Probe Image Processor (SPIP) from Imagnet in Lyngby, Denmark. Software for determining feature parameters is developed using IDL Software from RSI, Inc., ITT Visual Information Solutions, Boulder, Colo. Code for computing the image feature parameters is provided below.

```
;
; Routine for IDL Version 6.2 WIN 32 (xes)
; Analyzes local peaks on height maps
;
; xxxxxxxxxxxxxxxxx
; INPUT variables:
; height_map; Matrix containing height in nm per matrix element (pixel)
; pixsize: Vector containing size of one pixel in x and y direction in nm
; xxxxxxxxxxxxxxxxx
;
; IDL is a product of ITT Visual Information Solutions www.ittvie.com
; Corporate Headquarters
; 4990 Pearl East Circle
; Boulder, CD 80301
PRO analyze_peaks, height_map, pixsize
; Calculates amount of pixels in x and y direction
pix = {x:0,y:0}
pix.x = (size(height_map))[1]
pix.y = (size(height_map))[2]
; image size x-axis in nanometers
imagesizex = pixsize.x*pix.x/1000.0
; image size y-axis in nanometers
imagesizey = pixsize.y*pix.y/1000.0
res = height_map
;shift image in positive values
a = res − min(res)
;Invert the image
b = MAX(e) − a
c = b
/Create watershed image = identifies local maximum
d = WATERSHED(c,connectivity=9)
; initialize matrices
fa = make_array(pix.x,pix.y,/float)
fa_leveled = make_array(pix.x,pix.y,/float)
level_max = make_array(max(d)+1./float)
level_min = level_max
level_dif = level_max
level_grad = level_max
level_loc = level_max
max_ix = level_max
max_iy = level_max
struct = make_array(2,2,/byte, value−1)
; repeat calculations for each local maxima i
for i=1 max(d) do begin
; erases boundaries from identified local maximum cell
    fa = a * dilate((d sq i),struct)
    fa_min = a·max(a)) * dilate((d eq i).struct)
    tmpa = max(fa, location_max)
```

```
; calculate height of local maxima for each local maxima i
level_max[f] = tmpa
; calculate height of next minima for each local maxima i
level_min[i] = min(fc_min, location_min) +max(a)
; calculate difference between local maxima and next minima for each maxima i
; = local peak height
level_dis[f] = tmpa - level_min[i]
fa_leveled = fa_leveled + fc - tmpa* (fc ne 0)
; Find pixels where maxima and minima on image located
IX_max = location_max MOD pix.x
IY_max = location_max/pix.y
IX_min = location_min MOD pix.x
IY_min = location_min/pix.y
fa[ix_max,iy_max] = 1.0
fa[ix_min,iy_min] = -1.0
; calculate lateral distance between local maxima and next minima for each local maxima i
; = local peak radius
level_loc[i] = sqrt(((IX_max-IX_min)*pixsize.x)^2+((IY_max-IY_min)*pixszie.y)^2)
; calculate local maxima position
max_ix[i] = IX_max*pixsize.x
max_iy[j] = IY_max*pixsize.y
; calculate gradient between local maxima and next minima for each local maxima i
level_grad[i] = (level_max[i]-level_min[i])/level_loc[i]
endfor
;calculate nearest distance of next local maximum
k = 0
k = long(k)
maxd = long(max(d))
max_dist1 = make_array(maxd*maxd, /float)
; repeat for each permutation
for i=1, maxd do begin
  maxdist_old=1000000.0
  for j=1, maxd do begin
    maxdist1 = sqrt((max_ix[i]-max_ix[j])^2+(max_iy[i]-max_iy[j])^2)
    if (maxdist1 gt 0.0) then begin
      if maxdist1 lt maxdist_old then begin
        maxdist_old = maxdistl
      endif
    endif
  endfor
  max_distl[i] = maxdist_old
endfor
; matrix containing distances to nearest/ next local maximum = peak distances distribution
max_dist = max_distl[0 maxd-1]
; xxxxxxxxxxxxxxxxxxxxxxxxxxxxxxxxxxx
; results
; xxxxxxxxxxxxxxxxxxxxxxxxxxxxxxxxxxx
; amount of local maxima
print, max(d)
; peak density in 1/μm^2
print, float(maxd)/imagesizex/ imagesizey * 1EE
; average and standard deviation of nearest peak distance in nm
print, mean(max_dist)
print, stddev(max_dist)
; average and standard deviation of local peak height in nm
print, mean(level_diff)
print, stddev(level_diff)
; average and standard deviation of local peak diameter in nm
print, mean(2.0*level_loc)
print, stddev(2.0*level_loc)
; average and standard deviation of local peak gradient in nm
print, mean(level_grad)
print, stddev(level_grad)
End
; xxxxxxxxxxxxxxxxxxxxxxxxxxxx
; End of routine analyse_peaks
; xxxxxxxxxxxxxxxxxxxxxxxxxxxx
```

All publications, patent applications, patents, and other references mentioned herein including the appendix, are incorporated by reference herein in their entirety.

Still other embodiments are in the following claims.

What is claimed is:

1. An endoprosthesis, comprising:
a stent having an abluminal surface and an adluminal surface, the abluminal surface including a ceramic having a surface characterized by a first uniform morphology of defined grains with an aspect ratio of about 5:1 or more, and the adluminal surface including another ceramic having a surface characterized by a second uniform morphology different from the first uniform morphology of the surface of the ceramic on the abluminal surface, the abluminal surface having a surface morphology different from a surface morphology of the adluminal surface, wherein the abluminal surface morphology is characterized by defined grains and the adluminal surface morphology is characterized by globular morphology.

2. The endoprosthesis of claim 1 wherein the aspect ratio is about 10:1 to 20:1.

3. The endoprosthesis of claim 1 wherein the grains have a length from about 50 nm-400 nm.

4. The endoprosthesis of claim 1 wherein the grains have a width of about 5 to 15 nm.

5. The endoprosthesis of claim 1 wherein the ceramic on the abluminal surface has a peak distance of about 200 nm or less.

6. The endoprosthesis of claim 1 wherein the ceramic on the abluminal surface has a peak height of about 400 nm or less.

7. The endoprosthesis of claim 1 wherein the ceramic on the abluminal surface has an Sdr of about 120 to 200.

8. The endoprosthesis of claim 1 wherein the ceramic on the abluminal surface has an Sq of about 20 or more.

9. The endoprosthesis of claim 1 further including a coating over the ceramic on the abluminal surface.

10. The endoprosthesis of claim 9 wherein the coating is formed of a polymer.

11. The endoprosthesis of claim 9 wherein the coating includes a drug.

12. The endoprosthesis of claim 1 wherein the ceramic on the abluminal surface is IROX.

13. An endoprosthesis comprising:
a stent having an abluminal surface and an adluminal surface, the abluminal surface including a ceramic having a surface characterized by a uniform morphology and an Sdr of about 100 or greater, and the adluminal surface including another ceramic having a surface characterized by another uniform morphology different from the uniform morphology of the surface of the ceramic of the abluminal surface, the abluminal surface having a surface morphology different from a surface morphology of the adluminal surface, wherein the abluminal surface morphology is characterized by defined grains and the adluminal surface morphology is characterized by globular morphology.

14. The endoprosthesis of claim 13 wherein said Sdr is about 120 to 200.

15. The endoprosthesis of claim 13 wherein said Sdr is about 150 or greater.

16. The endoprosthesis of claim 13 wherein said Sdr is about 180 or greater.

17. The endoprosthesis of claim 13 wherein said ceramic on the abluminal surface has an Sq of about 20 or more.

18. The endoprosthesis of claim 17 wherein said Sq is about 20 to 30.

19. The endoprosthesis of claim 13 wherein the Sdr has a uniformity of about +/−20% or less.

20. The endoprosthesis of claim 13 wherein the ceramic on the abluminal surface includes defined grains having an aspect ratio of about 5:1 or more.

21. The endoprosthesis of claim 20 wherein the aspect ratio is about 10:1 to 20:1.

22. The endoprosthesis of claim 20 wherein the grains have a length from about 50 nm-200 nm.

23. The endoprosthesis of claim 20 wherein the grains have a width of about 5 nm to 15 nm.

24. The endoprosthesis of claim 13 wherein the ceramic on the abluminal surface has a peak distance of about 400 nm or less.

25. The endoprosthesis of claim 13 wherein the ceramic on the abluminal surface has a peak height of about 400 nm or less.

26. The endoprosthesis of claim 13 further including a coating over the ceramic on the abluminal surface.

27. The endoprosthesis of claim 26 wherein the coating is formed of polymer.

28. The endoprosthesis of claim 26 wherein the coating includes drug.

29. The endoprosthesis of claim 13 wherein the ceramic on the abluminal surface is a coating on a metal.

30. The endoprosthesis of claim 13 wherein the ceramic on the abluminal surface is IROX.

31. An endoprosthesis, comprising:
a stent having an abluminal surface and an adluminal surface, the adluminal surface including a ceramic having a surface characterized by a uniform morphology of globular features having a peak height of about 20 nm or less, a diameter of about 100 nm or less, and a peak distance of about 200 nm or less, and the abluminal surface including another ceramic having a surface characterized by another uniform morphology different from the uniform morphology of the surface of the ceramic of the adluminal surface, the abluminal surface having a surface morphology different from a surface morphology of the adluminal surface, wherein the abluminal surface morphology is characterized by defined grains and the adluminal surface morphology is characterized by globular morphology.

32. The endoprosthesis of claim 31 wherein the ceramic on the adluminal surface has an Sq of about 10 or less.

33. The endoprosthesis of claim 31 wherein the ceramic on the adluminal surface has an Sdr of about 10 or less.

34. The endoprosthesis of claim 31 wherein the ceramic on the adluminal surface is exposed to tissue, free of an overcoat.

35. An endoprosthesis, comprising:
a stent having an abluminal surface and an adluminal surface, wherein
at least 25% of one of the adluminal surface and the abluminal surface is covered by a first ceramic having a surface characterized by a uniform morphology, the uniform morphology having an Sdr of about 10 or less and an Sdr uniformity of about +/−10%, and
at least a portion of the other one of the adluminal surface and the abluminal surface is covered by a second ceramic having a surface characterized by another uniform morphology different from the uniform morphology of the surface of the first ceramic, the abluminal surface having a surface morphology different from a surface morphology of the adluminal surface, wherein the abluminal surface morphology is characterized by defined grains and the adluminal surface morphology is characterized by globular morphology.

36. An endoprosthesis, comprising:
a stent having an abluminal surface and an adluminal surface, the abluminal surface including a ceramic having a surface characterized by a first uniform morphology of defined grains and a polymer coating over the ceramic, and the adluminal surface including another ceramic having a surface characterized by a second uniform morphology different from the first uniform morphology of the surface of the ceramic on the abluminal surface, the abluminal surface having a surface morphology different from a surface morphology of the adluminal surface, wherein the abluminal surface morphology is characterized by defined grains and the adluminal surface morphology is characterized by globular morphology.

37. An endoprosthesis, comprising:
a stent having an abluminal surface and an adluminal surface, the abluminal surface including a ceramic coating having a surface characterized by an Sdr of about 1 or more and a polymer coating over the ceramic, and the adluminal surface including another ceramic having a surface characterized by a different morphology than the surface of the ceramic on the abluminal surface the abluminal surface having a surface morphology different from a surface morphology of the adluminal surface, wherein the abluminal surface morphology is characterized by defined grains and the adluminal surface morphology is characterized by globular morphology.

38. An endoprosthesis, comprising:
a stent having an abluminal surface and an adluminal surface, the abluminal surface including a first ceramic having a surface characterized by a uniform morphology of defined grains, and the adluminal surface including a second ceramic having a surface characterized by a uniform morphology of globular features, the abluminal surface having a surface morphology different from a surface morphology of the adluminal surface, wherein the abluminal surface morphology is characterized by defined grains and the adluminal surface morphology is characterized by globular morphology.

39. An endoprosthesis, comprising:
a stent having an abluminal surface and an adluminal surface, the adluminal surface including a first ceramic having a surface characterized by an Sdr of about 10 or less, and the abluminal surface including a second ceramic having a surface characterized by an Sdr of about 100 or more, the abluminal surface having a surface morphology different from a surface morphology of the adluminal surface, wherein the abluminal surface morphology is characterized by defined grains and the adluminal surface morphology is characterized by globular morphology.

* * * * *

UNITED STATES PATENT AND TRADEMARK OFFICE
CERTIFICATE OF CORRECTION

PATENT NO. : 7,976,915 B2
APPLICATION NO. : 11/752772
DATED : July 12, 2011
INVENTOR(S) : Torsten Scheuermann et al.

Page 1 of 1

It is certified that error appears in the above-identified patent and that said Letters Patent is hereby corrected as shown below:

Cover Page, under item [56] col. 2, line 1, Other Publications: delete "Topography", and insert -- Topology --.

Column 19, Claim 37, Line 25: after "surface" insert -- , --.

Signed and Sealed this
Twentieth Day of September, 2011

David J. Kappos
*Director of the United States Patent and Trademark Office*